(12) United States Patent
Koshinsky et al.

(10) Patent No.: US 12,319,957 B2
(45) Date of Patent: *Jun. 3, 2025

(54) NUCLEIC ACID ANALYSIS BY JOINING BARCODED POLYNUCLEOTIDE PROBES

(71) Applicant: AFFYMETRIX, INC., Carlsbad, CA (US)

(72) Inventors: Heather Koshinsky, El Cerrito, CA (US); John D. Curry, Concord, CA (US); Robert O'Callahan, Spring, TX (US); Adam Mccoy, Davis, CA (US); Daniel Fitzpatrick, Santa Clara, CA (US); Philip H. Dickinson, Cupertino, CA (US); Anthony C. Schweitzer, Redwood City, CA (US)

(73) Assignee: AFFYMETRIX, INC., Carlsbad, CA (US)

( * ) Notice: Subject to any disclaimer, the term of this patent is extended or adjusted under 35 U.S.C. 154(b) by 912 days.

This patent is subject to a terminal disclaimer.

(21) Appl. No.: 17/458,995

(22) Filed: Aug. 27, 2021

(65) Prior Publication Data

US 2022/0049296 A1 Feb. 17, 2022

Related U.S. Application Data

(63) Continuation of application No. 15/758,065, filed as application No. PCT/US2016/060991 on Nov. 8, 2016, now Pat. No. 11,118,216.
(Continued)

(51) Int. Cl.
*C12Q 1/6848* (2018.01)
*C12Q 1/6827* (2018.01)
(Continued)

(52) U.S. Cl.
CPC ......... *C12Q 1/6848* (2013.01); *C12Q 1/6827* (2013.01); *C12Q 1/6853* (2013.01);
(Continued)

(58) Field of Classification Search
CPC ................... C12Q 2525/161; C12Q 2521/501
See application file for complete search history.

(56) References Cited

U.S. PATENT DOCUMENTS

| | | | |
|---|---|---|---|
| 5,912,124 | A | 6/1999 | Kumar et al. |
| 6,027,889 | A | 2/2000 | Barany et al. |

(Continued)

FOREIGN PATENT DOCUMENTS

| | | | |
|---|---|---|---|
| CN | 101395280 A | | 3/2009 |
| CN | 104830993 A | | 8/2015 |

(Continued)

OTHER PUBLICATIONS

Baird et al., "Rapid SNP Discovery and Genetic Mapping Using Sequenced RAD Markers," PLoS ONE, Oct. 2008, vol. 3, Issue 10, e3376, pp. 1-7.
(Continued)

*Primary Examiner* — Samuel C Woolwine
(74) *Attorney, Agent, or Firm* — BUCHANAN INGERSOLL & ROONEY PC

(57) ABSTRACT

Disclosed are compositions, methods and kits for determining the presence, absence, amount, copy number, or other characteristics of one or more polynucleotide sequences in two or more samples and use thereof in genotyping, evaluation of copy number variation, expression analysis, determination of splice variants and fusion genes, and other genetic analyses.

20 Claims, 27 Drawing Sheets

Specification includes a Sequence Listing.

Related U.S. Application Data

(60) Provisional application No. 62/353,088, filed on Jun. 22, 2016, provisional application No. 62/317,879, filed on Apr. 4, 2016, provisional application No. 62/289,303, filed on Jan. 31, 2016, provisional application No. 62/215,679, filed on Sep. 8, 2015.

(51) Int. Cl.
  *C12Q 1/6853*  (2018.01)
  *C12Q 1/686*  (2018.01)
  *C12Q 1/6862*  (2018.01)
  *C12Q 1/6876*  (2018.01)

(52) U.S. Cl.
  CPC ......... *C12Q 1/6862* (2013.01); *C12Q 1/6876* (2013.01); *C12Q 1/686* (2013.01); *C12Q 2525/155* (2013.01); *C12Q 2525/161* (2013.01); *C12Q 2525/204* (2013.01)

(56) References Cited

U.S. PATENT DOCUMENTS

| | | |
|---|---|---|
| 6,124,092 A | 9/2000 | O'Neill et al. |
| 6,511,810 B2 | 1/2003 | Bi et al. |
| 6,518,025 B1 | 2/2003 | Steinborn et al. |
| 6,534,293 B1 | 3/2003 | Barany et al. |
| 7,504,218 B2 | 3/2009 | Happe et al. |
| 7,846,657 B2 | 12/2010 | Van et al. |
| 7,935,488 B2 | 5/2011 | Zabeau et al. |
| 8,460,866 B2 | 6/2013 | Van et al. |
| 2003/0119004 A1 | 6/2003 | Wenz et al. |
| 2004/0224311 A1 | 11/2004 | Telles et al. |
| 2004/0229222 A1 | 11/2004 | Chui et al. |
| 2005/0272071 A1 | 12/2005 | Lao et al. |
| 2009/0029478 A1 | 1/2009 | Puskas |
| 2009/0053687 A1 | 2/2009 | Colau et al. |
| 2009/0136938 A1 | 5/2009 | Tao et al. |
| 2010/0267585 A1 | 10/2010 | Terbrueggen et al. |
| 2011/0003290 A1 | 1/2011 | Gale et al. |
| 2011/0045462 A1 | 2/2011 | Fu et al. |
| 2011/0136116 A1 | 6/2011 | Barany et al. |
| 2011/0159499 A1 | 6/2011 | Hindson et al. |
| 2011/0244454 A1 | 10/2011 | Franks et al. |
| 2012/0003633 A1 | 1/2012 | Kuijpers et al. |
| 2015/0167077 A1 | 6/2015 | Fehr et al. |
| 2016/0222447 A1 | 8/2016 | Stevens et al. |

FOREIGN PATENT DOCUMENTS

| | | |
|---|---|---|
| EP | 1130113 A1 | 9/2001 |
| EP | 1319718 A1 | 6/2003 |
| EP | 1602733 A1 | 12/2005 |
| WO | WO-2004076692 A1 | 9/2004 |
| WO | WO-2005001113 A2 | 1/2005 |
| WO | WO-2005021794 A2 | 3/2005 |
| WO | WO-2005026389 A2 | 3/2005 |
| WO | WO-2007100243 A1 | 9/2007 |
| WO | WO-2013106807 A1 | 7/2013 |

OTHER PUBLICATIONS

CN Office Action cited in 201680052075.1 dated Apr. 28, 2021.
Extended European Search Report for Application No. 16845310.8, mailed Jan. 4, 2019, 7 pages.
Fujimoto et al., "Reversible photoligation of DNA via 5-vinyldeoxyuridine," Nucleic Acids Symposium Series No. 42, 1999, pp. 39-40.
Hu Fuquan: "Modern Gene Manipulation Technology", People's Military Medical Publishing House, Oct. 31, 2000, ISBN 7-80157-111-8, pp. 263-266.
International Search Report and Written Opinion for Application No. PCT/US2013/21379, mailed Apr. 26, 2013, 8 pages.
Kumar et al., "Template-Directed Oligonucleotide Strand Ligation, Covalent Intramolecular DNA Circularization and Catenation Using Click Chemistry," Journal of the American Chemical Society, 2007, vol. 129, pp. 6859-6864.
Kvastad L., et al., "Single Cell Analysis of Cancer Cells Using An Improved RT-MLPA Method has Potential for Cancer Diagnosis and Monitoring," Scientific Reports, vol. 5, No. 1, Nov. 12, 2015 (Nov. 12, 2015), XP055535938, pp. 1-12, DOI: 10.1038/srep16519.
Lewis et al., "High-Density Detection of Restriction-Site-Associated DNA Markers for Rapid Mapping of Mutated Loci in Neurospora," Genetics, Oct. 2007, vol. 177, pp. 1163-1171.
Li, Xhang Yang, et al., "High-throughput genotyping MLPA assay in RHD genotyping for a Chinese pedigree with Del phenotype", Chin J. Blood Transfusion Jun. 2012, vol. 25, No. 06.
Margulies et al., "Genome Sequencing in Microfabricated High-Density Picolitre Reactors", Nature, vol. 437, No. 15, 2005, pp. 376-380.
Miller et al., "RAD marker microarrays enable rapid mapping of zebrafish mutations," Genome Biology, 2007, vol. 8, Issue 6, Article R105, 10 pages.
Miller et al., "Rapid and cost-effective polymorphism identification and genotyping using restriction site associated DNA (RAD) markers," Genome Research, 2007, vol. 17, pp. 240-248.
PCT/US2016/060991, International Search Report and Written Opinion mailed Mar. 16, 2017, 10 pages.
Sando et al., "Nonenzymatic DNA ligation in Escherichia coli cells," Nucleic Acids Research Supplement No. 2, 2002, pp. 121-122.
Shabarova et al., "Chemical ligation of DNA: the first non-enzymatic assembly of a biologically active gene," Nucleic Acids Research, 1991, vol. 19, No. 15, pp. 4247-4251.
Thallman et al., "Efficient computation of genotype probabilities for loci with many alleles: II. Iterative method for large, complex pedigrees," Journal of Animal Science, 2001, vol. 79, pp. 34-44.
Xu, Y et al., "High sequence fidelity in a non-enzymatic DNA autoligation reaction", Nucl. Acids Res. vol. 27(3), 1999, pp. 875-881.
Zhang Li, et al., "Genetic diagnosis of thalassemias by multiplex ligation-dependent probe amplification combined with direct sequencing", Pract Prev Med, Jul. 2014, vol. 21, No. 7.
Ji Yan-Li., et al., "Application of High through-put MLPA Gene Typing Technique in the Identification of 1 Del phenotypic Family Gene", Chinese Journal of Blood Transfusion, Jun. 25, 2012, vol. 25, No. 6, pp. 542-546.
Zhang Li, et al., "Combined application of MLPA and sequencing technique in the detection of Thalassemia gene defects", Practical Preventive Medicine, Jul. 25, 2014, No. 7, pp. 779-781.

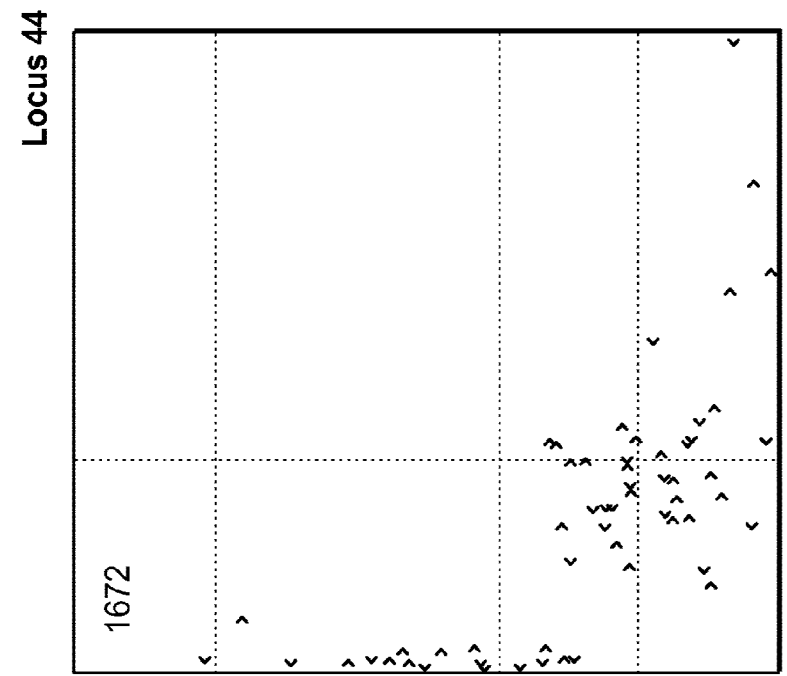
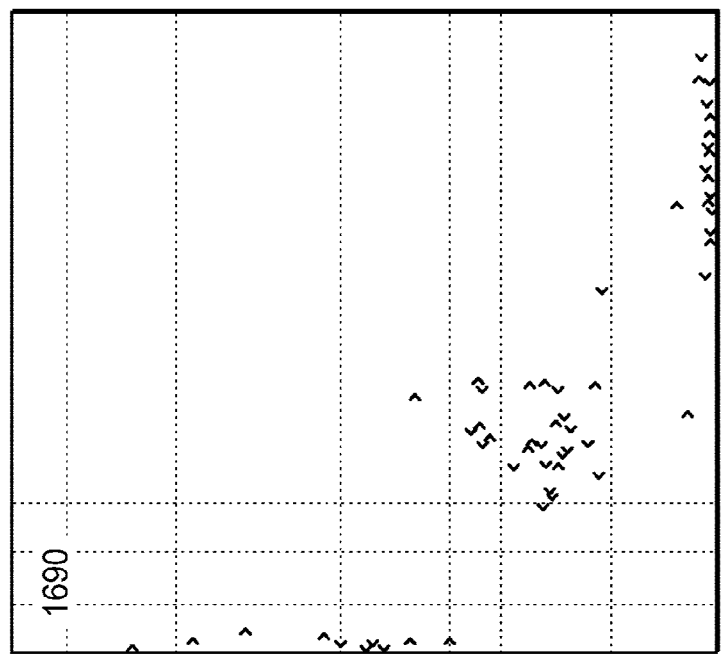
FIG. 2C

Top

Expressed as number of bovine genomes

Relative Concordance / Signal Genome

| | 0 | 61 | 122 | 244 | 488 | 976 | 1953 | 3906 | 7812 | 15625 | 31250 | 62500 | 125000 |
|---|---|---|---|---|---|---|---|---|---|---|---|---|---|
| Noise Genome 0 | 1 | 1 | 1 | 1 | 1 | 1 | 1 | 1 | 1 | 1 | 1 | 1 | 1 |
| 125000 | 0.4 | 1 | 1 | 0.5 | 0.833333 | 1 | 1 | 1 | 1 | 1 | 1 | 1 | 1 |
| 250000 | 1 | 1 | 1 | 0.75 | 0.833333 | 1 | 1 | 1 | 1 | 1 | 1 | 1 | 1 |

=0.0488%

Bottom

Expressed as ng DNA into the starting reaction

Relative Concordance / Signal Genome

| | 0.12207 | 0.24414 | 0.48825 | 0.976565 | 1.953125 | 3.90625 | 7.8125 | 15.625 | 31.25 | 62.5 | 125 | 250 |
|---|---|---|---|---|---|---|---|---|---|---|---|---|
| Noise Genome 0 | 1 | 1 | 1 | 1 | 1 | 1 | 1 | 1 | 1 | 1 | 1 | 1 |
| 250 | 0.4 | 1 | 0.5 | 0.833333 | 0.833333 | 1 | 1 | 1 | 1 | 1 | 1 | 1 |
| 500 | 1 | 1 | 0.75 | 0.833333 | 1 | 1 | 1 | 1 | 1 | 1 | 1 | 1 |

FIG. 4A

Top

Expressed as number of bovine genomes

Signal Genome

| AY842473 | | 61 | 122 | 244 | 488 | 976 | 1953 | 3906 | 7812 | 15625 | 31250 | 62500 | 125000 |
|---|---|---|---|---|---|---|---|---|---|---|---|---|---|
| | 0 | 4855 | 2798 | 1966 | 1378.5 | 904.5 | 619 | 1470.5 | 2287.5 | 1845 | 3638.5 | 3401 | 5172 |
| Noise Genome | 125000 | 273 | 96.33333 | 328.3333 | 266.3333 | 406.3333 | 422.6667 | 825.6667 | 1101 | 2847.333 | 3820 | 4386 | 5135.667 |
| | 250000 | 147 | 233.6667 | 244.6667 | 193.3333 | 331.3333 | 639.3333 | 823.3333 | 1849 | 3158 | 2973 | 3848.667 | 4784 |

Bottom

Expressed as ng DNA into the starting reaction

Signal Genome

| AY842473 | | 0.12207 | 0.24414 | 0.48825 | 0.976565 | 1.953125 | 3.90625 | 7.8125 | 15.625 | 31.25 | 62.5 | 125 | 250 |
|---|---|---|---|---|---|---|---|---|---|---|---|---|---|
| | 0 | 4855 | 2798 | 1966 | 1378.5 | 904.5 | 619 | 1470.5 | 2287.5 | 1845 | 3638.5 | 3401 | 5172 |
| Noise Genome | 250 | 273 | 96.33333 | 328.3333 | 266.3333 | 406.3333 | 422.6667 | 825.6667 | 1101 | 2847.333 | 3820 | 4386 | 5135.667 |
| | 500 | 147 | 233.6667 | 244.6667 | 193.3333 | 331.3333 | 639.3333 | 823.3333 | 1849 | 3158 | 2973 | 3848.667 | 4784 |

FIG. 4B

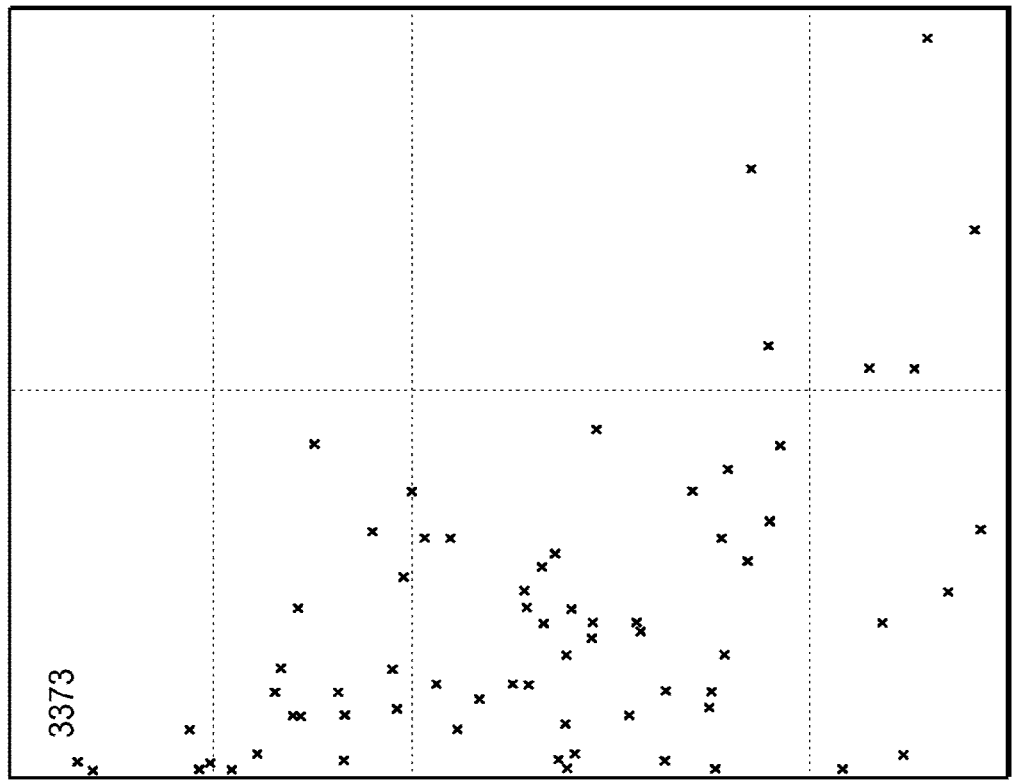
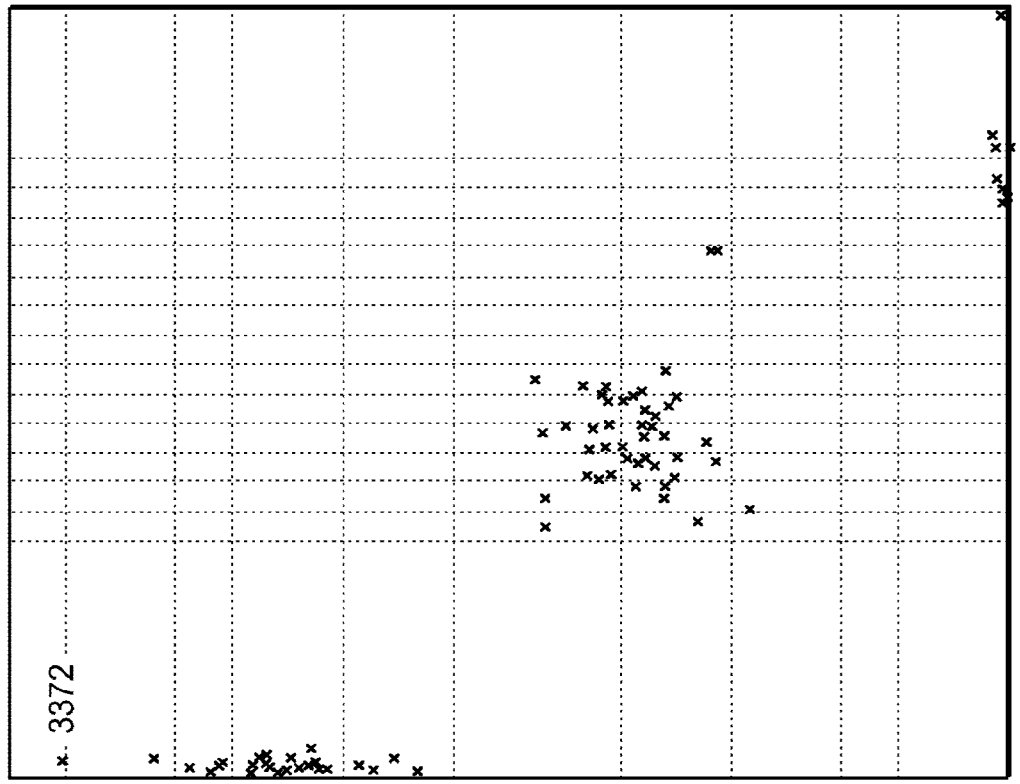
FIG. 5A
FIG. 5B

FIG. 7A
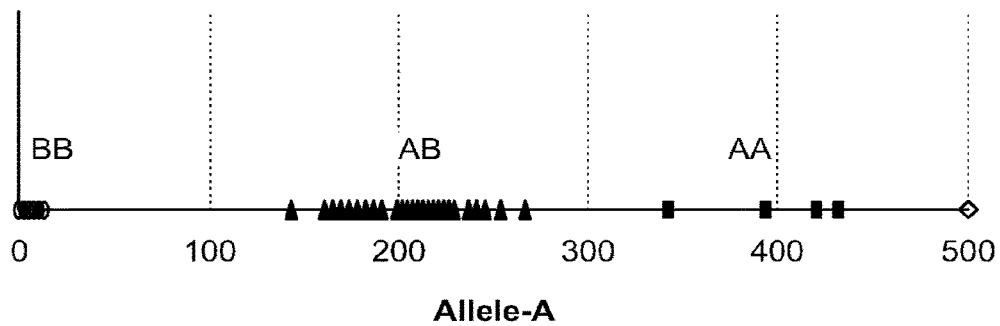
FIG. 7B
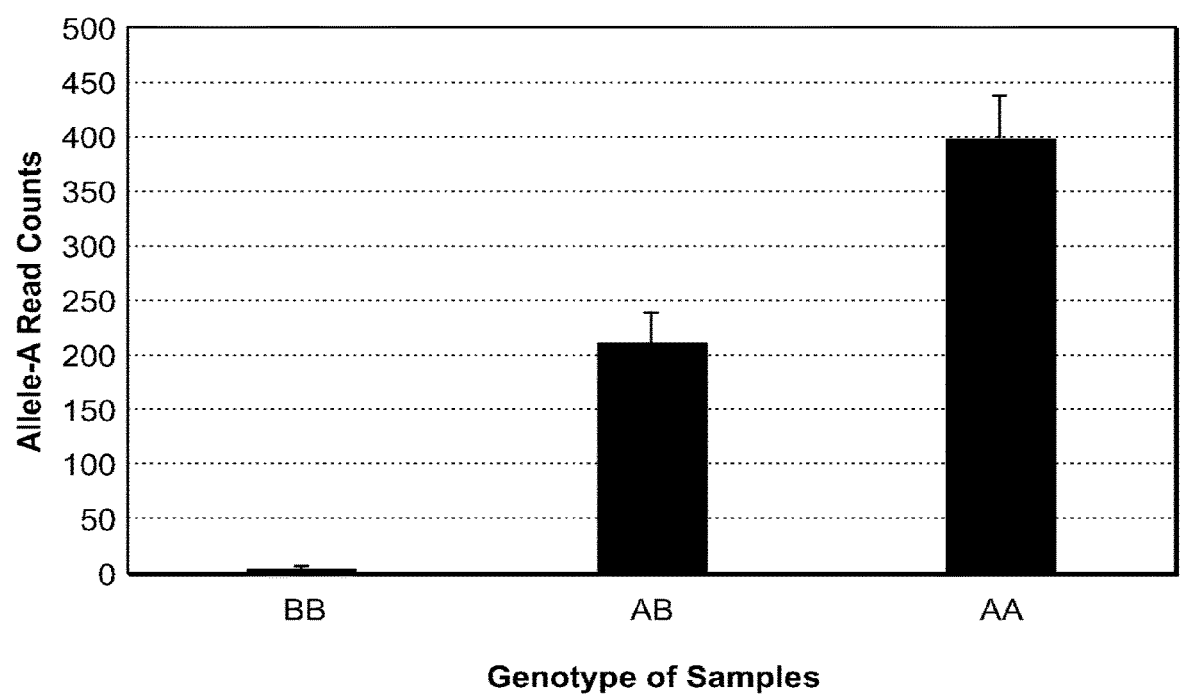
FIG. 7C
| Copy of target | 0 | 1 | 2 |

Locus 804

[TTC/-]

45kb deletion

FIG. 18A  Eureka Assay on genomic DNA
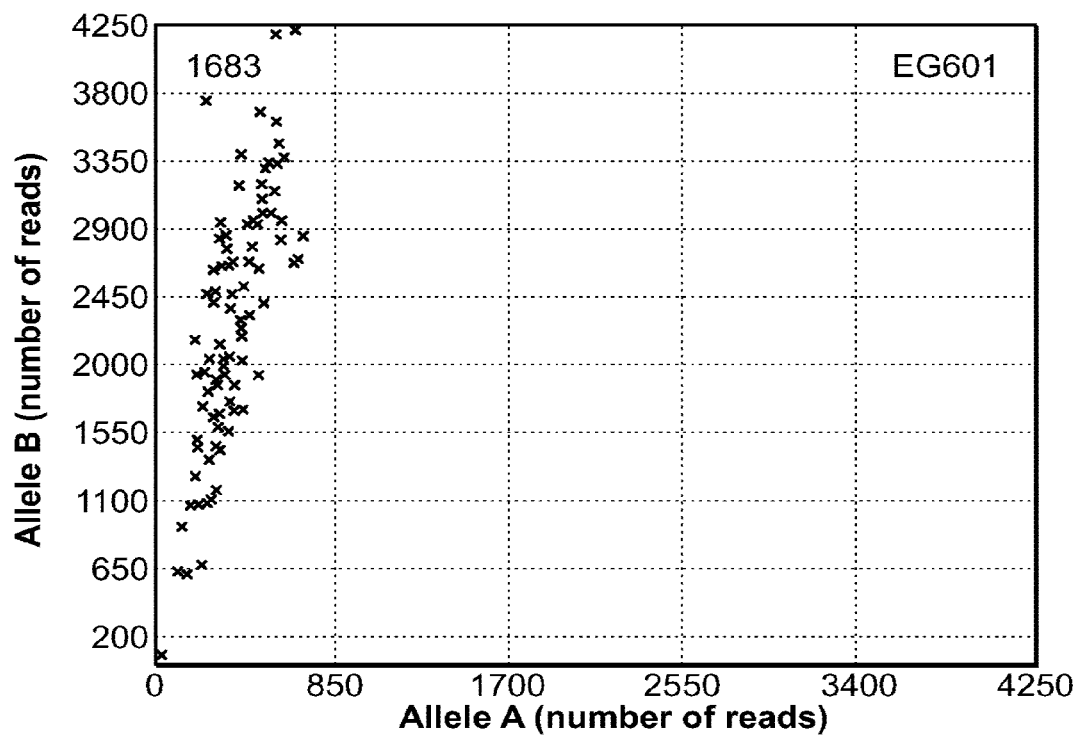
FIG. 18B  Eureka Assay on PCR amplicons that isolate the target ("enrich selected genome")
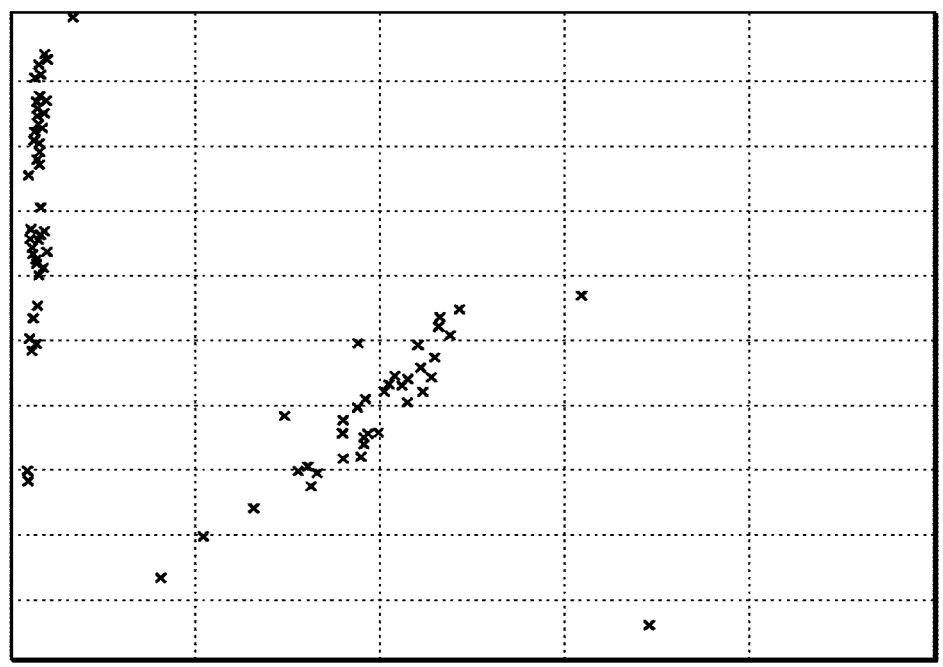

SEQUENCE LISTING

<160> NUMBER OF SEQ ID NOS: 10

<210> SEQ ID NO 1

```
<211> LENGTH: 10
<212> TYPE: DNA
<213> ORGANISM: Artificial
<220> FEATURE:
<223> OTHER INFORMATION: LHS_T probe

<400> SEQUENCE: 1
tgtgacaact                                                                10

<210> SEQ ID NO 2
<211> LENGTH: 21
<212> TYPE: DNA
<213> ORGANISM: Artificial
<220> FEATURE:
<223> OTHER INFORMATION: gDNA

<400> SEQUENCE: 2
acactgttgt gacgtccttt t                                                   21

<210> SEQ ID NO 3
<211> LENGTH: 72
<212> TYPE: DNA
<213> ORGANISM: Artificial
<220> FEATURE:
<223> OTHER INFORMATION: barcode

<400> SEQUENCE: 3
caagcagaag acggcatacg agatcggaag aagatgccag tgactggagt tcagacgtgt         60
gctcttccga tc                                                             72

<210> SEQ ID NO 4
<211> LENGTH: 72
<212> TYPE: DNA
<213> ORGANISM: Artificial
<220> FEATURE:
<223> OTHER INFORMATION: barcode

<400> SEQUENCE: 4
caagcagaag acggcatacg agatcggaag aagatgccag tgactggagt tcagacgtgt         60
gctcttccga tc                                                             72

<210> SEQ ID NO 5
<211> LENGTH: 72
<212> TYPE: DNA
<213> ORGANISM: Artificial
<220> FEATURE:
<223> OTHER INFORMATION: barcode

<400> SEQUENCE: 5
caagcagaag acggcatacg agatcggaag aagatgccag tgactggagt tcagacgtgt         60
gctcttccga tc                                                             72

<210> SEQ ID NO 6
<211> LENGTH: 72
<212> TYPE: DNA
<213> ORGANISM: Artificial
<220> FEATURE:
<223> OTHER INFORMATION: barcode

<400> SEQUENCE: 6
caagcagaag acggcatacg agatcggaag aagatgccag tgactggagt tcagacgtgt         60
gctcttccga tc                                                             72
```

```
<210> SEQ ID NO 7
<211> LENGTH: 72
<212> TYPE: DNA
<213> ORGANISM: Artificial
<220> FEATURE:
<223> OTHER INFORMATION: barcode

<400> SEQUENCE: 7
caagcagaag acggcatacg agatatagaa gatcggatgg tgactggagt tcagacgtgt      60
cgtcttccga tc                                                          72

<210> SEQ ID NO 8
<211> LENGTH: 72
<212> TYPE: DNA
<213> ORGANISM: Artificial
<220> FEATURE:
<223> OTHER INFORMATION: barcode

<400> SEQUENCE: 8
caagcagaag acggcatacg agatatagaa gatcggatgg tgactggagt tcagacgtgt      60
gctcttccga tc                                                          72

<210> SEQ ID NO 9
<211> LENGTH: 72
<212> TYPE: DNA
<213> ORGANISM: Artificial
<220> FEATURE:
<223> OTHER INFORMATION: barcode

<400> SEQUENCE: 9
caagcagaag acggcatacg agatagttgg tcggaaggag tgactggagt tcagacgtgt      60
gctcttccga tc                                                          72

<210> SEQ ID NO 10
<211> LENGTH: 72
<212> TYPE: DNA
<213> ORGANISM: Artificial
<220> FEATURE:
<223> OTHER INFORMATION: barcode

<400> SEQUENCE: 10
caagcagaag acggcatacg agatagttgg tcggaaggag tgactggagt tcagacgtgt      60
gctcttccga tc                                                          72
```

NUCLEIC ACID ANALYSIS BY JOINING BARCODED POLYNUCLEOTIDE PROBES

RELATED APPLICATIONS

This application is a continuation of U.S. application Ser. No. 15/758,065, filed Mar. 7, 2018, which is a National Stage Entry under 35 U.S.C. Section 371 of International Patent Application No. PCT/US2016/060991, filed Nov. 8, 2016, which claims priority to U.S. provisional patent application No. 62/215,679, filed Sep. 8, 2015, U.S. provisional patent application No. 62/289,303, filed Jan. 31, 2016, U.S. provisional patent application No. 62/317,879, filed Apr. 4, 2016, and U.S. provisional patent application No. 62/353,088, filed Jun. 22, 2016. Each of the foregoing applications are incorporated herein by this reference in their entireties.

INCORPORATION BY REFERENCE OF SEQUENCE LISTING

The Sequence Listing document filed in conjunction with this application includes a numerical listing of sequences corresponding to the sequences described herein, each identified by a unique SEQ ID NO. The 22619-2a-1-1_Sequence_Listing.txt file was created on Aug. 26, 2021 and has a size of 2,760 bytes. The 22619-2a-1-1_Sequence_Listing.txt file is expressly incorporated herein by this reference.

TECHNICAL FIELD

The invention relates to compositions, methods and kits for nucleic acid analysis of two or more samples while preserving the identity of each sample.

BACKGROUND

There is a need for methods that can be used in genetic analysis that preserve the identity of each sample and facilitate a multiplexed processing approach in contexts such as genotyping, copy number analysis, expression analysis, epigenetic profiling, and determining the presence, absence or amount of a particular gene, SNP, indel, transcript, or genetic locus. The present invention addresses this need.

SUMMARY

The present disclosure provides, among other things, compositions, methods and kits for nucleic acid analysis of target polynucleotides. The analysis may include determining the presence or absence of a plurality of target polynucleotides in two or more samples. In other aspects, the analysis may be in the context of genotyping one or more alleles, analyzing copy number variations, profiling of epigenetic events such as methylation, or analyzing the expression of one or more RNA transcripts in the two or more samples.

The methods may comprise the steps of: providing two or more samples, each sample comprising one or more target polynucleotides, each target polynucleotide comprising a first target sequence and a second target sequence; providing a plurality of first and second complementary probes, (i) each first complementary probe having a sequence portion that is complementary to a first target sequence, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence and an immediately adjacent sequence portion that is non-complementary to the second target sequence; incubating the plurality of first and second complementary probes with each independent sample under hybridization conditions such that first and second complementary probes hybridize to their complementary target polynucleotide in a sample to form a hybridization complex; joining first and second complementary probes that are hybridized to first and second target sequences in a sample to form a product polynucleotide; pooling product polynucleotides formed from independent samples; and determining the presence or absence of target polynucleotides in one or more samples by analyzing product polynucleotides or the complement thereof.

The first and second complementary probes may be complementary to first and second target sequences and may be immediately adjacent one another or adjacent one another and from one to 500 nucleotides apart.

The first complementary probe may have a sequence having two portions that is complementary to the target sequence and flanking both 3' and 5' of the interrogation site bar code, and the adjacent universal sequence of the first complementary probe may be 5' to the complementary sequence portion that may be 5' to the non-complementary interrogation site bar code of the first complementary probe.

The non-complementary portion of the first and second complementary probes may comprise a universal sequence and may also comprise additional sequences effective to normalize the length of product polynucleotides in a given assay. The universal sequences for the first and second complementary probes may be the same or different.

The universal sequence may include a primer binding sequence that is complementary to a primer sequence which can be used to add one or more of (i) a sample index, (ii) a sequence for sequence data generation or another form of detection (such as an adapter for next generation sequencing, a capture probe or sequence for capture on a solid surface), and (iii) other moieties (e.g. a moiety that may be used in next next generation sequencing ("NNGG")).

The primer sequence may include a PCR priming sequence.

The non-complementary interrogation site bar code and the sample index may be 10, 11, 12, 13, 14, 15 or 16 nucleotides in length, e.g., 12 or 15 nucleotides in length. The interrogation site bar code may be selected from SEQ ID NO: 1-SEQ ID NO: 384. The sample index bar code may be selected from SEQ ID NO: 1-SEQ ID NO: 73536.

In carrying out the methods, the first and second complementary probe composition may be heated to a temperature of from 70 to 100° C. prior to the hybridization step. The product polynucleotides may be enriched prior to the pooling step, for example by PCR amplification of the product polynucleotides.

The compositions and methods may be solution-based and each of the first and second complementary probes may comprise an inosine 2, 3, 4, 5, 6, 7, 8, 9, 10, or more bases from the 3' and 5' end of the probe, respectively.

The disclosure provides compositions, methods and kits that may be used for genotyping, determining copy number variation, and/or for determining the presence or absence or amount of specific target polynucleotides.

Additional features and advantages of the present disclosures are set forth in the description which follows. These and other features of the disclosure will become more fully apparent from the following description or can be learned by the practice of the principles set forth herein.

BRIEF DESCRIPTION OF THE DRAWINGS

FIGS. 2A-2C illustrates the results of a study on the effect of interrogation site bar code placement in the first complementary probe. The figure shows cluster plots of several loci and two strategies for interrogation barcode placement in the first complementary probe. The plots on the left (6mer) have a short interrogation site bar code (6 nucleotides) between the first target sequence and the universal sequence (with the 6-mer "between" the first target sequence and the universal sequence). The plots on the right (12mer) have a longer interrogation site bar code (12 nucleotides) within the first target sequence, such that there is complementary sequence on both sides of the interrogation site bar code (with the 12-mer within the first target sequence). The number of reads for Allele-A (x-axis) and Allele-B (y-axis) are shown, where each point is a unique sample (the same 96 samples in each treatment). AA animals are along the x-axis, BB animals are along the y-axis, and AB animals are centered between the axes. The plots show that in some cases genotype resolution is similar and in other cases the genotype resolution with one or the other placement is better. As indicated in the FIG. 2A, the results where the first complementary probe had a 12-mer interrogation site bar code that contains information on both the allele and the locus and has a complementary sequence on both sides of the interrogation site bar code produces clearer genotype clusters than the results for the results where the first complementary probe had a 6-mer interrogation site bar code that contains information on the allele and locus in different sequences and does not have complementary sequence on both sides of the interrogation site bar code (FIG. 2A). In this case, the interrogation site bar code is immediately adjacent to the target sequence and the universal sequence. As indicated in the FIG. 2B, both sets produced similar genotype clusters. As indicated in the FIG. 2C, the genotype clusters produced with the 6-mer interrogation site bar code provide slightly clearer genotype clusters.

FIGS. 4A and 4B show the results of a study where a small amount of target DNA was detected in a sample of background (noise) genomic DNA. FIG. 4A shows the average relative concordance of the two best loci for each treatment, the number of signal and noise genomes (Top), and ng of signal and noise genomes in each reaction (Bottom). The results show that as the number of signal genomes decreases the relative concordance of the two loci remain high. Even at 122 ng input signal genomes in a background of the equivalent of 250,000 noise genomes the average relative concordance is 100%. This is the detection of under 0.05% contamination of a signal genome in background of equivalent size noise genomes. FIG. 4B shows the average number of reads associated with a single locus for each treatment presented as the number of signal and noise genomes (Top) and ng of signal and noise genomes in each reaction (Bottom). As the number of signal genomes decreases the number of reads associated with the single locus also decreases and is largely independent of the amount of noise DNA present in the reaction.

FIGS. 5A and 5B illustrate the results of a study where a nucleic acid sample was or was not heated prior to carrying out a genotyping assay embodiment. Cluster plots show a single locus and presence (heat; FIG. 5A) or absence (no heat; 5B) of reversible denaturation in the workflow. Number of reads for Allele-A (x-axis) and Allele-B (y-axis) are shown, where each point is a unique sample (the same 96 samples in each treatment). AA animals are along the x-axis, BB animals are along the y-axis, and AB animals are centered between the axes. The plot for the reaction with the reversible denaturation (heat; FIG. 5A) shows three easy to distinguish genotype clusters. The plot for the reaction that lacks the reversible denaturation (no heat; FIG. 5B) does not show three easy to distinguish genotype clusters.

FIGS. 7A-7C illustrate the use of a copy number analysis embodiment in performing a copy number analysis to determine copy number variation (CNV). FIG. 7A shows the number of reads associated with the interrogation site bar code for the A allele of the target locus for individual samples shown on the X-axis. Circle=BB samples, triangle=AB samples, square=AA samples. FIG. 7B shows average read counts (bar) with standard deviation (whiskers) for the BB, AB and AA samples. FIG. 7C shows that the copy number of the A genetic locus is 0, 1, or 2.

FIG. 14A illustrates a scenario wherein both the destabilization site and the marker site are SNPs. FIG. 14B illustrates a scenario wherein the destabilization site is an insertion and the marker site is an SNP. FIG. 14C illustrates a scenario wherein the destabilization site is a deletion and the marker site is an SNP.

FIG. 15A illustrates a scenario wherein no proximal SNP is present in the target DNA. Hybridizations of LHS and RHS to the target DNA occur and LHS and RHS are ligated (cloud represents the ligation). FIG. 15B illustrates a scenario wherein the proximal SNP is present (the cross pointed by an arrow) in the target DNA. Hybridization between RHS and the target DNA is destabilized by the proximal SNP, and no ligation occurs.

FIG. 16A illustrates a scenario wherein no proximal SNP is present in the target DNA. Hybridizations of LHS and RHS to the target DNA occur and LHS and RHS are ligated (cloud represents the ligation). FIG. 16B illustrates a scenario wherein the proximal SNP is present (the cross pointed by an arrow). Hybridization between RHS and the target DNA is further prevented by the blocking oligo complementary to the target DNA having the proximal SNP, and no ligation occurs.

FIG. 17A illustrates a scenario wherein no proximal SNP is present in the target DNA. An upfront PCR amplification step is added using PCR primers that only amplify the unique genome or subgenome of interest based on the knowledge of the relative position of the proximal SNP(s) to the target/marker SNPs. Subsequently, hybridizations of LHS and RHS to the PCR amplicons of the target DNA occur and LHS and RHS are ligated (cloud represents the ligation). FIG. 17B illustrates a scenario wherein the proximal SNP is present (the cross pointed by an arrow) in the target DNA. The upfront PCR amplification is prevented by the proximal SNP(s) in the target DNA, which interferes with the binding of the PCR primer(s) to the target DNA.

FIGS. 18A and 18B illustrate the impact of an upfront PCR amplification step on sequence reads. Number of reads for Allele-A (x-axis) and Allele-B (y-axis) are shown, where each point is a unique sample. FIG. 18A shows results of cluster plots on genomic DNA without an upfront PCR amplification step. FIG. 18B shows results of cluster plots on PCR amplicons with an upfront PCR amplification step. The resolution of the cluster plots for the loci is improved with an enrichment PCR amplification step.

DETAILED DESCRIPTION

Figure 1A:
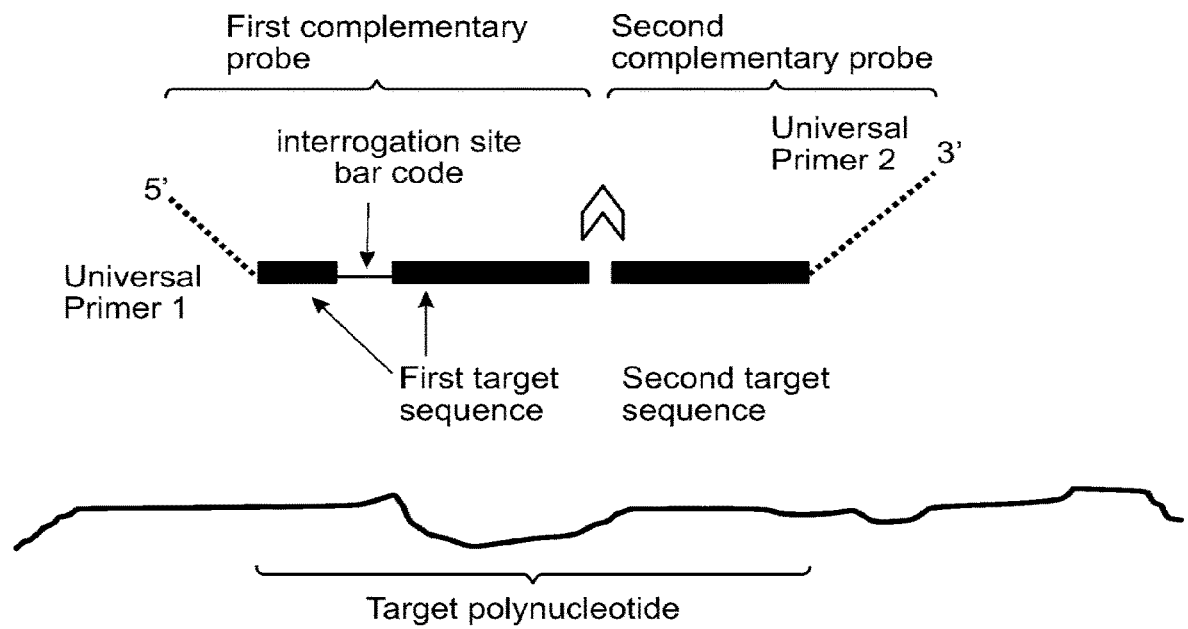
FIGS. 1A-E provide a schematic depiction of compositions and methods used in nucleic acid analysis by joining barcoded polynucleotide probes. The figures are described in detail in Example 1.

The disclosure provides compositions, methods and kits comprising a plurality of first and second complementary probes. Each first complementary probe can include a sequence that is complementary to a first target sequence of interest. Each second complementary probe can include a sequence that is complementary to a second target sequence of interest. When first and second complementary probes hybridize to complementary first and second target sequences, first and second probes can be joined to form a product polynucleotide.

The disclosure further provides a plurality of samples, each potentially comprising one or more target sequences. Some samples comprise a plurality of target sequences and some samples do not comprise any target sequences.

The disclosure provides compositions, methods and kits that can be used to determine the presence, absence, genotype, amount or copy number of at least one target polynucleotide in one or more samples.

The disclosure provides a method for determining the presence, absence, amount or copy number of one or more target polynucleotides in a sample, comprising the steps of: (a) providing a sample comprising one or more target polynucleotides, each target polynucleotide comprising a first target sequence and a second target sequence; (b) providing a plurality of first and second complementary probes comprising a first and second complementary probe for each target polynucleotide, (i) each first complementary probe having a sequence portion that is complementary to a first target sequence of the target polynucleotide, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence of the target polynucleotide and an immediately adjacent sequence portion that is non-complementary to said second target sequence; (c) incubating said plurality of first and second complementary probes with the sample under hybridization conditions such that first and second complementary probes hybridize to their complementary target polynucleotide in a sample to form a hybridization complex; (d) joining first and second complementary probes that are hybridized to first and second target sequences of a target polynucleotide in a sample to form a product polynucleotide; and (e) determining the presence, absence, amount of copy number of each target polynucleotide in the sample by analyzing product polynucleotides or the complements thereof.

The disclosure provides a method for determining the presence, absence, amount or copy number of one or more target polynucleotides in two or more samples, comprising the steps of: (a) providing two or more samples, each sample comprising one or more target polynucleotides, each target polynucleotide comprising a first target sequence and a second target sequence; (b) providing a plurality of first and second complementary probes comprising a first and second complementary probe for each target polynucleotide, (i) each first complementary probe having a sequence portion that is complementary to a first target sequence of the target polynucleotide, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence of the target polynucleotide and an immediately adjacent sequence portion that is non-complementary to said second target sequence; (c) incubating said plurality of first and second complementary probes with each sample under hybridization conditions such that first and second complementary probes hybridize to their complementary target polynucleotide in a sample to form a hybridization complex; (d) joining first and second complementary probes that are hybridized to first and second target sequences of a target polynucleotide in a sample to form a product polynucleotide; (e) pooling product polynucleotides formed from the samples; and (f) determining the presence, absence, amount of copy number of each target polynucleotide in one or more samples by analyzing product polynucleotides or the complements thereof.

The first and second target sequences of each target polynucleotide may be immediately adjacent one another. Alternatively, the first and second target sequences of each target polynucleotide may be from 1 to 500 nucleotides apart. For example, the first and second target sequences of each target polynucleotide may be at least 1, at least 2, at least 3, at least 4, at least 5 or at least 10 nucleotides apart, or the first and second target sequences of each target polynucleotide may be 2 to 10, 5 to 15, 7 to 15, 10 to 12, 15 to 25, 25 to 40, 30 to 45, 40 to 16, 60 to 65, 60 to 75, 70 to 85, 80 to 95, 90 to 120, 110 to 150, 120 to 160, 130 to 170, 150 to 190, 170 to 210, 190 to 230, 200 to 230, 220 to 260, 230 to 270, 240 to 310, 300 to 340, 330 to 370, 360 to 400, 390 to 430, 410 to 450, 440 to 480, 470 to 500 nucleotides apart.

The immediately adjacent sequence portion of said second complementary probe may comprise a universal sequence. The universal sequence of said second complementary probe may comprise a universal primer sequence that is complementary to a primer sequence which can be used to add one or more of (i) a sample index, (ii) an additional sequence, (iii) an additional sequence for sequence data generation or another form of detection, and (iv) another moiety.

The adjacent universal sequence of said first complementary probe may comprise a universal primer sequence that is complementary to a priming sequence which can be used to add one or more of (i) a sample index, (ii) an additional sequence, (iii) an additional sequence for sequence data generation or another form of detection, and (iv) another moiety.

The universal primer sequence may include a PCR primer sequence and/or a primer sequence to add an additional sequence for sequence data generation or another form of detection. The additional sequence for sequence data generation or another form of detection may be an adapter for next generation sequencing. The additional sequence for sequence data generation or another form of detection may be a capture sequence, optionally wherein the capture sequence is for capture on a solid support. The universal primer sequence may be effective to add a moiety useful for sequence generation.

The sample index may be at least 10, 11, 12, 13, 14, 15 or 16 nucleotides in length. Preferably, the sample index is 12 to 15 nucleotides in length. The sample index sequence may be selected from the group consisting of SEQ ID NO: 1-SEQ ID NO: 73536.

The universal sequences of said first and second complementary probes may each comprise a priming sequence that can hybridize to a primer for sequence synthesis. The priming sequence may include a PCR priming sequence.

The first complementary probe may comprise from 5'-3': the adjacent universal sequence, a sequence portion that is complementary to a first target sequence, and the interrogation site bar code within the sequence portion that is complementary to the first target sequence.

The first complementary probe may comprise a sequence 5' to the interrogation site bar code that is complementary to the first target sequence and a sequence 3' to the interrogation site bar code that is complementary to the first target sequence.

The first complementary probe may comprise a sequence that is complementary to the first target sequence both 3' and 5' of the interrogation site bar code.

The second complementary probe may comprise from 5'-3': a sequence portion that is complementary to a second target sequence of the target polynucleotide and an immediately adjacent sequence portion that is non-complementary to the second target sequence.

The interrogation site bar code may be at least 10, 11, 12, 13, 14, 15 or 16 nucleotides in length. Preferably, the interrogation site bar code is 12 or 15 nucleotides in length. The interrogation site bar code may be selected from the group consisting of SEQ ID NO: 1-SEQ ID NO: 384.

The methods may include a step before the incubating (or hybridizing) step that comprises reversibly denaturing the target polynucleotides. This step may be conducted by heating as described herein.

The methods may include a further step comprising enriching said product polynucleotides prior to the pooling step. The enriching step may comprise, (a) providing a set of PCR priming sequences comprising a first primer that is complementary to a priming sequence on the first complementary probe, and a second primer that is complementary to a PCR priming sequence on the second complementary probe, and (b) amplifying the product polynucleotide.

The methods may be solution-based.

The first complementary probe may comprise an inosine (e.g. deoxyinosine) 2, 3, 4, 5, 6, 7, 8, 9, 10, or more bases from the 3' end of the probe.

The second complementary probe may comprise an inosine (e.g. deoxyinosine) 2, 3, 4, 5, 6, 7, 8, 9, 10, or more bases from the 5' end of the probe.

The 3' end of the first complementary probe may be complementary to one form of a single nucleotide polymorphism (SNP) or other genetic variation.

The step of joining first and second complementary probes may comprise treating the first and the second complementary probes that are hybridized to first and second target sequences of a target polynucleotide (hybridization complex) to form a product polynucleotide using a ligase.

The methods of the disclosure may be for use in genotyping, wherein the method comprises providing one or more variants of the first complementary probe, wherein the variants differ in the identity of the nucleotide or nucleotides at the 3' end of the first complementary probe, and wherein said determining comprises quantifying the relative frequencies of product polynucleotides or complements thereof comprising the sequences of the one or more variants of the first complementary probe compared to the sequences of the other variants of said first complementary probe and correlating said frequencies with a genotype.

The methods of the disclosure may be for use in determining the copy number variation of a target polynucleotide, and wherein said determining comprises comparing the amount of signal produced for a product polynucleotide or the complement thereof to a known reference or to the amount of signal produced by another product polynucleotide or the complement thereof.

The methods of the disclosure may be for use in expression analysis in determining presence of a target polynucleotide, wherein the target polynucleotide is an RNA transcript, and wherein said determining comprises comparing the amount of signal produced for a product polynucleotide or the complement thereof to a known reference or to the amount of signal produced by another product polynucleotide or the complement thereof.

The methods of the disclosure may be for use in genotyping polyploidy samples further comprising reducing generating sequence data in non-informative polyploidy genomes comprising obtaining sample genome sequence data having target SNP/indel and proximal SNP/indel information, designing the second complementary probe so that it's hybridization to the target genome is destabilized by the proximal SNP/indel.

The methods of the disclosure may be for use in genotyping polyploidy samples further comprising reducing generating sequence data in non-informative polyploidy genomes comprising obtaining sample genome sequence data having target SNP/indel and proximal SNP/indel information, designing the second complementary probe so that it's hybridization to the target genome is destabilized by the proximal SNP/indel, and adding blocking oligos complementary to target genome having the proximal SNP/indel to further prevent hybridization of the second complementary probe to the target genome.

The methods of the disclosure may be for use in genotyping polyploidy samples further comprising reducing generating sequence data in non-informative polyploidy genomes comprising obtaining sample genome sequence data having target SNP/indel and proximal SNP/indel information, and adding an upfront PCR amplification step to select for unique genome of interest.

The disclosure provides a composition for determining the presence, absence, amount or copy number of one or more target polynucleotides in a sample, comprising a plurality of first and second complementary probes comprising a first and second complementary probe for each target polynucleotide, (i) each first complementary probe having a sequence portion that is complementary to a first target sequence of the target polynucleotide, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence of the target polynucleotide and an immediately adjacent sequence portion that is non-complementary to the second target sequence.

The disclosure provides a composition for determining the presence, absence, amount or copy number of one or more target polynucleotides in a sample, comprising a plurality of first and second complementary probes comprising a first and second complementary probe for each target polynucleotide, (i) each first complementary probe having two sequence portions that are complementary to different sections of a first target sequence of the target polynucleotide, and two sequence portions that are non-complementary to the first target sequence wherein the non-complementary portions include an interrogation site bar code sequence and a universal sequence, and (ii) each second complementary probe having a sequence portion that is complementary to a second target sequence of the target polynucleotide and an immediately adjacent sequence portion that is non-complementary to the second target sequence and includes a universal sequence.

The first and second target sequences of each target polynucleotide may be immediately adjacent one another. Alternatively, the first and second target sequences of each target polynucleotide may be from 1 to 500 nucleotides apart.

The universal sequence of the first complementary probe may comprise a universal primer sequence that is complementary to a primer sequence that allows the addition of one or more of (i) a sample index, (ii) an additional sequence, (iii) an additional sequence for use in sequence data generation or another form of detection, and (iv) another moiety.

The universal sequence of the second complementary probe may comprise a universal primer sequence that is complementary to a primer sequence that allows the addition of one or more of (i) a sample index, (ii) an additional sequence, (iii) an additional sequence for use in sequence data generation or another form of detection, and (iv) another moiety.

The universal primer sequence of the first and/or second complementary probe may include a PCR primer sequence and/or a primer sequence to add an additional sequence for sequence data generation or another form of detection. The additional sequence for sequence data generation or another form of detection may be an adapter for next generation sequencing. The additional sequence for sequence data generation or another form of detection may be a capture sequence, optionally wherein the capture sequence is for capture on a solid support. The universal primer sequence may be effective to add a moiety useful for sequence generation. The universal primer sequence may include a priming sequence that provides for the addition of a sample index.

The sample index may be at least 10, 11, 12, 13, 14, 15 or 16 nucleotides in length. Preferably, the sample index is 12 to 15 nucleotides in length. The sample index sequence may be selected from the group consisting of SEQ ID NO: 1-SEQ ID NO: 73536.

The universal sequence of said first and second complementary probes may each comprise a priming sequence that can hybridize to a primer for sequence synthesis. The priming sequence may include a PCR priming sequence.

The first complementary probe may comprise from 5'-3': the adjacent universal sequence, the sequence portion that is complementary to the first target sequence, and the interrogation site bar code within the sequence portion that is complementary to the first target sequence.

The first complementary probe may comprise a sequence 5' to the interrogation site bar code that is complementary to the first target sequence and a sequence 3' to the interrogation site bar code that is complementary to the first target sequence.

The first complementary probe may comprise a sequence that is complementary to the first target sequence both 3' and 5' of the interrogation site bar code.

The second complementary probe may comprise from 5'-3': a sequence portion that is complementary to a second target sequence of the target polynucleotide and an immediately adjacent sequence portion that is non-complementary to the second target sequence.

The interrogation site bar code may be at least 10, 11, 12, 13, 14, 15 or 16 nucleotides in length. Preferably, the interrogation site bar code is 12 or 15 nucleotides in length. The interrogation site bar code may be selected from the group consisting of SEQ ID NO: 1-SEQ ID NO: 384.

The first complementary probe may comprise an inosine (e.g. deoxyinosine) 2, 3, 4, 5, 6, 7, 8, 9, 10, or more bases from the 3' end of the probe.

The second complementary probe may comprise an inosine (e.g. deoxyinosine) 2, 3, 4, 5, 6, 7, 8, 9, 10, or more bases from the 5' end of the probe.

The 3' end of the first complementary probe may be complementary to one form of a single nucleotide polymorphism (SNP) or other genetic variation.

The disclosure provides a kit for determining the presence, absence, amount, copy number or characteristics of one or more target polynucleotides in a sample comprising: (a) a plurality of first and second complementary probes as disclosed herein; and (b) optionally, buffers and enzymes for ligation and enrichment.

The disclosure provides a kit for determining the presence, absence, amount, copy number or characteristics of one or more target polynucleotides in a sample comprising: (a) a plurality of first and second complementary probes comprising a first and second complementary probe for each target polynucleotide, (i) each first complementary probe having a sequence portion that is complementary to a first target sequence of the target polynucleotide, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence of the target polynucleotide and an immediately adjacent sequence portion that is non-complementary to said second target sequence; and (b) optionally, buffers and enzymes for ligation and enrichment.

The disclosure provides a kit for determining the presence, absence, amount, copy number or characteristics of one or more target polynucleotides in a sample comprising: (a) a plurality of first and second complementary probes comprising a first and second complementary probe for each target polynucleotide, (i) each first complementary probe having two sequence portions that are complementary to different sections of a first target sequence of the target polynucleotide, and two sequence portions that are non-complementary to the first target sequence wherein the non-complementary portions include an interrogation site bar code sequence and an adjacent universal sequence, and (ii) each second complementary probe having a sequence portion that is complementary to a second target sequence of the target polynucleotide and an immediately adjacent sequence portion that is non-complementary to said second target sequence; and (b) optionally, buffers and enzymes for ligation and enrichment.

The kit may further comprise at least one PCR primer, a polymerase, and/or a set of dNTPs to amplify extended target polynucleotides for purposes of enrichment.

The kit may further comprise a ligase.

The kit may further comprise software needed to interpret the data.

The kit may be for determining a genotype and/or the kit may be for determining copy number and/or the kit may be for determining expression of an RNA transcript.

Definitions

Unless defined otherwise, all technical and scientific terms used herein have the same meaning as commonly understood by one of ordinary skill in the art to which the invention pertains.

It is to be understood that the disclosure of the invention in this specification includes all possible combinations of such particular features. For example, where a particular feature is disclosed in the context of a particular aspect or a particular embodiment, that feature can also be used in combination with other particular aspects and embodiments and in the invention generally, except where the context excludes that possibility. The invention disclosed herein includes embodiments not specifically described and can for example make use of features which are not specifically disclosed herein, but which provide functions which are the same, equivalent or similar to, features specifically disclosed herein.

In describing and claiming the present invention, the following terminology will be used in accordance with the definitions set out below.

As used in this specification and the appended claims, the singular forms "a," "an" and "the" include plural referents unless the context clearly dictates otherwise. Thus, for example, reference to "a target polynucleotide" includes two or more such target polynucleotides, and reference to "a probe" includes two or more probes, or mixtures of probes, and the like.

The term "adjacent", as used herein means that two sequences substantially next to one another on a nucleic acid, however there may be one or more intervening bases between two adjacent sequences.

The term "immediately adjacent", as used herein means that two sequences are next to one another on a nucleic acid with no intervening bases between the immediately adjacent sequences.

The term "allele" as used herein means one of two or more alternative forms of a gene or genetic locus. If a diploid organism has two copies of the same allele, for example, AA or aa, it is homozygous at that location. If the organism has one copy of two different alleles, for example Aa, it is heterozygous at that location. Alternative nomenclature uses A and B for the alleles. A homozygous diploid organism is AA or BB at that location. A heterozygous diploid organism is AB at that location. The term allele also applies to situations where there are three or more possible alternative forms, and can be extended as known in the art, e.g., with respect to alleles A, B, and C for a triallelic single nucleotide polymorphism.

The term "array" as used herein means an intentionally created collection of molecules which can be prepared either synthetically or biosynthetically. An array can assume a variety of forms, such as libraries of soluble molecules and the utilization of one or more solid supports, such as glass slides, silica chips, microparticles, nanoparticles, or beads. As referred to herein, a "solid support" is any material that can be attached to a probe, target nucleotide or product nucleotide, for example, glass and modified or functionalized glass, plastics, polysaccharides, nylon, nitrocellulose, ceramics, resins, silica-based materials, carbon, metals, inorganic materials, and other polymers, for example a flow cell or another solid surface such as a bead or microarray.

The term "at least" followed by a number is used herein to denote the start of a range beginning with that number (which may be a range having an upper limit or no upper limit, depending on the variable being defined). "at most" followed by a number is used herein to denote the end of a range ending with that number (which may be a range having 1 or 0 as its lower limit or a range having no lower limit, depending upon the variable being defined). When a range is given as "(a first number) to (a second number)" or "(a first number)-(a second number)", this means a range whose lower limit is the first number and whose upper limit is the second number. The terms "plural", "multiple", "plurality" and "multiplicity" are used herein to denote two or more than two features.

The terms "bar code" or "barcode" or "index" are used interchangeably herein with reference to a nucleotide sequence used to identify or "tag" one or more particular target or product polynucleotides. A "bar code" is typically at least 5 nucleotides (nt) in length. In some embodiments, a bar code or a portion thereof may occur in a first and/or second complementary probe. As used herein, a bar code can be used as a sample bar code or an interrogation site bar code. In some embodiments, the same bar code sequence is in two different places on a polynucleotide and is used as a sample index bar code in one place and an interrogation site bar code in the other place. In some embodiments, different bar code sequences (that may also be of the same or different lengths) are in two different places on a polynucleotide, and are used as a sample bar code in one place and an interrogation site bar code in the other place. A bar code may have the same sequence present in the target polynucleotide or its complement, it may be a sequence that is partially complementary to sequence in the target polynucleotide or its complement, and it may be a sequence that has no complementarity to the target polynucleotide or its complement or may be any combination of these states. In some embodiments, a single sequence serves as both an interrogation site bar code and a sample index. In some embodiments, a single sequence has a portion that serves as an interrogation site barcode and a portion that serves as a sample index.

The term "base" means a nitrogen-containing heterocyclic moiety capable of forming Watson-Crick type hydrogen bonds with a complementary nucleotide base or nucleotide base analog, e.g. a purine, a 7-deazapurine, or a pyrimidine. Typical bases are the naturally occurring bases adenine, cytosine, guanine, thymine, and uracil. Bases also include analogs of naturally occurring bases and universal bases such as inosine, 3-nitropyrrole and 5-nitroindole. Any universal base (one that does not favor particular base-pairing) can be used in practicing the invention.

The term "base modifications" is used herein with reference to polynucleotides that comprise non-standard bases (i.e., other than adenine, guanine, thymine, cytosine and uracil). Such non-standard bases may serve a number of purposes, e.g., to stabilize or destabilize hybridization; to promote or inhibit degradation; or as attachment points for detectable moieties, quencher moieties or other moieties. Numerous examples of modified bases (other than the modified bases of the invention) and base analogs are known in the art.

The term "complementary polynucleotides" is used herein with reference to polynucleotides that form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes, including the wobble base pair formed between U and G. As persons skilled in the art are aware, when using RNA as opposed to DNA, uracil rather than thymine is the base that is considered to be complementary to adenine. In determining the degree of complementarity between a probe and a target gene, the degree of "complementarity" is expressed as the percentage identity between the sequence of the probe and the sequence of the target gene or the complement of the sequence of the target gene that best aligns therewith. In certain embodiments, the degree of "complementarity" between the sequence of the probe and the sequence of the target gene or the complement of the sequence of the target gene does not need to be 100 percent identical. In one embodiment, the degree of "complementarity" is less than 100 percent but sufficient to allow hybridization between the sequence of the probe and the sequence of the target gene or the complement of the sequence of the target gene under certain conditions.

The term "complementary" is used herein with reference to polynucleotides or sequences which when aligned antiparallel to another sequence, have nucleotide bases at substantially all the positions in the sequences that are complementary and no sequence portions with four or more immediately adjacent non-complementary bases.

The term "comprises" and grammatical equivalents thereof are used herein to mean that, in addition to the features specifically identified, other features are optionally present. For example, a composition or device "comprising" (or "which comprises") components A, B and C can contain only components A, B and C, or can contain not only components A, B and C but also one or more other components. The terms "consisting essentially of" and grammatical equivalents thereof are used herein to mean that, in addition to the features specifically identified, other features may be present which do not materially alter the claimed invention.

The term "contacting" may be used herein with reference to the combination of two sequences under conditions that allow them to hybridize to one another if they are sufficiently complementary. For example, contacting first and second complementary probes with a sample under conditions that permit the probes to hybridize to the target polynucleotide sequence in the sample if they are sufficiently complementary.

The term "copy number variation" ("CNV") as used herein means an alteration of portions of the DNA of a genome that results in the cell having a variation in the number of copies of one or more sections of the DNA. CNVs typically correspond to relatively large regions of the genome that have been deleted (fewer than the normal number) or duplicated (more than the normal number) on certain chromosomes.

The term "corresponds to" or "corresponding to" may be used herein to refer to a sequence that is homologous, or substantially equivalent, or functionally equivalent to the designated sequence.

The term "determining" as used herein means to conclude or ascertain, after reasoning, observation, and the like.

The term "DNA polymorphism" is used herein with reference to a condition in which one of two different, nucleotide sequences can exist at a particular site in DNA. Preferred polymorphic markers have at least two alleles, each occurring at frequency of greater than 1%, 2%, 3%, 4%, 5%, 6%, 7% or more. In some cases, an allele occurs at frequency of greater than 10%, 15%, or 20% of a selected population. A polymorphic locus may be as small as one base pair. A single nucleotide polymorphism (SNP) may be a substitution of one nucleotide for another at the polymorphic site. Single nucleotide polymorphisms may also be a deletion of a nucleotide or an insertion of a nucleotide at the polymorphic site. A biallelic polymorphism has two forms. A triallelic polymorphism has three forms. A single nucleotide polymorphism occurs at a polymorphic site occupied by a single nucleotide, which is the site of variation between allelic sequences. As will be understood by those of skill in the art, SNPs are often polymorphisms that include more nucleotides than a single base. Other polymorphisms include (small) deletions or insertions of several nucleotides, referred to as indels. "DNA polymorphism" may be used with reference to structural rearrangements, translocations, large insertions or deletions, inversions, etc., and may also include the addition of genetic material (which may or may not be derived from the host) into the genome.

The term "duplex" is used herein with reference to a double-stranded nucleic acid molecule formed by annealing complementary (or partially complementary) single-stranded nucleic acid molecules, e.g., DNA, RNA, PNA to one another.

The term "first complementary probe" is used herein with reference to a polynucleotide comprising a first sequence that is at least partially complementary to a first target sequence of a target polynucleotide. The first complementary probe may further comprise an interrogation site bar code, which may be allele-specific, locus specific, or allele and locus specific (combined) or allele and locus specific in different sequences, and/or a universal sequence (which may include a primer binding sequence), and the like. In some embodiments, the first complementary probe may further comprise a priming sequence for generation of a sample index. In some embodiments, the first complementary probe has a 5' hydroxylated nucleotide.

The term "first target sequence" refers to a portion of a target polynucleotide that is a target for hybridization. The first target sequence may or may not be present in a sample.

The term "genetic locus" is used herein with reference to a specific location or position of a gene, a base, or any significant sequence on a chromosome or other type of nucleic acid.

The term "genotype" is used herein with reference to the genetic makeup of an organism. It is used in reference to single sites, multiple sites, sites with two or more alleles, variations in copy number or structure or monomorphic sites.

The term "gap filling" is used herein when first and second complementary probes hybridize to a target sequence in a manner that they are not adjacent one another. When first and second complementary probes hybridize to first and second target sequences, there may or may not be a gap between the first and second complementary probes. The "gap" may be 1, 2 to 10, 5 to 15, 7 to 15, 10 to 12, 15 to 25, 25 to 40, 30 to 45, 40 to 16, 60 to 65, 60 to 75, 70 to 85, 80 to 95, 90 to 120, 110 to 150, 120 to 160, 130 to 170, 150 to 190, 170 to 210, 190 to 230, 200 to 230, 220 to 260, 230 to 270, 240 to 310, 300 to 340, 330 to 370, 360 to 400, 390 to 430, 410 to 450, 440 to 480, 470 to 500, 2, 3, 4, 5, 10, 20, 30, 40, 50, 60, 70, 80, 90, 100, 120, 140, 160, 180, 200, 220, 240, 260, 280, 300, 320, 340, 360, 380, 400, 420, 440, 460, 480, 500 or more nucleotides. In some cases, the gap may be filled by extension of one end of the first or second probe using a polymerase and a ligase in combination with single or multiple nucleotides. In cases where the target polynucleotide is RNA, the gap may be filled by extension of one end of the first or second complementary probes, e.g., using a reverse transcriptase and a ligase.

The term "hybridize" or "hybridization" is used herein with reference to the binding, duplexing, or annealing of a nucleic acid molecule preferentially to a particular target polynucleotide, typically, under stringent conditions. The term "stringent conditions" refers to conditions under which a probe will hybridize preferentially to its target polynucleotide, and to a lesser extent to, or not at all to, other sequences. The term "stringent hybridization" as used in the context of nucleic acid hybridization is sequence-dependent and is different under different environmental parameters. The dependency of hybridization stringency on buffer composition, temperature, and probe length are well known to those of skill in the art (see, e.g., Sambrook and Russell (2001) Molecular Cloning: A Laboratory Manual (3rd ed.) Vol. 1-3, Cold Spring Harbor Laboratory, Cold Spring Harbor Press, NY). The degree of hybridization of a nucleotide sequence to a target sequence, also known as hybridization strength, is determined by methods that are well-known in the art. A preferred method is to determine the $T_m$ of a given hybrid duplex.

The term "interrogation site" is used herein with reference to the location in a nucleic acid that is being evaluated, for example a SNP at a particular genetic locus that is being evaluated for presence or absence or amount. In other embodiments where genetic variation is not being evaluated, rather the presence or absence or amount of a genetic locus is being evaluated. In other embodiments the base composition at the location in a nucleic acid is being evaluated.

The term "interrogation site bar code", is used herein with reference to a bar code the function of which is to identify a particular target polynucleotide and/or a variant thereof. An interrogation site bar code may be allele-specific, locus-specific, allele and locus specific, or allele and locus specific.

The term "label" refers to a moiety that, when directly or indirectly attached to a nucleotide or oligonucleotide, renders such nucleotide or oligonucleotide detectable by suitable detection means. Exemplary labels include bar codes, fluorophores, chromophores, radioisotopes, spin-labels, enzyme labels, chemiluminescent labels, electrochemiluminescent compounds, magnetic labels, microspheres, colloidal metal, immunologic labels, ligands, enzymes, and the like.

The term "locus" as used herein means the position that a given gene or genetic sequence occupies on a chromosome or other nucleic acid structure. The locus may be a sequence that is outside of a gene. Examples of other nucleic acid structures include, but are not limited to all types of RNA (messenger, long non-coding, small, ribosomal, etc.). All types of DNA are also included, such as, but not limited to plasmids, chromosomes, BACs, YACs, cosmids, mitochondrial, chloroplast and plastid DNA, cDNA and any other naturally occurring or human created structure.

The term "mismatched nucleotide" is used herein with reference to a nucleotide in a target polynucleotide that is not complementary to the corresponding nucleotide in a corresponding probe or primer sequence when the sequences are hybridized to one another. The complement of C is G and the complement of A is T. In other words, a "C" in a probe is considered to be mismatched with a "T" in a target polynucleotide.

As used herein, the term, a "modified polynucleotide" may be used to refer to a nucleotide sequence comprising a universal base, for example, deoxyinosine (also referred to herein as "inosine"), 3-nitropyrrole, or 5-nitroindole.

The term "next generation sequencing" or "NGS" is used herein with reference to high-throughput sequencing. NGS may also refer to third, fourth and additional generations of sequence data generation that are not high throughput but have other properties that distinguish them from traditional Sanger sequencing.

As used herein, "nucleic acid" refers to a natural, synthetic, or artificial polynucleotide, such as DNA or RNA, which embodies a sequence of nucleotides. The nucleic acid can be fragmented, cloned, replicated, amplified, or otherwise derived or manipulated. Exemplary DNA species include genomic DNA (gDNA), mitochondrial DNA, and complementary DNA (cDNA). Exemplary RNA species include messenger RNA (mRNA), transfer RNA (tRNA), microRNA (miRNA), small interfering RNA (siRNA), and ribosomal RNA (rRNA).

As used herein, "nucleic acid amplification" or "amplification" is used with reference to any means by which at least a part of at least one target nucleic acid is reproduced, typically in a template-dependent manner, including without limitation, a broad range of techniques for amplifying nucleic acid sequences, either linearly or exponentially. Non-limiting exemplary amplification methods include polymerase chain reaction (PCR), reverse-transcriptase PCR, real-time PCR, nested PCR, multiplex PCR, quantitative PCR (Q-PCR), nucleic acid sequence based amplification (NASBA), transcription mediated amplification (TMA), ligase chain reaction (LCR), rolling circle amplification (RCA), strand displacement amplification (SDA), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); The Nucleic Acid Protocols Handbook, R. Rapley, ed., Humana Press, Totowa, N.J. (2002); and Innis et al, PCR Protocols: A Guide to Methods and Applications, Academic Press (1990).

As used herein, "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

The terms "polynucleotide" and "oligonucleotide" may be used interchangeably herein, and refer to linear polymers of nucleotide monomers or of modified forms thereof, including for example, double- and single-stranded deoxyribonucleotides, ribonucleotides, and the like. A polynucleotide may be composed entirely of deoxy-ribonucleotides, ribonucleotides or analogs thereof, or may contain blocks or mixtures of two or more different monomer types. Whenever a polynucleotide is represented by a sequence of letters, such as "ATGCCTG," it will be understood that the nucleotides are in 5'→3' order from left to right (unless otherwise indicated) and that "A" denotes adenosine, "C" denotes cytidine, "G" denotes guanosine, "T" denotes thymidine, and "U" denotes uridine, unless otherwise noted. When used alone, "polynucleotide" and "oligonucleotide" refer to sequences composed primarily or entirely of conventional DNA or RNA monomer units—i.e., of deoxyribose or ribose sugar rings substituted with A, C, G, T or U bases and which are linked by conventional phosphate backbone moieties. Polynucleotides usually comprise or consist of a single-stranded polynucleotide having fewer than 100 nucleotides, although longer sequences of hundreds or thousands or more bases are also contemplated. In some embodiments, a polynucleotide comprises, or consists of, 2 to 100, 2 to 50, 2 to 25, 2 to 15, 5 to 50, 5 to 25, 5 to 15, 10 to 50, 10 to 25, 10 to 20, 10 to 15, 12 to 50, 12 to 25 or 12 to 20 nucleotides. Polynucleotides may be referred to by their length. For example, a 15 nucleotide long sequence may be referred to as a "15-mer."

A "primer' or "probe" is typically a nucleotide sequence that comprises a region that is complementary to a sequence of at least 6 contiguous nucleotides of a target nucleic acid, although primers and probes can comprise fewer than 6 contiguous nucleotides. In some embodiments, a polynucleotide primer or probe is provided that comprises a sequence that is identical to, or complementary to 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 60 or more, 70 or more, 80 or more, 90 or more or up to 100 contiguous nucleotides of a target polynucleotide. When a primer or probe comprises a region that is "perfectly complementary" to a number of contiguous nucleotides of a target molecule, the primer or probe may be referred to as 100% complementary to the target molecule when there are no mismatches along the length.

When a "probe" forms a duplex with a target polynucleotide, a signal may be generated directly or indirectly, during or after probe hybridization.

The term "product polynucleotide" is used herein with reference to a polynucleotide formed when first and a second complementary probes, complementary to first and second target sequences of a target polynucleotide (with or without a gap between the target sequences), are joined (e.g. by ligation) to form a single "product" polynucleotide.

The term "sample index bar code" or "sample index" is used herein as an identifier sequence that is used to designate a particular sample and to track information related to that sample, even when the sample (or a reaction product thereof or lack of a reaction product thereof) is mixed with other samples (and/or reaction products thereof or lack of a reaction product thereof).

The term "first or second complementary probe" is used herein with reference to a polynucleotide comprising a first or second sequence that is complementary to a first or second target sequence of a target polynucleotide. In some embodiments, the first or second complementary probe may further comprise a priming sequence for generation of a sample index. In some embodiments, the universal sequence in the first and second complementary probes may be the same or different. In some embodiments, the first or second complementary probe has a 5' phosphorylated nucleotide.

The term "first or second target sequence" refers to a portion of a target polynucleotide that is a target for hybridization. In certain embodiments, the first or second target sequence may or may not be present in a sample.

The term "sequencing" is used herein with reference to DNA sequencing or the process of determining the order of nucleotides within a DNA molecule. It includes any method or technology that can be used to determine the order of adenine, guanine, cytosine, and thymine in a strand of DNA. Sequencing may also include RNA sequencing where the order of the bases in RNA are determined.

The term "single nucleotide polymorphism" or "snp" or "SNP" is used herein with reference to a nucleic acid sequence variation occurring commonly within a population in which typically a single nucleotide A, T, C or G differs between paired chromosomes. Most common SNPs have two alleles, however they may have more than two alleles. SNPs may also occur on RNA molecules. In RNA molecules SNPs may reflect differences in RNA processing.

The term "target polynucleotide" is used herein with reference to a sequence in a nucleic acid or polynucleotide that is a target for hybridization. The target polynucleotide may or may not be present in a sample. In some embodiments, the target polynucleotide comprises RNA or DNA that is partially or fully complementary to a first complementary probe and second complementary probe of the invention. The target polynucleotide can usually be described using the four bases of DNA (A, T, G, and C) or the four bases of RNA (A, U, G, and C).

The term "target sequence" refers to a portion of a target polynucleotide that is a target for hybridization. The target sequence may be a first or second target sequence and may or may not be present in a sample. As will be understood by those of skill in the art, reference to a "target sequence" may also mean the complement of the target sequence.

The term "thermal melting point" or "Tm" is used herein with reference to a specific sequence at a defined ionic strength and pH. The Tm is the temperature at which 50% of the target sequence hybridizes to a perfectly matched probe. Tm is also defined as the temperature at which half of the DNA strands are in the single-stranded (ssDNA) state. Tm depends on various parameters such as the length of the hybridized complementary strand sequence, their specific nucleotide sequences, base compositions, and the concentrations of the complementary strands and other conditions of the solution.

The term "universal base" is used herein with reference to bases that can aid in preventing, or decreasing the frequency of joining of molecules when the 3' end of a first complementary probe is not complementary to a target polymorphic nucleotide or nucleotides. Inosine, 3-nitropyrrole, and 5-nitroindole are examples of universal bases.

The term "universal sequence" is used herein with reference to a sequence component of a first or second complementary probe which may include a universal priming sequence.

The term "universal primer sequence" or "universal primer binding sequence" comprises a primer sequence that is complementary to a primer sequence such as a PCR primer sequence, and is used to add one or more of (i) a sample index, (ii) additional sequences, (iii) a sequence or sequences for use in sequence data generation or other forms of detection, and (iv) other moieties. As will be understood by those of skill in the art, the term "universal primer sequence" or "universal primer binding sequence" may be used with reference to a primer sequence or its complement.

PCR primer sequences are typically used in pairs and the composition of the two components in the pair may not be identical. Any two pairs of PCR primer sequences may have identical sequence except for the sample index. In some embodiments, the sequence of primer #1 in both a first and second pair is identical and the sequence of primer #2 is different from the sequence of primer #1 and the sequence of primer #2 in the first and second pair is identical except for a sample index. In some embodiments, the PCR primers contain a universal sequence or sequences, and/or a sample index or indices and/or a sequence moiety or moieties with other functions. A PCR reaction with universal primer sequence(s) can be used to add a sample index. The universal primer sequence in the first complementary probe and its complementary portion in the first PCR primer may or may not be the same length or have a 100% complementary sequence. The universal primer sequence in the second complementary probe and its complementary portion in the second PCR primer may or may not be the same length or have 100% complementary sequence. A universal primer sequence can be used to add adapter sequences for binding to a solid support. In some cases, the binding to a solid support is for purposes of next generation sequencing. In other cases, the binding to a solid support is for array based detection of the product polynucleotide. In some cases, a universal primer sequence is used to add sequences or moieties for other forms of detection or sequence data generation.

As used herein the terms "PCR primer" or "PCR priming sequence" may or may not mean the same thing as a "universal priming sequence". As will be understood by those of skill in the art, the term "PCR primer" or "PCR priming sequence" may be used with reference to a PCR primer or its complement.

This specification incorporates by reference in their entirety all documents referred to herein and all documents filed concurrently with this specification or filed previously in connection with this application, including but not limited to such documents which are open to public inspection with this specification.

Compositions and Methods

Improved compositions and methods for determining the presence, absence, amount, copy number or characteristics of one or more target polynucleotides in a sample or a plurality of samples are provided. The target polynucleotides can be regarding a polymorphism such as a substitution, deletion, insertion, copy number variation, translocation, nucleotide modification (such as methylation), or any other change in the target polynucleotide or status thereof.

The methods of the invention may be used for identifying the presence, absence, copy number or amount (or combination thereof) of a large number of target polynucleotides in one or more samples in a solution-based hybridization assay.

In some embodiments, a plurality of samples (e.g., 2-50, 000) is provided which may or may not contain one or more different target polynucleotides. A plurality of first and second complementary probes, each comprising a sequence complementary to a target sequence of interest may be incubated with one or more samples under conditions that allow first and second complementary probe sequences to hybridize to complementary first target sequence and second target sequences. Exemplary first and second complementary probe sequences are from about 50 to 200 nucleotides in length. In some embodiments, the first target sequence is on the left side of an interrogation site or polymorphic nucleotide. In some embodiments, the methods may be used to identify polymorphisms, for example single or multi-nucleotide polymorphisms, deletions, insertions, translocations, covalent nucleotide modifications, etc.

In certain embodiments, the methods can be used to determine the presence or absence or amount of a specific target polynucleotide, for example to determine the presence or absence or amount of a pathogen or cancer-related sequence in a sample, e.g., a biological sample.

In certain exemplary methods for identifying the presence or absence of a target polynucleotide in a sample, a plurality of first and second complementary probes are incubated with one or more samples that may or may not contain a polymorphism in a target polynucleotide sequence under conditions that provide for hybridization of complementary sequences.

In certain embodiments, if a first and second complementary polynucleotide probe hybridize to a target polynucleotide sequence adjacent one another, the complementary probes can be joined together to form a product polynucleotide.

In one embodiment, there is a polymorphic nucleotide at the 3' end of the first complementary probe. In an example of this embodiment, the polymorphic nucleotide is a SNP and two versions of an allele are represented by two different first complementary probes which are the same with the exception of the 3' nucleotide. (See FIG. 1E).

In certain embodiments, if a target polynucleotide of interest is not present in a particular sample or if a polymorphic nucleotide or allele that is targeted by the first or second probe is not present in the sample, the first and second probe will not hybridize to a nucleotide sequence in the sample, and a product polynucleotide will not form, corresponding to a determination that the target polynucleotide of interest is absent in the sample.

In one example, both the first complementary probe and the second complementary probe comprise a target complementary sequence and the first complementary probe also comprises a 3' terminal nucleotide that is complementary to the polymorphic nucleotide on the target polynucleotide. See FIG. 1E.

In another example, both the first complementary probe and the second complementary probe comprise a target complementary sequence and the second complementary probe also comprises a 5' terminal nucleotide that is complementary to the polymorphic nucleotide on the target polynucleotide.

Figure 8:
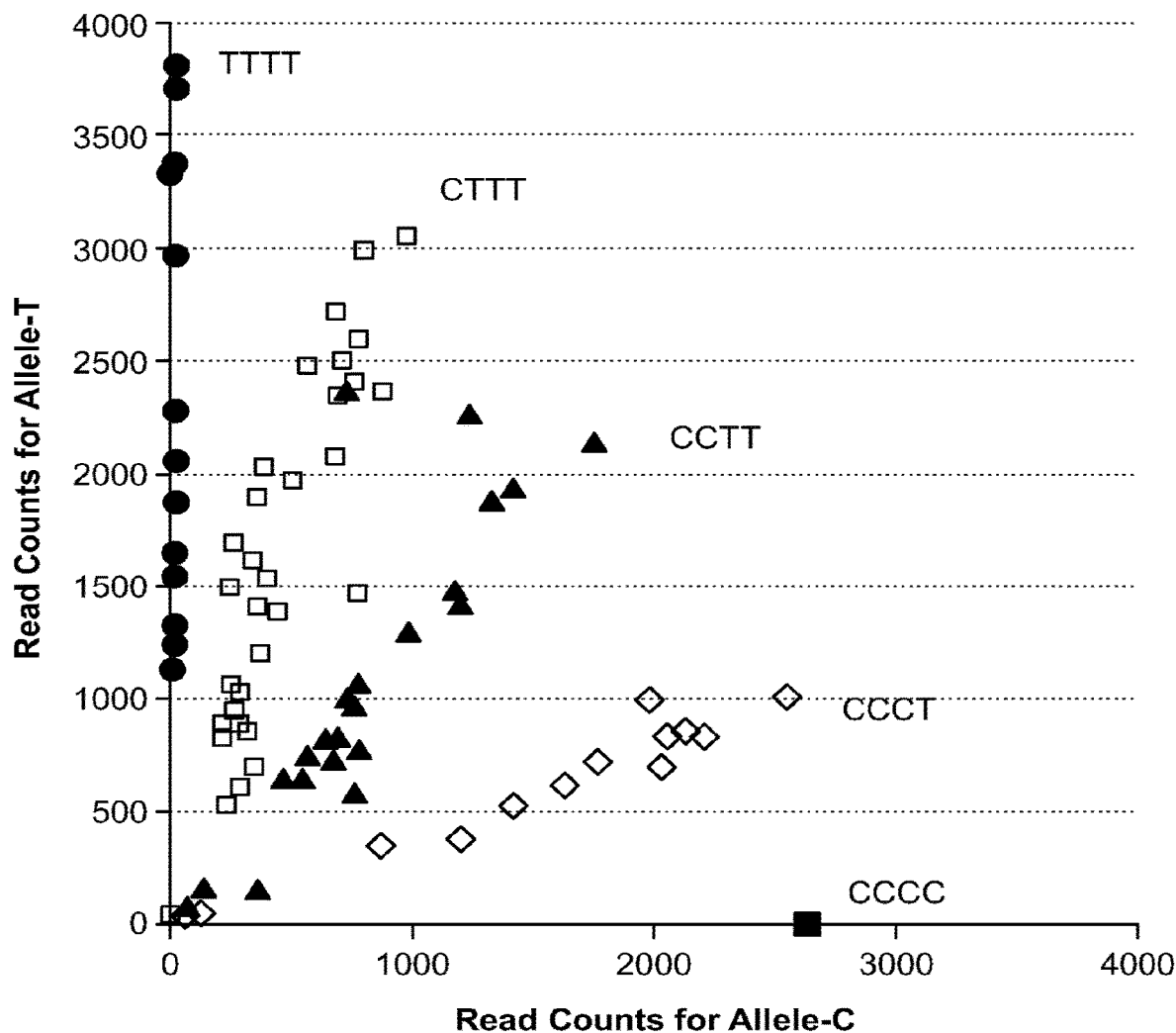
FIG. 8 illustrates the use of a tetraploid genotyping embodiment in detection and genotyping of tetraploid genomic DNA. The figure shows a cluster plot of a single locus in a mock tetraploid genomic DNA sample. Number of reads for Allele-A (x-axis) and Allele-B (y-axis) and Allele-C (z-axis) are shown, where each point is a unique sample. In this case the allele A is the C base and allele B is the T base. Homozygous animals with TTTT (solid circle) or CCCC (solid square) genotypes plot along the Y or X axis, respectively. Heterozygous animals are shown as open squares, closed triangle, and open diamonds.

FIG. 8 depicts a variation of the methods used to determine the presence or absence of a target polynucleotide, derived from a tetraploid organism, which comprise two copies (alleles) for each target polynucleotide. Either strand of a given polymorphic locus can be analyzed for the polymorphism.

In another example, a plurality of first complementary probes is provided, wherein the probes correspond to a number of possible polymorphisms, polymorphic nucleotides, or alleles at a given locus. In examples wherein a single base (substitution, insertion or deletion) is interrogated, there can be nine first complementary probes for a given locus, and multi-nucleotide polymorphisms can have more than nine first complementary probes for a given locus. In some cases, there is a single second complementary probe for a given locus.

Preferably, there are at least 2 different first complementary probes for each target polynucleotide. For example, there may be at least 3, at least 4, at least 5, at least 6, at least 7, at least 8, at least 9 or at least 10 different first complementary probes for each target polynucleotide. Preferably, there is 1 second complementary probe for each target polynucleotide. However, there may be at least 2 different second complementary probes for each target polynucleotide. For example, there may be at least 3, at least 4, at least 5, at least 6, at least 7, at least 8, at least 9 or at least 10 different second complementary probes for each target polynucleotide. Each different first and/or second complementary probe may be specific for a particular allele.

In some embodiments, a probe comprises a detectable label or moiety. In some embodiments, a probe is not labeled, such as when a probe is a capture probe, for example when the probe is used for capture on a solid surface such as a microarray or bead. In some embodiments, the label is a bar code. In some embodiments, a probe is not extendable, e.g., by a polymerase. In some embodiments, a probe is extendable.

Samples

In some embodiments, the amount of DNA or RNA in a sample for use in the methods of the invention is less than 100 µg, less than 80 µg, less than 60 µg, less than 40 µg, less than 20 µg, less than 10 µg, less than 5 µg, less than 4 µg, less than 3 µg, less than 2 µg, less than 1 µg, less than 500 ng, less than 400 ng, less than 300 ng, less than 200 ng, less than 100 ng, less than 50 ng, less than 40 ng, less than 30 ng, less than 20 ng, less than 10 ng, less than 5 ng, less than 1 ng, less than 0.1 ng, less than 0.01 ng, from 0.01 ng to 1000 ng, from 5 ng to 500 ng, from 5 ng to 250 ng, from 10 ng to 125 ng, from 10 ng to 100 ng, from 5 ng to 50 ng, or from 5 ng to 25 ng.

A sample can be derived from any animal, plant, microbial, viral, synthetic DNA or synthetic RNA source. A "plurality of samples" refers to two or more samples, from the same or different sources. For example, each sample may be derived from a different animal or a different plant, or the samples may be from different microbial sources. In some exemplary embodiments, a plurality is 2, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more, for example from 2 to 10,000 samples, from 2 to 20 samples, from 5 to 30 samples, from 10 to 50 samples, from 25 to 75 samples, from 40 to 100 samples from 50 to 120 samples, from 60 to 130 samples, from 70 to 140 samples, from 80 to 150 samples, from 90 to 170 samples, from 100 to 200 samples, from 150 to 250 samples, from 200 to 300 samples, from 250 to 500 samples, from 300 to 700 samples, from 400 to 1000 samples, from 500 to 1500 samples, from 600 to 2000 samples, from 700 to 3000 samples, from 800 to 4000 samples, from 900 to 5000 samples, from 50 to 1000 samples, from 100 to 1000 samples, from 200 to 2000 samples, from 300 to 3000 samples, from 400 to 4000 samples, from 500 to 5000 samples, from 600 to 6000 samples, from 700 to 7000 samples, from 800 to 8000 samples, from 9 to 9000 samples, or from 1000 to 100,000 samples.

DNA or RNA may be isolated from any source, for example biological sources such as blood or another tissue, biological fluids, hair, nasal swabs, germplasm, plant material, etc. Essentially any source of nucleic acid may be used. In some embodiments, a sample may contain contaminants or inhibitors that prevent the method from working such as salts or other components that serve as PCR inhibitors. In such cases, the sample may be extracted or purified in another way to reduce or eliminate the inhibiting component.

In some variations, polynucleotides can be isolated from samples using a variety of methods, for example mechanical isolation (such as glass-bead technology), chemical extraction methods, column based methods, or combinations thereof. Any DNA extraction method, a large number of which are well-known to one of skill in the art, may be used in the methods described herein.

The DNA in a nucleic acid sample may be double stranded, single stranded or double stranded DNA denatured into single stranded DNA. Denaturation of double stranded sequences provides two single stranded sequences one or both of which can be assayed using probes specific for the respective strands (in separate reactions). Preferred nucleic acid samples comprise target polynucleotides of genomic DNA, on cDNA, DNA fragments, e.g., restriction fragments, and the like.

Prior to combination with a complementary probe set, the sample may be treated to fragment the nucleic acid. This may occur by one or more of the following methods: physical fragmentation using for example, sonication; shearing such as acoustic shearing; needle shearing; point-sink shearing; nebulization; passage through a pressure cell; or heating; enzymatic fragmentation using for example, DNase I, another restriction endonuclease, a non-specific nuclease or a transposase; or chemical fragmentation, e.g., using heat and divalent metal cations.

Prior to the incubating (or hybridization) step, the one or more target polynucleotides in the one or more samples may be reversibly denatured. This may, for example, be achieved by a heating step e.g. heating to at least 70° C., 70° C. to 100° C., 75° C. to 100° C., 80° C. to 98° C., 85° C. to 95° C., 90° C. to 100° C. or 95° C. to 100° C. Preferably, the heating step is 95° C. to 100° C. The heating step may be performed for at least 30 seconds, at least 1 minute, 1-30 minutes, 2-25 minutes, 3-20 minutes, 4-15 minutes or 5-10 minutes. Preferably, the heating step is performed for 1-15 minutes.

In some embodiments, after combination with the complementary probes the nucleic acid in the samples is reversibly denatured. Double stranded DNA can be denatured into single stranded DNA, for example, heating to about 98° C. for about one minute.

Double stranded DNA is denatured into single stranded DNA using standard conditions known to those of skill in the art, for example, heating to about 98° C. for about five minutes. In practicing the methods disclosed herein, samples or samples plus first and second complementary probes may be heated to a temperature of from 70° C. to 100° C., 75° C. to 100° C., 80° C. to 98° C., 85° C. to 95° C., 90° C. to 100° C., 95° C. to 100° C., 70° C., 75° C., 80° C., 85° C., 86° C., 87° C., 89° C., 90° C., 91° C., 92° C., 93° C., 94° C., 95° C., 96° C., 97° C., 98° C., 99° C. or 100° C. prior to hybridization.

Targets

In some embodiments, a target polynucleotide may be any nucleotide sequence for which a determination of the presence, absence, amount or characteristics is desired. In some embodiments, a target polynucleotide may be preselected by the person designing a given assay, and/or be associated with a particular genotype or phenotype of interest, and/or be selected for another reason.

In some embodiments, the target polynucleotide is a nucleotide sequence that contains, represents or is associated with a polymorphism.

In some embodiments, alleles can be interrogated by targeting one or more nucleotide polymorphisms. In some cases, a polymorphism occurs at a single nucleotide position, for example, one allele may have a thymine at a given position and an alternative allele, has for example, cytosine, at the same position. In some embodiments, the nucleotide polymorphism may comprise a substitution, deletion, insertion, copy number variation, translocation, methylation or another nucleotide modification, and/or a variant DNA sequence. In some embodiments, the polymorphism may include two, three, four, or more contiguous nucleotides.

The compositions and methods disclosed herein may find utility in identification of a single nucleotide polymorphism (SNP) in a target polynucleotide sequence. For example, in the case of genomic DNA samples from a diploid mammal with two copies of a given SNP, the SNP could be homozygous or heterozygous. In other examples, a triploid organism has 3 distinct alleles at a given locus. Polyploid cells and organisms contain more than two paired sets of chromosomes and have a numerical change in a whole set of chromosomes. Polyploidy is common in plants. For example, wheat has strains that are diploid (two sets of chromosomes), tetraploid (four sets of chromosomes) and hexaploid (six sets of chromosomes). See Example 8.

In some embodiments, in methods for identifying polymorphisms in target polynucleotide sequences, a first and second complementary probe are incubated with one or more samples that may or may not contain a polymorphism in a target polynucleotide sequence under conditions that provide for hybridization of complementary sequences. In some embodiments, an optional third probe is provided for a particular probe set. This third probe is typically similar to either the first or second probe, but is directed to a different allele at the same sequence of interest. See FIG. 1E.

In certain embodiments, if the complementary polynucleotide probe including a polymorphic nucleotide is complementary to the polymorphic nucleotide in a target polynucleotide sequence, then the complementary probes are joined together to create a product polynucleotide. In certain embodiments, if the polymorphic nucleotide on the complementary polynucleotide probe does not hybridize to the polymorphic nucleotide on the target polynucleotide, the two complementary probes typically are not joined and do not form a product polynucleotide.

In some embodiments, the product polynucleotides (or a portion or portions of the product polynucleotide, its amplification products, or complements thereof) are sequenced to determine the presence or absence of the polymorphism. In some cases, the sample identity is also determined by sequencing. In certain other embodiments, an array or other readout is used to determine the presence or absence of the polymorphism. In some embodiments, capture probes or oligonucleotides provided on an array are designed to be substantially complementary to the extended part of a primer, so unextended primers will not bind to the capture probes. Alternatively, unreacted probes may be removed prior to addition to the array or sequencing In some embodiments, the length of the first and second complementary sequence of the first and second complementary probes varies dependent upon one or more of a number of possible parameters such as the: (i) melting temperature of the duplex formed with the target polynucleotide, (ii) Tm, (iii) ionic strength of hybridization solution, (iv) complexity of the target polynucleotide, and the like.

In some embodiments, a sample contains one or more or a plurality of different target polynucleotides. In particular, the sample comprises at least two different target polynucleotides, at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more, 120 or more, 140 or more, 160 or more, 180 or more, 200 or more, 220 or more, 240 or more, 260 or more, 280 or more, or 300 or more, for example from 2 to 5000 target polynucleotides, from 2 to 20 target polynucleotides, from 5 to 30 target polynucleotides, from 10 to 50 target polynucleotides, from 25 to 75 target polynucleotides, from 40 to 100 target polynucleotides from 50 to 120 target polynucleotides, from 60 to 130 target polynucleotides, from 70 to 140 target polynucleotides, from 80 to 150 target polynucleotides, from 90 to 170 target polynucleotides, from 100 to 200 target polynucleotides, from 150 to 250 target polynucleotides, from 200 to 300 target polynucleotides, from 250 to 500 target polynucleotides, from 300 to 700 target polynucleotides, from 400 to 1000 target polynucleotides, from 500 to 1500 target polynucleotides, from 600 to 2000 target polynucleotides, from 700 to 3000 target polynucleotides, from 800 to 4000 target polynucleotides, from 900 to 5000 target polynucleotides, from 50 to 1000 target polynucleotides, from 100 to 2000 target polynucleotides, from 200 to 3000 target polynucleotides, from 300 to 4000 target polynucleotides, from 500 to 5000 target polynucleotides, or from 100 to 10,000 target polynucleotides The target polynucleotides may vary in length. In some embodiments, the target polynucleotides are from 10 nt to 100 nt, from 10 nt to 200 nt, from 10 nt to 300 nt or from 10 nt to 400 nt. In some embodiments, the target nucleotides are from 20 nt to 30 nt, from 20 nt to 40 nt, from 20 nt to 50 nt, from 20 nt to 60 nt, from 20 nt to 70 nt, from 20 nt to 80 nt, from 20 nt to 90 nt, from 20 nt to 100 nt, from 20 nt to 110 nt, from 20 nt to 120 nt, from 20 nt to 130 nt, from 20 nt to 140 nt, from 20 nt to 150 nt, from 20 nt to 160 nt, from 20 nt to 170 nt, from 20 nt to 180 nt, from 20 nt to 190 nt, from 20 nt to 200 nt, from 20 nt to 210 nt, from 20 nt to 220 nt, from 20 nt to 230 nt, from 20 nt to 240 nt, from 20 nt to 250 nt, from 20 nt to 260 nt, from 20 nt to 270 nt, from 20 nt to 280 nt, from 20 nt to 290 nt, from 20 nt to 300 nt, from 20 nt to 310 nt, from 20 nt to 320 nt, from 20 nt to 330 nt, from 20 nt to 340 nt, from 20 nt to 350 nt, from 20 nt to 360 nt, from 20 nt to 370 nt, from 20 nt to 380 nt, from 20 nt to 390 nt, or from 20 nt to 400 nt.

In some cases, the length of the target sequence may be varied depending upon the melting temperature ("Tm") of the sequence, pH, salt concentration, or the temperature of the incubating step.

The Tm's of the various target polynucleotides evaluated in a given assay are typically within 1° C., 2° C., 3° C., 4° C., 5° C., 6° C., 7° C., 8° C., 9° C., or 10° C. of each other. In some embodiments, the Tm's of the various target polynucleotides are within 1-3° C., 2-5° C., 2-4° C., 3-6° C., 3-5° C., 4-7° C., 4-6° C., 5-8° C., 5-7° C., 6-9° C., 6-8° C., 7-10° C., 7-9° C., 8-10° C., or 8-9° C. of each other.

Hybridization is carried out under various conditions known in the art. Stringent conditions are hybridization conditions under which a polynucleotide will hybridize preferentially to its target subsequence, and optionally, to a lesser extent, or not at all, to other sequences in a mixed population.

Generally, stringent hybridization conditions are selected to be about 5° C. lower than the thermal melting point (Tm) for a specific sequence at a defined ionic strength and pH. Very stringent conditions are selected to be equal to the Tm for a particular probe.

In carrying out the methods of the invention, a number of aspects of the hybridization reaction conditions may be varied including but not limited to the temperature of the hybridization reaction, the length of incubation, and the ionic strength of the hybridization buffer.

Joining—Ligation

In certain embodiments, after the samples, and the first and second first and second complementary probes have been incubated under conditions that allow hybridization of first and second first and second complementary probes to complementary target polynucleotides in a sample, first and second complementary probes may be joined. When first and second complementary probes are hybridized to target specific sequences adjacent each other, the respective 5'-phosphorylated and 3'-hydroxylated ends of a probe pair may be joined by any suitable means known in the art.

In certain embodiments, first and second complementary probes may be joined non-covalently. In other cases, the first and second complementary probes may be joined covalently. In some cases, the covalent joining may be accomplished by use of a ligase, for example a DNA Ligase from *T. aquaticus* or Ligase-65. In such cases, the ligase and a ligation buffer solution can be added to a solution comprising adjacent first and second complementary probes bound to target polynucleotides in a sample. In alternative embodiment the hybridization complex is added to the ligation solution. The temperature of the ligation reaction may be held constant for about 1 to 20 minutes, for example, about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes or longer than 20 min. In some embodiments, the ligation reaction is carried out at about 54° C. When an embodiment is analyzing RNA, the target polynucleotide may be converted to cDNA before hybridization with the first and second complementary probes, or the RNA transcript may serve as the hybridization target for the first and second complementary probes. When the RNA transcript serves as the hybridization target, the first and second complementary probes may continue to comprise DNA within embodiments that utilize ligation for joining the first and second complementary probes as the joining step may be modified by methods known in the art to facilitate DNA ligation on an RNA template (e.g., see U.S. Pat. No. 8,790,873). Exemplary ligases for ligating DNAs on an RNA template include SplintR PBCV-1 DNA Ligase or *Chlorella* virus DNA Ligase.

When ligation is complete, the temperature of the ligation reaction may be increased to about 94° C. for about 1 minute to aid in inactivating the DNA ligase and to denature the product polynucleotides. In some cases, the temperature can be increased to 90° C., 91° C., 92° C., 93° C., 94° C., 95° C., 96° C., 97° C., 98° C., or 99° C. for about 1 min, about 2 minutes, 3 minutes, 4 minutes or 5 minutes. In some cases, the ligation mix is then rapidly cooled to room temperature, about 4° C., or about 0° C.

Use of a Universal Base

As is known to those of skill in the art, ligase enzymes can make mistakes, e.g., connect or "seal" sequences with a mismatch in complementarity, such as a G/T mismatch, is present between the two nucleic acid strands. When first and second complementary polynucleotide probes hybridize to a target sequence, there may be a mismatch and the sequences may not be 100% complementary. In some embodiments, a complementary probe is designed to have a universal base, such as inosine (e.g. deoxyinosine), positioned near the interrogation site. The inosine (e.g. deoxyinosine) containing complementary probe will base pair with the complementary strand with less stability. In some embodiments, a universal base is substituted at the 2nd, 3rd, 4th, 5th, 6th, 7th, 8th, 9th, or 10th positon relative to the 3' nucleotide of the first complementary probe. Preferably, a universal base is substituted at the 2nd position relative to the 3' nucleotide of the first complementary probe. The universal base helps reduce or prevent a first complementary probe that does not have a 3' nucleotide or nucleotides complementary to the target sequence from being joined to a second complementary polynucleotide probe. Alternatively, or in addition to the above, a universal base can be substituted at the 2nd, 3rd, 4th, 5th, 6th, 7th, 8th, 9th, or 10th position relative to the 5'-nucleotide of the second complementary polynucleotide probe to aid in preventing or reducing joining of the second complementary polynucleotide probes that do not have a 5'-nucleotide or nucleotides complementary to the target sequence from being joined to a first complementary polynucleotide probe. In some embodiments, inosine (e.g. deoxyinosine) is the universal base used to destabilize mismatches (mostly G/T mismatches), so a ligase will not seal first and second complementary polynucleotide probes when there is a mismatch. In other embodiments, inosine (e.g. deoxyinosine) or another universal base is used to avoid destabilizing mismatches in the body of the target sequence (where a known proximal SNP occurs), and thus still enable appropriate ligation that would otherwise be disrupted although the 3' nucleotide of the first probe is complementary to the target sequence at the interrogation position. In certain embodiments, where two or more polymorphic positions are known to occur within the complementary portions of the first and/or second complementary probes, universal bases may be employed at these positions to avoid destabilizing mismatches.

Bar Codes and Sample Indices

In certain embodiments, a first and/or second complementary probe comprises a bar code that allows the sample, and/or the target sequence (locus and/or polymorphism or interrogation site) to be identified.

In some embodiments, the first complementary probe is complementary to a first target sequence and comprises an interrogation site barcode that is not complementary to the target polynucleotide.

An interrogation site bar code may aid in determining the presence, absence or amount of a target polynucleotide (e.g., a locus) and/or variations (e.g., polymorphisms) in a target polynucleotide. In some embodiments, the entire interrogation site bar code or a portion of the interrogation site bar code may be in one, or both, of the first and second complementary probes in a section that is non-complementary to the first or second target sequence. In some embodiments, an interrogation site bar code may identify both a locus and an allele (either as one sequence combined or as separate portions of a single sequence). In some embodiments, the interrogation site bar code may comprise a sequence portion that is non-complementary to the target sequence and a portion that is complementary to the target sequence. In some embodiments, the interrogation site bar code may identify only an allele. In such cases it is partially or completely non-complementary to the target sequences. In some embodiments the interrogation site bar code is not complementary to the target polynucleotide sequence.

In such cases, the interrogation site bar code is within the first target sequence, and is therefore not complementary to the first target sequence, as shown for example in FIG. 1.

An interrogation site barcode is typically 5 or more nucleotides in length. Exemplary interrogation site barcode sequences are 5, 6, 7, 8, 9, 10, 11, 12, 13, 14, 15, 16, 17, 18, 19, 20, 21, 22, 23, 24, 25, 26, 27, 28, 29, or 30 or more nucleotides in length.

In some embodiments, an interrogation site barcode comprises at least 5, at least 6, at least 7, at least 8, at least 9, at least 10, at least 11, at least 12, at least 13, at least 14, or at least 15 or more nucleotides.

In some embodiments, a first complementary probe includes an interrogation site bar code and when the first complementary probe is complementary to a first target sequence of a target polynucleotide, the interrogation site bar code sequence does not hybridize to the target, however, the 5' and 3' portions flanking the interrogation site bar code are portions of the first complementary probe that are complementary to the first target sequence. See FIG. 1.

In some embodiments, the second complementary probe contains a sequence portion that is complementary to a second target sequence and an immediately adjacent sequence portion that is non-complementary to the second target sequence. The non-complementary portion of the first and second complementary probes may comprise a universal sequence. The universal sequences for the first and second complementary probes may be the same or different.

In certain embodiments, a sample index is added to the product polynucleotide (or reaction products thereof) by PCR using a priming sequence that is complementary to the second complementary probe. However, in certain embodiments, the sample index could be added via the first complementary probe. In certain exemplary embodiments, the sample index can be located on the PCR primer 1 of the first complementary probe so that the sample index is near the barcode for sequencing without the need to sequence the first and second target sequences.

In certain embodiments, a sample index is typically 5 or more nucleotides in length. In certain exemplary embodiments, sample indices are 5, 6, 7, 8, 9, 10, 11, 12, 13, 14, 15, 16, 17, 18, 19, 20, 21, 22, 23, 24, 25, 26, 27, 28, 29, or 30 or more nucleotides in length.

Exemplary 12 and 15 nucleotide sample indices are shown in Table 1.

In some embodiments, the total number of unique sample indices is about 16,128 based on 12-mer sequences. In some embodiments, the total number of unique sample indices is about 50,000 based on 15-mer sequences. In other embodiments, the total number of unique sample indices is about 66,000 based on 15-mer sequences.

In some embodiments, the sample index is used to determine the identity of a sample by sequencing the sample index for each product polynucleotide.

Selection/Enrichment

An enriching step may be included in an assay of the invention before the analysis step. The enriching step serves to increase the amount of product polynucleotide and the ratio of product polynucleotide to non-product polynucleotide in the reaction mixture. This may be accomplished by selection of the product polynucleotide and/or removal of non-product polynucleotides. In some embodiments, the enriching step is based on size, affinity, charge, or sequence, or by removal of some or all of the non-product polynucleotides, for example by selection, segregation or digestion. The joining and enrichment steps may occur in the same or different reaction mixtures.

In some embodiments, a product polynucleotide may be selected based on the presence of a specific sequence, for example, a sample index, or a sequence such as the complementary sequence. In some cases, the product polynucleotide may comprise a bar code that is designed to be selected during an enrichment step.

In some embodiments, enrichment includes an amplification step. For example, a sample index may be incorporated into the product polynucleotides during the amplification step, using any amplification reaction known to those of skill in the relevant art, e.g., polymerase chain reaction (PCR).

Tagging amplified products with sample indices is useful when product polynucleotides from different samples are combined and pooled into libraries for sequencing or other analysis. Primer binding sequences (or sites) may be incorporated into first and/or second complementary polynucleotide probes to facilitate amplification of product polynucleotides, whether linear or exponential. Primer binding sites are used to bind primers to initiate primer elongation or amplification. Primer binding sites are typically located in parts of the probe other than in the first or second target sequence. In some embodiments, the primer binding site is located in a sequence which is non-complementary to the target polynucleotide.

In some embodiments, PCR is used to add sample indices to product polynucleotides, enabling pooling of product polynucleotides for purposes of sequencing. The PCR primers can comprise a sequence that is complementary to a portion of the product polynucleotide or the first or second complementary probe. For example, when a first and a second PCR primer are used to direct PCR amplification of a product polynucleotide, the first PCR primer may comprise a sequence that is complementary to a sequence on the product polynucleotide, and the second PCR primer may comprise a sequence that is non complementary to a sequence on the product polynucleotide.

In some cases, two different sample indices (e.g., one on each PCR primer) are incorporated into a product polynucleotide and thereby aid in increasing the number of samples that can be identified and thus analyzed in a single assay. In some cases, only one PCR primer includes a sample index or bar code.

In one exemplary embodiment, enrichment is carried out using PCR amplification.

Polymerizing enzymes include, but are not limited to, DNA and RNA polymerases, reverse transcriptases, etc. Conditions favorable for polymerization by different polymerizing enzymes are well-known to those of skill in the art.

Amplification is typically carried out in an automated thermal cycler to facilitate incubation times at desired temperatures. In some embodiments, amplification comprises multiple cycles of sequential annealing of at least one primer with complementary or substantially complementary sequences to at least one target nucleic acid, synthesizing at least one strand of nucleotides in a template-dependent manner using a polymerase, and denaturing the newly-formed nucleic acid duplex to separate the strands. The cycle may or may not be repeated. Amplification can comprise thermocycling or can be performed isothermally.

In some embodiments, amplification comprises an initial denaturation at about 90° C. to about 100° C. for about 1 to about 10 minutes, followed by cycling that comprises annealing at about 55° C. to about 75° C. for about 1 to about 30 seconds, extension at about 55° C. to about 75° C. for about 5 to about 60 seconds, and denaturation at about 90° C. to about 100° C. for about 1 to about 30 seconds. Other times and profiles may also be used. For example, primer annealing and extension may be performed in the same step at a single temperature.

In some embodiments, the cycle is carried out at least 5 times, at least 10 times, at least 15 times, at least 20 times, at least 25 times, at least 30 times, at least 35 times, at least 40 times, or at least 45 times. The particular cycle times and temperatures will depend on the particular nucleic acid sequence being amplified and can readily be determined by a person of ordinary skill in the art.

In some embodiments, linker or adaptor sequences that facilitate annealing of PCR primers or processes involved in sequence generation can be added to a product polynucleotide using PCR or another DNA amplification process. This is in contrast to methods traditionally used in the art wherein adapters are ligated to polynucleotides that are to be sequenced. Linkers and adaptors can be used as a component of physical, chemical, or enzymatic processes.

Samples may be pooled after enrichment and/or amplification. In such embodiments, product polynucleotides from various samples are combined resulting in a pool of product polynucleotides, which are analyzed and/or sequenced together.

In cases where multiple samples are sequenced together, each sample can be amplified separately, wherein a sample index is included in the first and/or second PCR primer, wherein one or more sample indices are unique to the sample. Each product polynucleotide from a given sample has the same sample index. In some cases, wherein both PCR primers comprise a sample index, the bar codes may be the same or different. In such embodiments, the determination of the sequence of product polynucleotide from one or more (typically multiple) samples is accomplished at the same time.

In some embodiments, the invention provides compositions, methods and kits for use in target polynucleotide copy number determinations. Copy number variation ("CNV") is implicated in gene control and human disease. CNV may be evaluated using first and second complementary probes for each potential CNV locus and one or more loci. The probes may include a bar code as described above. The relative amount of each sequence may be determined, for example, using next generation sequencing, wherein the relative read counts of the CNV locus (target polynucleotide) and single copy target polynucleotide(s) can be used to estimate copy number of the CNV locus (target polynucleotide). CNV is determined by comparing samples with known CN and/or CNV to unknown samples or by comparison to a known reference number. For example, if a sample has two copies of a target polynucleotide sequence, the total number of sequence reads would indicate two copies of the target polynucleotide sequence when normalized to a control, and a sample with four copies of the target polynucleotide sequence would yield 4 times the number of sequence reads relative to the normalized sample. A sample with a deletion of all copies would yield no sequence reads.

In some embodiments, this CNV detection is extended to determining an amount of target polynucleotide present in the sample.

In some embodiments, the first and second complementary probes are separated by one or more nucleotides while hybridized to the sequence of interest. The gap can be a single nucleotide or more than one nucleotide. The extension can be carried out at the 3' end of the first probe when hybridized to a sample nucleic acid. In such cases, the sample nucleic acid acts as a template directing the type of modification, for example, by base-pairing interactions that occur during polymerase-based extension of the first probe to incorporate one or more nucleotides in a gap filling step. If the gap fill step is performed to completion, with the 3' end of the first complementary probe immediately adjacent to the 5' end of the second complementary probe, the complementary probes can then be joined as discussed above, e.g., via enzymatic ligation. The resulting polynucleotide product can then be analyzed as discussed for embodiments without a gap fill step.

In variations wherein the product polynucleotides are sequenced by next generation sequencing, the PCR primers can also be used to generate sequences for use with a specific sequencing technique, e.g., to add adapter sequences that facilitate binding of product polynucleotides to the surface-bound DNA oligonucleotides within an Illumina NGS flow cell.

In variations wherein the product polynucleotides are analyzed using an array readout, the PCR primers can also be used to generate sequences for use with a particular array, e.g., to add linker sequences that facilitate product polynucleotides binding to DNA oligonucleotides (capture probes) on an array, such as an Axiom® or GeneChip® microarray (Affymetrix, Inc., Santa Clara, California) or BeadArray® microarray (Illumina, Inc., San Diego, California).

In some embodiments, a probe, target nucleotide or product nucleotide is attached to a solid support.

Improved Sample Index Primers

As described herein, some embodiments add sample indices to the product polynucleotide by the incorporation of the sample index sequence within a primer sequence (e.g., a PCR primer). While many possible different sample index sequences are possible (i.e., 4^15 different 15mer sequences), creating an optimized set must address not only differentiating one index sequence from another (e.g., ensuring that a sample index is not called incorrectly even if one of the bases is incorrectly sequenced) but also desirably addresses compatibility and optimization with the overall assay. Within embodiments that add sample indices by incorporation of the sample index as part of a primer oligonucleotide (e.g., for PCR), the aspects of compatibility and optimization may include such amplification. Other considerations related to the overall assay also pertain the required number of samples to be processed and the potential flexibility of the sample index primers at issue. For example, 15mer sample indices can be designed such that the first 12 bases can be utilized in situations where a lower number of samples are at issue and the full indexing capabilities of the available pool of 15mers is not needed, and thus the 15mers can be treated as 12mers to further optimize the overall assay (e.g., in a sequencing detection embodiment, only having to sequence the first 12 bases to identify the sample index in order to save time and reagents). Methods of identifying sequences that will be useful include multiple steps that are outlined in this disclosure. In certain embodiments, one such step can be identifying and removing those sequences that are not useful or will otherwise hinder assay performance from a previously identified set of possible sequences. Additionally, identifying those sequences that are likely to be only sometimes problematic and removing those is also important as these sequences may pass initial testing that is empirically derived, and yet perform sub-optimally under certain assay conditions.

In certain embodiments, the 73536 indices may be used in a 384 microtiter plate format, which is enough for 169 plates. In other embodiments, the first 16,128 15mer indices of the 65280 indices may also be used as 12mers in a 384 microtiter plate format, which is enough for 42 plates. These indices have been optimized not only with respect to the overall set, but also on a plate by plate basis (e.g., the 1-384, 385-768, 769-1152, etc.). While it is possible that a handful of these indices may have unexpected issues that come up in actual testing and may need to be replaced, substituting a small number of indices out for other indices on a per plate basis is unlikely to affect the optimization in any substantive manner (e.g., as long as 99% of the sequences are kept, or replacing 3-4 sequences in a 384 plate, no drop-off in optimization should be observed).

Multiple factors can be important to the selection of an optimized set of sample indices, including the maximization of orthogonality, maximization of specificity and ensuring compatibility with other assay components. Orthogonality is desirably maximized not only with respect to the sample index sequence itself within a set of sample indices, but also in the context of the particular assay step. For example, for sample indices that are added to the product polynucleotide during a PCR step, maximum orthogonality considers not only the sample index sequence itself but also the sequence(s) of the PCR primer(s). There may also be other sequences that should be accounted for to maximize orthogonality. For example, if a PCR step is utilized to add not only a sample index sequence but also an adapter sequence for later use within the assay (e.g., a next generation sequencing flow cell adapter sequence), then orthogonality is desirably maximized with respect to the sample indices and also the primer sequence(s) and the flow cell adapter sequence(s). Maximizing specificity is also an important consideration, and aspects such as avoiding homopolymers (e.g., avoiding use of the same base for 3 consecutive bases within the sample index) and standardizing GC content within a desired range (e.g., within 40 to 60%, 42 to 58%, 44 to 56%, and so on as may be desired or required for a particular embodiment). Other assay components are also desirably considered during optimization, such as nucleic acid sequences that will be used within the assay for detection, such as the sequences within next generation sequencing library construction.

It is known to those skilled in the art that matching oligonucleotide design characteristics and the specificity of the chemical environment or assay conditions are important. It is further known that there are multiple determinants of specificity in assays of this type. Several non-limiting examples of assay elements that can be modified to alter specificity include the concentration of solvents such as DMSO, concentration of ions, either monovalent such as K+ or Na+, or divalent such as Mg++, concentration of oligonucleotides, time of interaction, and temperature of the assay and/or the temperature during different parts of the assay.

In certain embodiments, the focus was on temperature as a determinant of specificity as a non-limiting example due to the general correlation that lower temperature generally correlates with lower specificity and higher temperature to higher specificity. Thus, different temperature regimes described herein should be considered as representing higher and lower specificity regimes rather than strictly temperature.

Figure 11A:
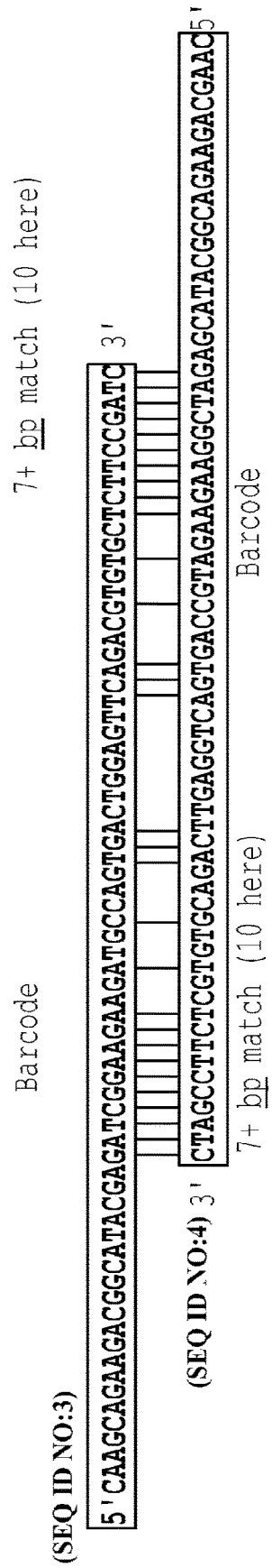
FIG. 11A is a diagram showing an example sequence with self complementarity indicated by lines.
Figure 11B:
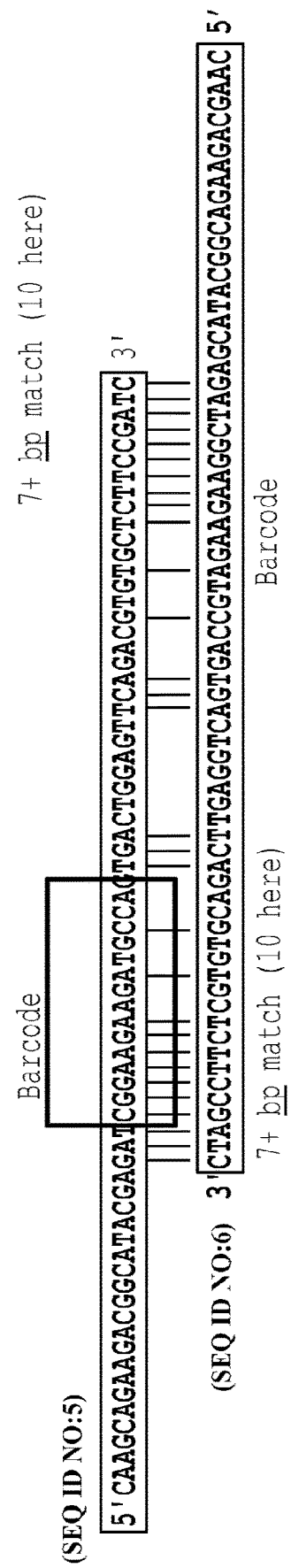
FIG. 11B is a diagram showing the same sequence in FIG. 11A with the variable barcode region indicated with a box.
Figure 12A:
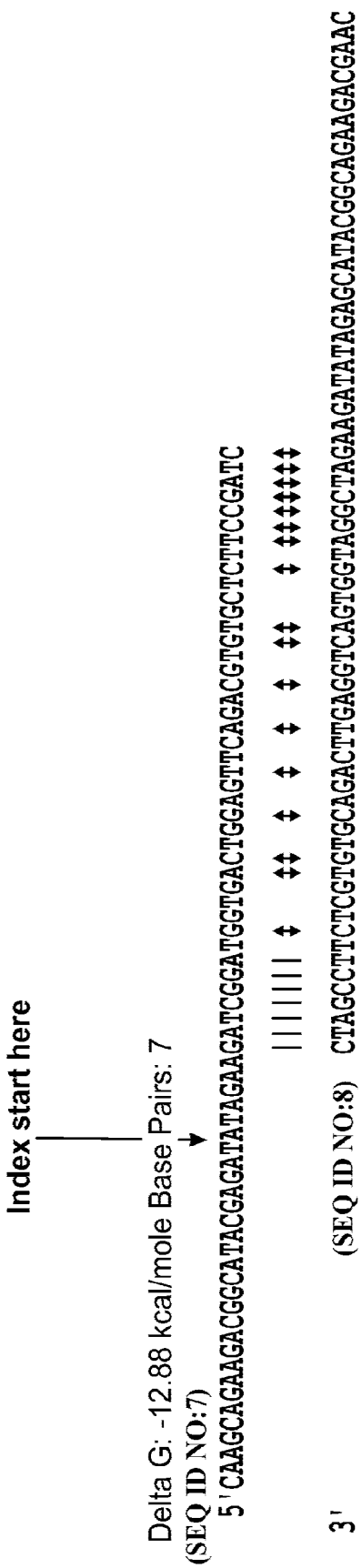
FIG. 12A is a diagram showing a variation of a 3' end complementary 7 base pair (bp) internal to index (7+0+1) plus a few other matches to stabilize the dimer.
Figure 12B:
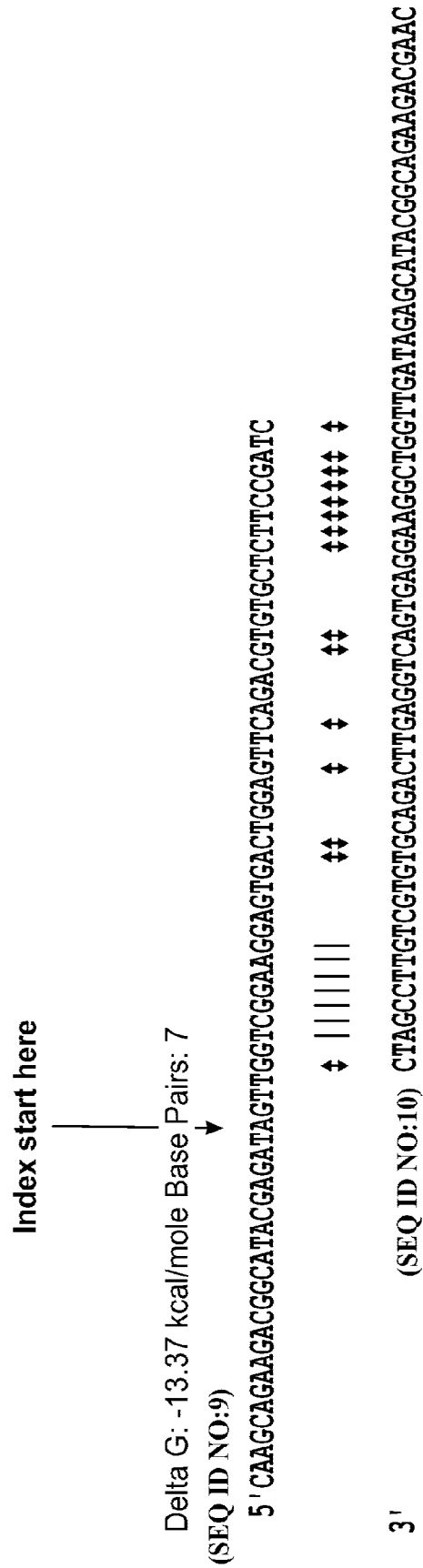
FIG. 12B is a diagram showing a variation of a 3' end partial complementary 7 base pair (bp) internal to index (1+0+7), the 0 in this case is GT pairing, which may be the equivalent to a 9 base pair (bp) match.

In exemplary embodiments, PCR reactions are often run with an annealing and extension temperature of 60° C. Primers designed to work at this temperature typically result in low amplification efficiencies, and thus low product yields when run at higher temperatures such as 65° C. Primers designed to work optimally at 65° C. can achieve good yields when run at a temperature of 65° C.; however the design characteristics of the primers designed for 65° C. are slightly different than those designed for 60° C. In particular, the primers are designed so that they have more stable binding to the target sequence. There are many design criteria known to those skilled in the art to predict the binding or empirically determine the binding of different designs. These are often correlated to sequence composition (GC content), free energy (delta G) value and length or number of matching base pairs between two complementary strands. Similar patterns hold for undesired off target effects. Sequence motifs that can lead to undesired products, such as primer dimerization products, can be more problematic with lower temperature or lower specificity reactions. Of particular concern are sequence motifs where several bases at the 3' end of the oligonucleotide have fully complementary or nearly full complementarity to a region in another oligonucleotide in the assay or to itself (FIGS. 11A&B and FIGS. 12A&B). The delta G values for dimer products, or length of the complementary section that will be problematic, is inherently variable with temperature (or other specificity determinant). Lower temperatures will allow non-specific amplification by dimers having less complementarity, highly correlated to shorter region of complementarity at the 3' end. Thus, by running the assay at 65° C. rather than 60° C., more bases of complementarity are needed to produce non-specific amplification events. Furthermore, it has been determined that a sufficiently long sequence of self-complementarity between a portion of a sample index primer and the 3' end of the sample index primer can cause primer dimerization even if the sequence of complementary bases is not exactly at the 3' end, but is internal to the 3' end by one or more bases.

In certain embodiments, under the reaction conditions employed in the assay, a motif with 3' complementarity of 7 bp of perfect match or 9 bp with one mismatch can be tolerated in some cases, but not others, dependent upon the degree of additional complementarity throughout the dimer molecule. This is therefore a useful motif to use to identify otherwise useful sequences in that it identifies a number of possible oligonucleotides that will fail to perform well under most assay conditions, and also identifies those sequences that are likely to perform adequately under one set of conditions, but be prone to failure under very slightly lower specificity conditions. These sequences can particularly, but not exclusively, occur due to the 3' complementarity spanning different "regions" within the oligonucleotide, for example with part, but not all, of the complementarity being due to variable regions within the oligonucleotide. An example here is the "barcode" portion (FIGS. 11A&B and FIGS. 12A&B).

Additionally, running the assay under conditions (such as at 65° C.) that tolerate longer regions of complementarity (such as 7 bp or 9 bp with 1 mismatch) prior to failure is highly desirable over conditions (such as at 60° C.) that will fail with shorter regions of 3' complementarity (such as 5 or 6 bp). The tolerance of the longer motifs greatly reduces the number of oligonucleotide sequences that must be removed from the pool of otherwise useful sequences.

Likewise, the assay could be run with an anneal/extension temperature of 70° C. which would further limit the off target effects but also impose other constraints on the design.

The disclosure of a set of 15mer sample index barcodes includes multiple specific design elements that taken together produce an optimal set of indexes both in total, and the various subsets therein for the given reaction conditions and other conditions of similar specificity. The process used to identify the set is also not to be limited to the specific disclosed set since a similar, but not identical set could be developed using the same process for assay conditions of greater or lesser specificity by slight alterations of the disclosed.

Genotyping Methods for Detection of a Target Polynucleotide in Polyploidy Samples.

Figure 13:
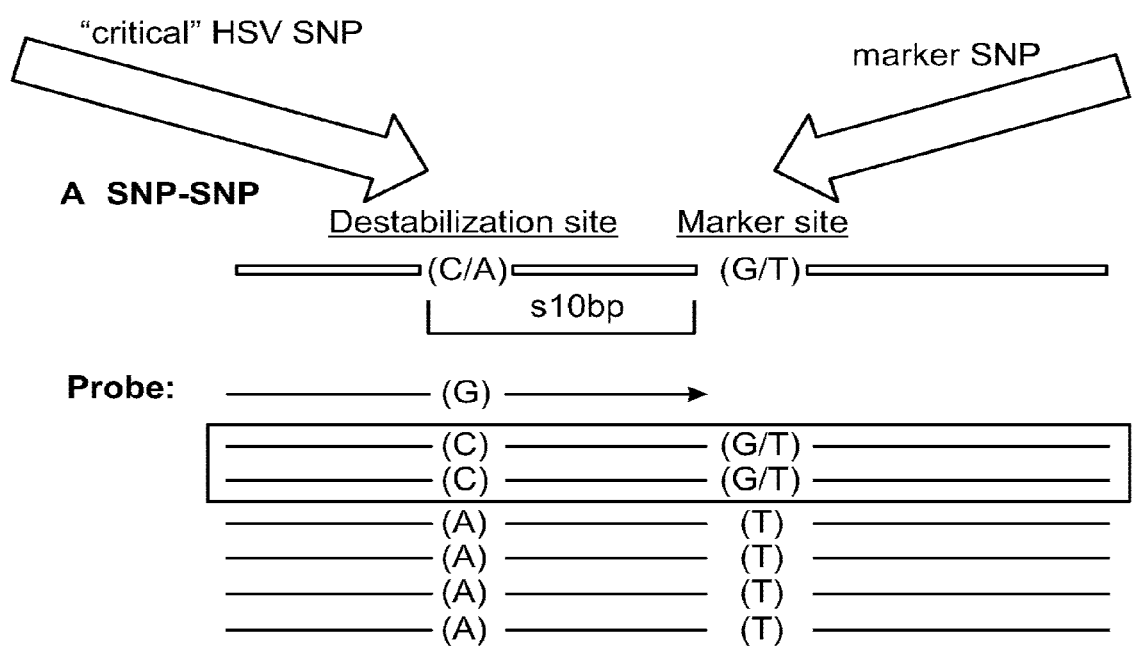
FIG. 13 is a diagram showing the destabilization site (proximal SNP) and the marker site (target SNP) and their relative positions within polyploidy target genomes. The destabilization site can be on either side of the marker/target SNP. Open arrows point to their respective sites within the target genome.

As described herein, genotyping methods (and associated data analysis) are used to detect the presence or absence of a target polynucleotide in polyploidy samples. In certain embodiments, the target polynucleotide may be an SNP or the result of a deletion/insertion event (Indel). In complex genetic situations such as in polyploidy samples, when generating sequence data on the genome of interest, the presence of non-informative genomes increases the quantity of sequence reads required for each locus and sample. Multiple ploidy reduction strategies are described herein to reduce the generation of sequence data in non-informative genomes. An exemplary ploidy reduction concept that exploits marker SNPs near subgenome-specific HSV SNPs is described herein (See FIG. 13). The ploidy reduction approaches described herein may be used individually or in combination with the probes described herein.

Figure 14A:
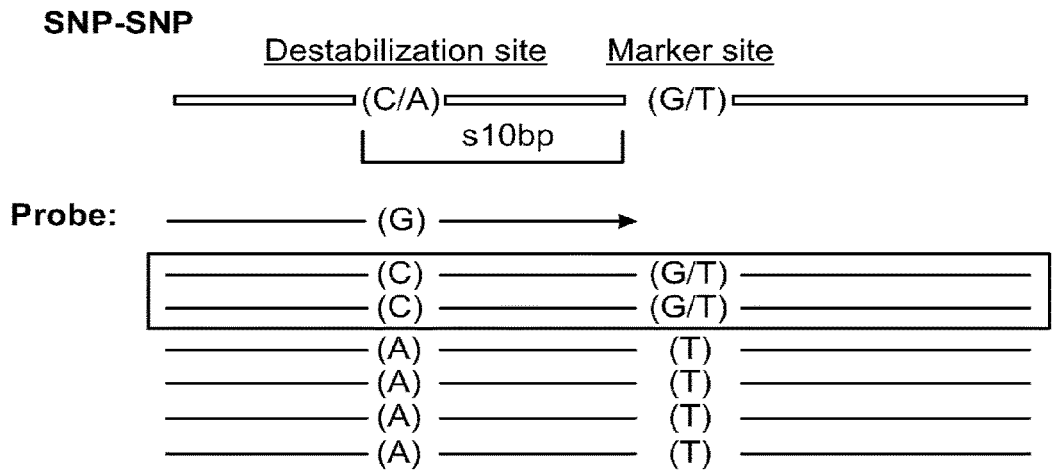
FIGS. 14A-14C are diagrams showing the destabilization site (proximal SNP) and the marker site (target SNP) and their relative positions within polyploidy target genomes. The destabilization site can be on either side of the marker/target SNP.
Figure 14B:
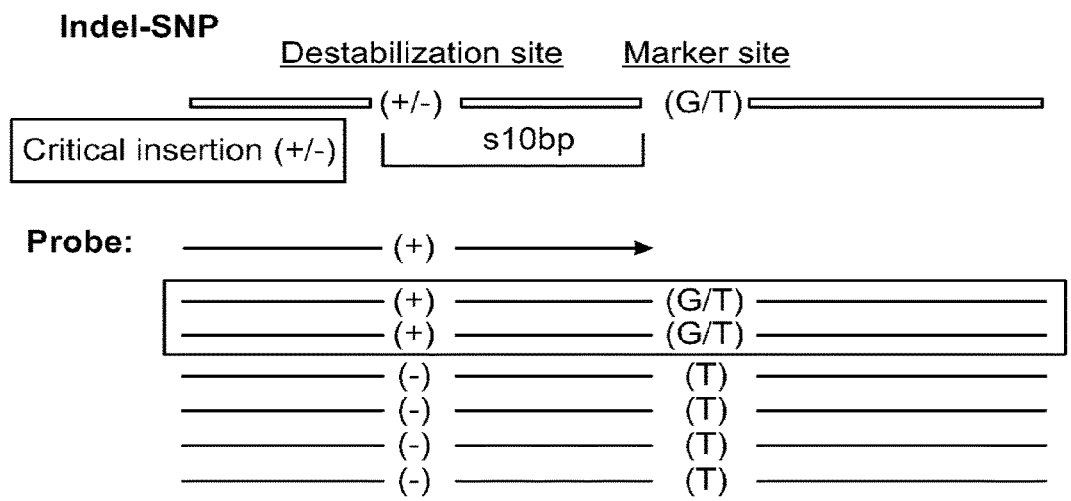
Figure 14C:
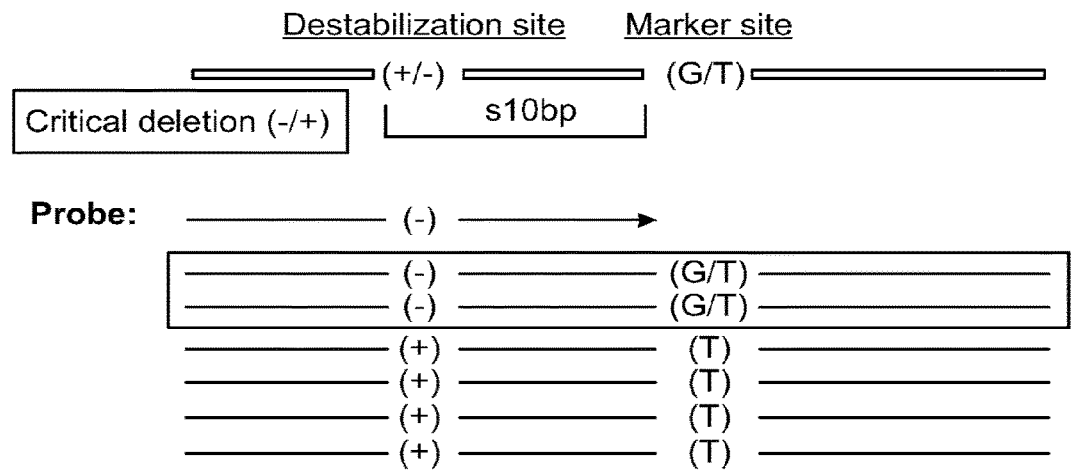

In an exemplary first approach, public and proprietary wheat genome sequence data containing the target SNP/indel and the proximal SNP/indel information are obtained. Based on the knowledge of the relative position of the proximal SNP/indel to target/marker SNP/indel, probes are designed that are selective for the genome of interest using the proximal SNP/indel destabilization strategy to reduce ploidy through biological complexity. Target markers that are genotyped on Axiom and demonstrate diploid clusters are selected. It is ensured that there are no proximal SNP/indel in the 9 bases on either side of the target markers (See FIGS. 14A-C).

Figure 15A:
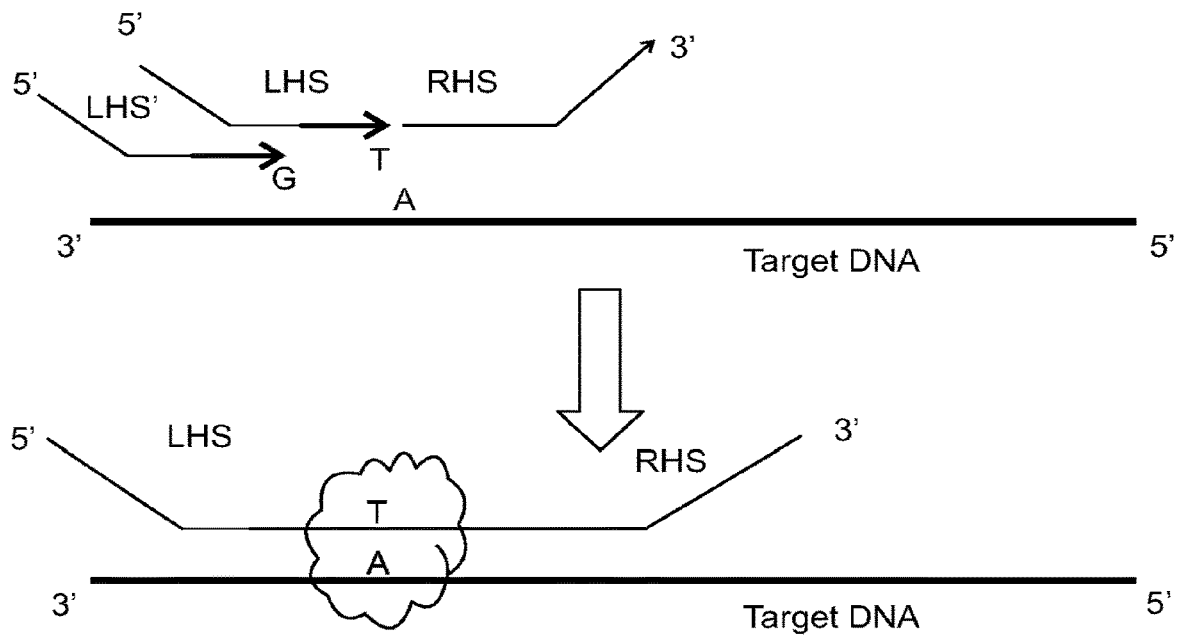
FIGS. 15A and 15B are diagrams showing probes used in genotyping methods for detecting the presence or absence of a target polynucleotide in polyploidy samples.
Figure 15B:
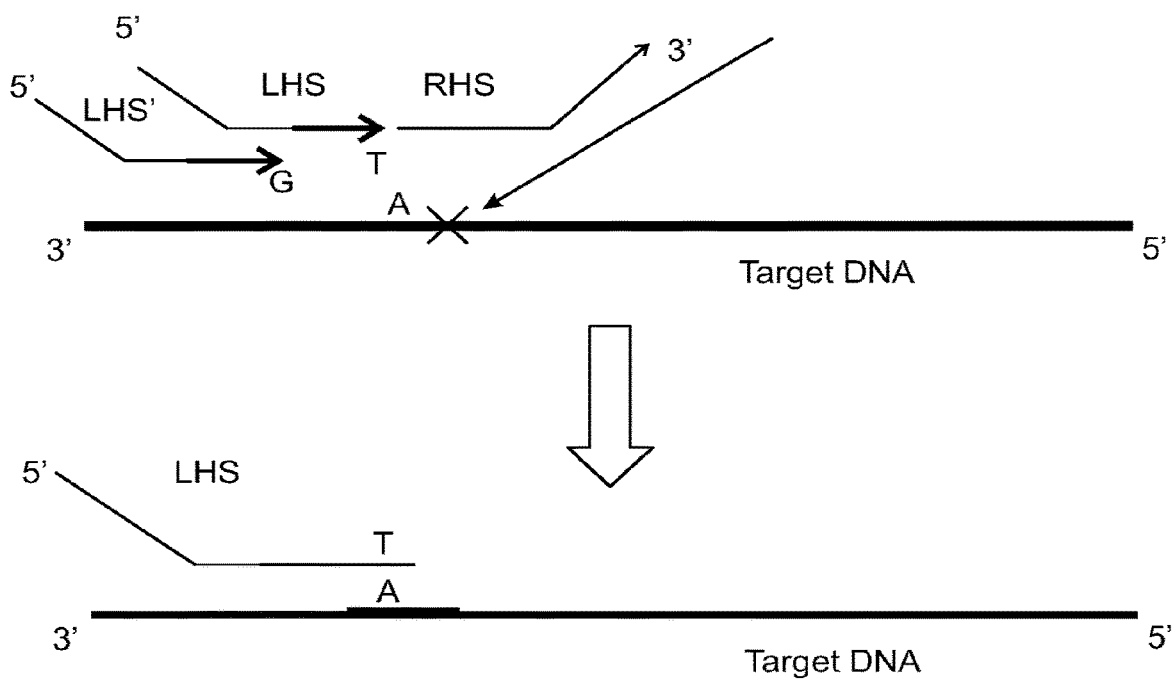

In one embodiment, one form of the first complementary probe was designed to be complementary to the target sequence with the SNP/indel (LHS), the other form of the first complementary probe was designed to be complementary to the target sequence that does not have the SNP/indel (LHS'). The second complementary probe (RHS) is immediately adjacent to the 3' sequence on both forms of the first complementary probe. The presence of a proximal SNP near the target SNP causes a destabilization effect that prevents ligation. As a result, selection was accomplished for the genome of interest (i.e., the target genome with the proximal SNP will generate low sequence reads). Accommodating the proximal SNP in the probe design causes a locus that produces no reads to become fully functioning (See, FIGS. 15A&B).

In an exemplary second approach, public and proprietary wheat genome sequence data containing the target SNP/indel and the proximal SNP/indel information are obtained. Based on the knowledge of the relative position of the proximal SNP/indel to target marker SNP/indel, blocking oligos that are complementary to the target genome having the proximal SNP/indel are added to prevent hybridization of RHS to the target genome.

Figure 16A:
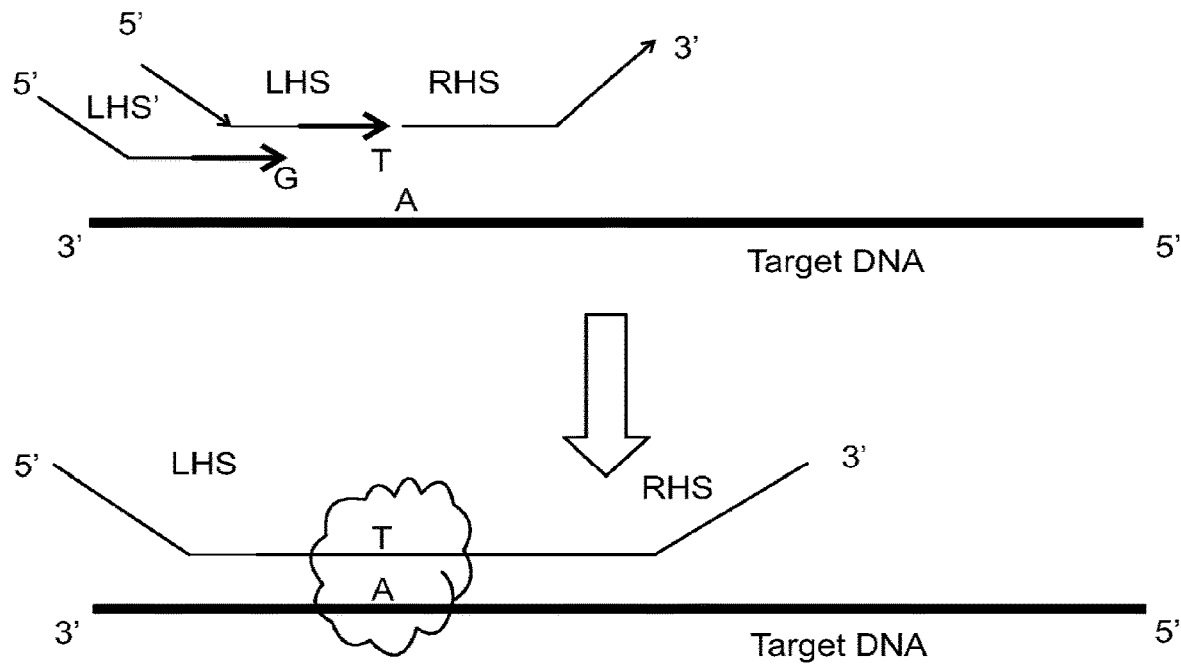
FIGS. 16A and 16B are diagrams showing probes used in genotyping methods for detecting the presence or absence of a target polynucleotide in polyploidy samples.
Figure 16B:
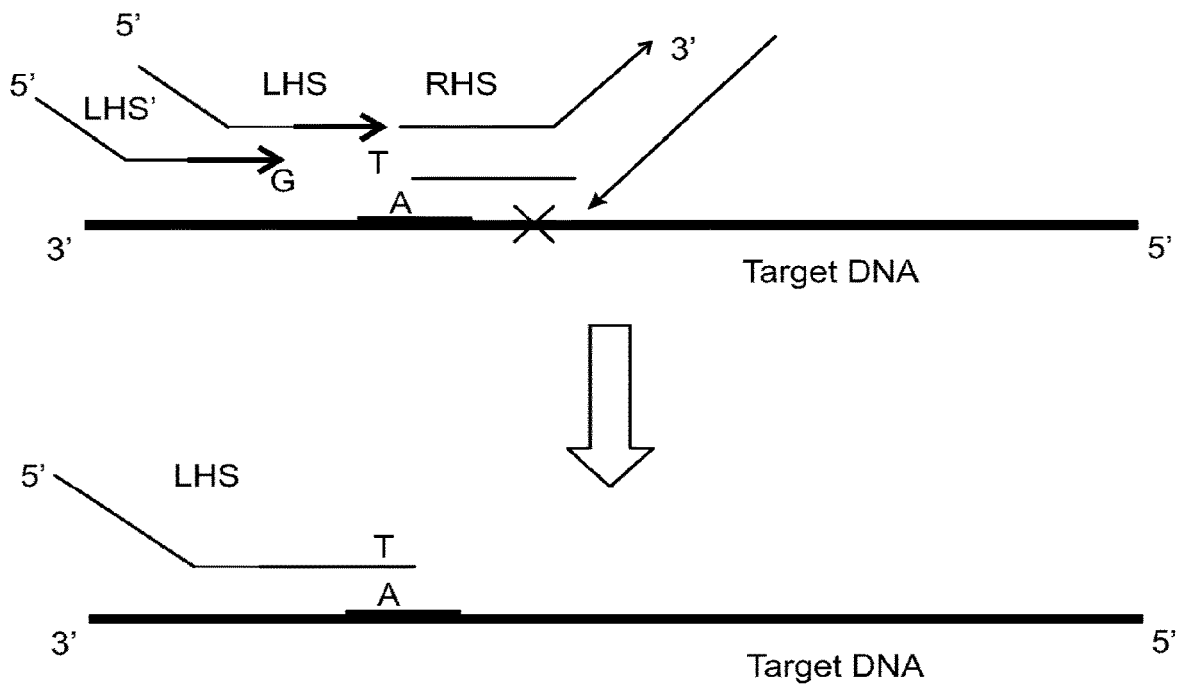

In one embodiment, one form of the first complementary probe was designed to be complementary to the target sequence with the SNP/indel (LHS), the other form of the first complementary probe was designed to be complementary to the target sequence that does not have the SNP/indel (LHS'). The second complementary probe (RHS) is immediately adjacent to the 3' sequence on both forms of the first complementary probe. Blocking/competing oligos that are complementary to target sequence containing the proximal SNP/indel are added. Blocking oligos prevent hybridization of RHS to target DNA. As a result, selection was accomplished for the genome of interest (i.e., the target genome with the proximal SNP will generate low to none sequence reads). Accommodating the proximal SNP in the probe design with the addition of blocking oligos causes a locus that produces no reads (See, FIGS. 16A&B). This approach is suitable for when proximal SNP is between base 1 and 10 of target marker. Secondary polymorphism may not be destabilized.

In an exemplary third approach, public and proprietary wheat genome sequence data containing the target SNP/indel and the proximal SNP/indel information are obtained. Based on the knowledge of the relative position of the proximal SNP/indel to target marker SNP/indel, PCR primers are designed and an upfront PCR amplification step that selectively amplify unique genome or subgenome of interest is added. In this approach, one or both of the PCR primers may be complementary to the target genome sequence having the proximal SNP/indel in the genome sequence. This unique upfront PCR amplification step may be in parallel workflow format (i.e., samples are divided into two).

Figure 17A:
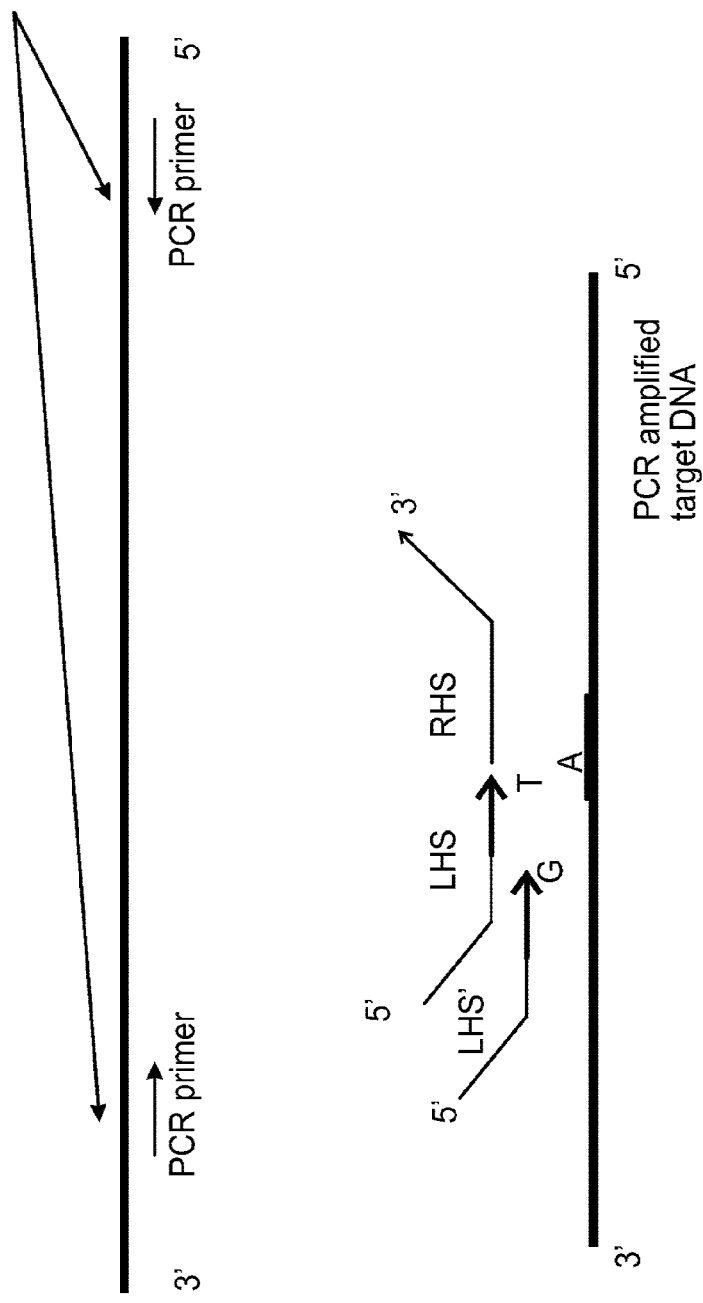
FIGS. 17A and 17B are diagrams showing probes used in genotyping methods for detecting the presence or absence of a target polynucleotide in polyploidy samples.
Figure 17B:
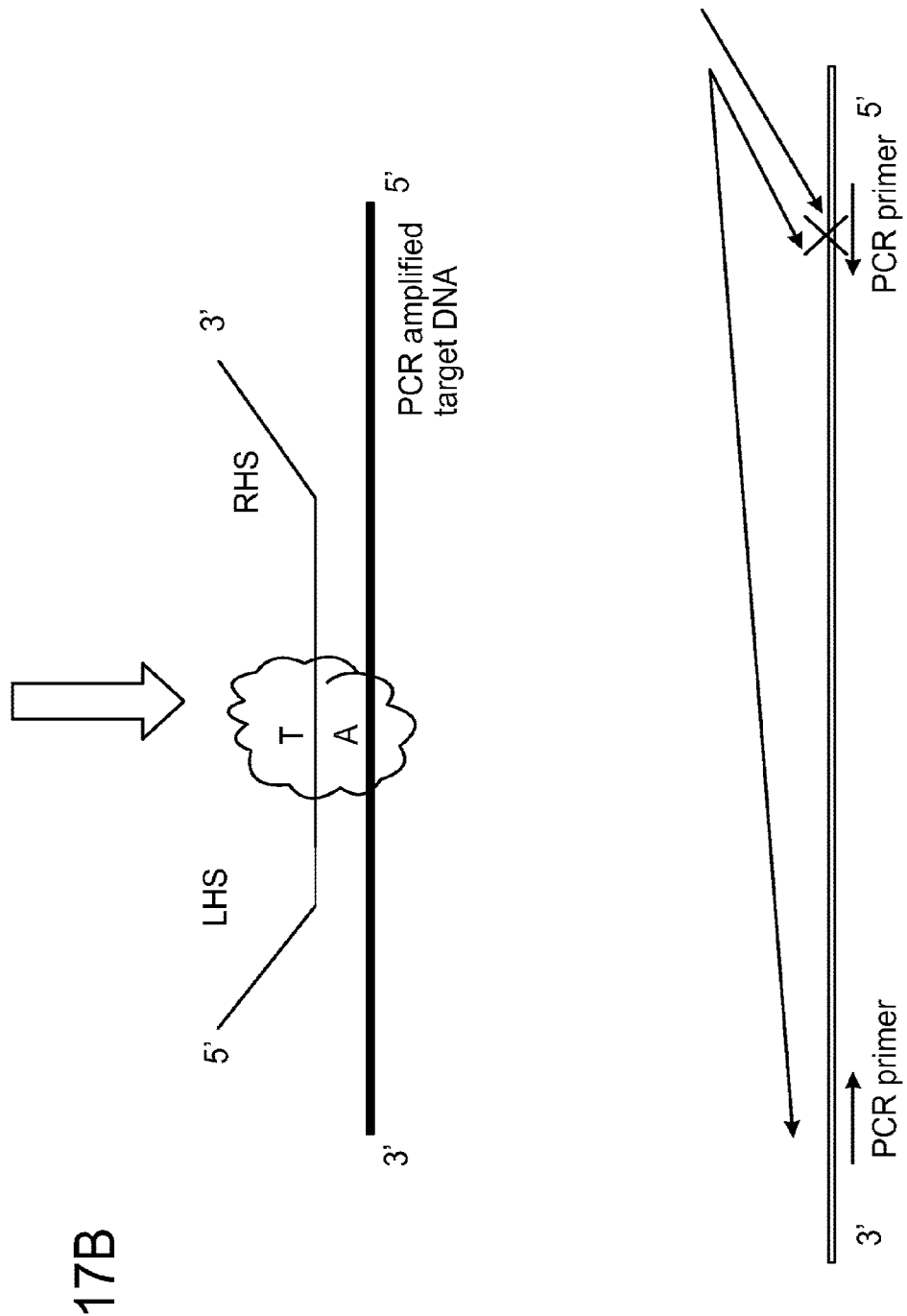

In one embodiment, one form of the first complementary probe was designed to be complementary to the target sequence with the SNP/indel (LHS), the other form of the first complementary probe was designed to be complementary to the target sequence that does not have the SNP/indel (LHS'). The second complementary probe (RHS) is immediately adjacent to the 3' sequence on both forms of the first complementary probe. An upfront PCR amplification step is added using PCR primers designed to specifically amplify unique genome or subgenome of interest. The proximal SNP/indel destabilizes the hybridization of the PCR primers. As a result, selection was accomplished for the desired unique genome of interest (i.e., the none desired genome containing the proximal SNPs are eliminated from subsequent workflow). Various locus and genome combinations are accommodated using multiple PCR primer set and probe set combinations (See, FIGS. 17A&B).

In certain embodiments, a 600× average coverage approach may be used for a small number of selected markers. This approach requires parallel workflow (i.e., samples are divided into two). In one embodiment, samples are split between the markers at issue with nearby proximal SNPs or single base indels, and for the affected markers, instead of sequencing for 200× coverage as used in other approaches, it simply increases that for the split with the affected markers to having 600× coverage (i.e., to use additional sequencing time and expense to compensate instead of trying to compensate on the upfront Eureka portion). This approach has been used in other contexts, such as deep sequencing for expression with RNA-Seq to assist with detection of rare transcripts, so in a different context this would be the Eureka equivalent.

The choice of which approaches to use depends on the gift the three wheat genomes present in location of proximal SNP relative to the target SNP. Both the selective and blocking approaches are likely compatible in a single probe panel and workflow format.

Methods for Detection of a Target RNA without Conversion to cDNA.

Analysis of RNA often suffers from a bias due to its conversion to cDNA prior to analysis. The methods described herein are directed to direct detection of a target RNA without conversion to cDNA. Detection of a target RNA includes but is not limited to interrogation of the exon boundaries which allows for detection of alternative splicing and splice variants of mRNA transcripts, detection of fusion genes (at least portions of two separate genes), and more general expression analysis of detecting expression of mRNA transcripts. In certain embodiments, the methods for detection of a target RNA utilizes next generation sequencing and enables the simultaneous detection of hundreds of thousands of RNA samples for tens to thousands of loci. The method for detection of a target RNA is based on ligation dependent PCR amplification and uses interrogation site probes as well as sample index barcodes that are added during PCR amplification. In exemplary embodiments, the utility of this method is demonstrated by performing a highly multiplexed reaction that uses a commercially available DNA ligase to ligate DNA probes hybridized to RNA templates. The ligation products are PCR amplified. Next generation sequencing data is generated from the resulting PCR products. Each read is assigned to a sample (based on the sample index) and to a locus. Examination of the sequencing data generated from the PCR products will reveal splice variants or fusion genes of mRNA transcripts, as well as the expression of mRNA transcripts. In Example 13 and FIGS. 19-21, the results of a 778-plex panel of probes designed to interrogate the RNA produced from housekeeping genes and from human gene exons selected for cancer fusion gene detection are shown. The expected exon junctions were found in the house-keeping genes. As described herein, the methods (and associated data analysis) for detecting and interrogating RNA targets are used in targeted studies of expression analysis, allele-specific expression analysis, alternative splicing analysis, and fusion gene detection. This method of direct detection of RNA is a simplified assay that also removes the RNA to cDNA conversion bias.

Sequencing-Based Detection

In one exemplary application of the methods, a sequence determination is performed using next generation sequencing, for example, Illumina sequencing. Product polynucleotides may be directly sequenced, or a copy of the product polynucleotide, or its complement generated in the assay may be sequenced. In carrying out the method, the first and/or second complementary probes may comprise a universal primer sequence. In such cases, the adapters for attaching product polynucleotides to an Illumina flow cell for sequencing may be added to the product polynucleotides (or reaction products) by PCR or another method of copying and/or amplifying product polynucleotides. The flow cell adapters may also be added to the product polynucleotides according to other techniques known in the art, e.g., ligation.

In some embodiments, an Illumina flow cell with eight or more lanes (HiSeq® flow cells) is employed as a solid phase support. Each lane can accommodate over 300 million amplified clusters and therefore can be used for high throughput analysis. In other embodiments, NextSeq® flow cells or other flow cells are used which accommodate different numbers of amplified clusters.

Sequencing techniques that may be used in the methods of the disclosure include next-generation sequencing techniques such as ion semiconductor sequencing (e.g. Ion Torrent sequencing), pyrosequencing (e.g. 454 sequencing), sequencing by ligation (e.g. SOLiD sequencing), sequencing by synthesis (e.g. Illumina sequencing) and single-molecule real-time sequencing (e.g. Pacific Biosciences).

Array-Based Detection

In some embodiments, the product polynucleotides described herein are detected using an array, e.g., for hybridization array-based analysis of product polynucleotides. Exemplary arrays include chip or platform arrays, bead arrays, liquid phase arrays, "zip-code" arrays, microarrays and the like. Materials suitable for construction of arrays such as nitrocellulose, glass, silicon wafers, optical fibers, etc. are known to those of skill in the art.

Kits

The disclosure provides kits comprising reagents for performing any of the methods disclosed herein.

In some embodiments the invention provides kits for determining the presence, absence or characteristics of one or more target polynucleotides in a sample and/or to determine a genotype. In some embodiments, the kit comprises a plurality of first and second complementary probes, each first complementary probe having a sequence portion that is complementary to a first target sequence, and a sequence portion that is non-complementary to the first target sequence wherein the non-complementary portion includes an interrogation site bar code sequence and an adjacent universal sequence, and each second complementary probe having a sequence portion that is complementary to a second target sequence and an adjacent sequence portion that is non-complementary to said second target sequence together with buffers and enzymes and components for ligation and enrichment.

The first complementary probe may have a sequence 5' to the non-complementary interrogation site bar code of the first complementary probe that is complementary to the first target sequence and a sequence 3' to the non-complementary interrogation site bar code of the first complementary probe that is complementary to the first target sequence.

In some embodiments, the kit comprises at least one PCR primer, a polymerase and a set of dNTPs for purposes of enrichment/amplification.

In some embodiments, the kit comprises a ligase.

In some embodiments, the kit comprises a license to use the software needed to interpret the sequence data.

In some embodiments, the kit comprises instructions for use.

The first and second complementary probes may be provided in dried form (e.g. lyophilized). If provided in a dried form, the probes may be dried with a preservative e.g. trehalose.

Compositions

The disclosure provides compositions comprising reagents for performing any of the methods disclosed herein.

In some embodiments, a composition for detecting the presence, absence, absence, amount or characteristics of one or more targets in one or more samples is provided. The composition includes: a plurality of first and second complementary probes, (i) each first complementary probe having two sequence portions that are complementary to different sections of a first target sequence, and two sequence portions that are non-complementary to the first target sequence wherein the non-complementary portions include an interrogation site bar code sequence and an a universal sequence, and (ii) each second complementary probe having a sequence portion that is complementary to a second target sequence and an immediately adjacent sequence portion that is non-complementary to the second target sequence and includes a universal sequence. The first complementary probe comprises a sequence having two portions that are complementary to the target sequence both 3' and 5' of the interrogation site bar code. The composition may be solution-based or bound to a solid support or portions of both.

In some embodiments, part of the complementary portion of the first complementary probe is 5' of the non-complementary interrogation site bar code sequence and part of the first complementary probe is 3' of the non-complementary interrogation site bar code sequence. The non-complementary interrogation site bar code sequence may be referred to as "anchored" to the target by the 5' and 3' complementary sequences of the first complementary probe. The non-complementary interrogation site bar code sequence may be from about 10 to 16 nucleotides in length, for example, 10, 11, 12, 13, 14, 15, 16 nucleotides in length.

Bioinformatics

The sequences of the product polynucleotides may be determined either by direct sequencing or by sequencing of complementary sequences. The methods described herein may be used to generate sequencing data that can be analyzed by a mathematical algorithm to determine the presence or absence of particular SNPs, indels and other mutations, whether particular loci are heterogeneous or homogeneous, whether a particular transcript is present or absent, the copy number of specific target polynucleotides, and/or other characteristics of the target polynucleotides.

In some cases, the genotype of samples can be determined by analyzing the number of reads assigned (via comparison of the interrogation site bar code) to each allele (at that locus) and determining if for each sample the ratio of the number of reads assigned to the A allele and the number of reads assigned to the B allele, indicate that the genotype of the sample is AA, AB, BB or unable to determine.

Utility

The compositions, methods and kits described herein are useful to analyze large numbers of samples for the presence, absence, amount or characteristics of multiple target polynucleotides in a single assay.

Typically, many sets of first and second complementary probes are provided in a single assay as a means to evaluate the presence, absence, amount or characteristics of multiple sequences, e.g., polymorphisms in a single assay. In some embodiments, multiple polymorphisms are determined for a plurality of samples in a single assay. In some embodiments, the compositions, methods and kits described herein find utility in genotyping and may involve next generation sequencing (NGS) technology in order to simultaneously generate a genotype for large numbers of both samples and loci in a single assay.

Paragraphs of the Disclosure

1. A method for determining the presence, absence or amount of one or more target polynucleotides in two or more samples, comprising the steps of:
   (a) providing two or more samples, each sample comprising one or more target polynucleotides, each target polynucleotide comprising a first target sequence and a second target sequence;
   (b) providing a plurality of first and second complementary probes, (i) each first complementary probe having a sequence portion that is complementary to a first target sequence, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence and an immediately adjacent sequence portion that is non-complementary to said second target sequence;
   (c) incubating said plurality of first and second complementary probes with each independent sample under hybridization conditions such that first and second complementary probes hybridize to their complementary target polynucleotide in a sample to form a hybridization complex;
   (d) joining first and second complementary probes that are hybridized to first and second target sequences in a sample to form a product polynucleotide;
   (e) pooling product polynucleotides formed from independent samples; and
   (f) determining the presence or absence of target polynucleotides in one or more samples by analyzing product polynucleotides or the complement thereof.

2. The method according to paragraph 1, wherein the first and second complementary probes are complementary to first and second target sequences immediately adjacent one another.

3. The method according to paragraph 1, wherein when first and second complementary probes are complementary to first and second target sequences that are adjacent and from 1 to 500 nucleotides apart.

4. The method according to any one of paragraphs 1-3, wherein the immediately adjacent non-complementary portion of said second complementary probe comprises a universal sequence.

5. The method according to any one of paragraphs 1-4, wherein the adjacent universal sequence of said first complementary probe comprises a universal primer sequence that is complementary to a priming sequence which can be used to add one or more of (i) a sample index, (ii) an additional sequence for sequence data generation or another form of detection, (iii) additional sequences, or (iv) other moieties.

6. The method according to paragraph 4, wherein the immediately adjacent universal sequence of said second complementary probe comprises a universal primer sequence that is complementary to a primer sequence which can be used to add one or more of (i) a sample index, (ii) an additional sequence for sequence data generation or another form of detection, (iii) additional sequences, and (iv) other moieties.

7. The method according to any one of paragraphs 1-6, wherein there is a sequence 5' to the non-complementary interrogation site bar code of the first complementary probe that is complementary to the first target sequence and a sequence 3' to the non-complementary interrogation site bar code of the first complementary probe that is complementary to the first target sequence.

8. The method according to any one of paragraphs 1-6, wherein there is a sequence that is complementary to the target sequence both 3' and 5' of the interrogation site bar code.

9. The method according to any one of paragraphs 1-8, wherein the adjacent universal sequence of said first complementary probe is 5' to the complementary sequence that is 5' to the non-complementary interrogation site bar code of the first complementary probe.

10. The method according to any one of paragraphs 5-9 wherein the universal primer sequence includes a PCR priming sequence and a primer sequence to add additional sequences for use in sequence data generation or other forms of detection.

11. The method according to paragraph 10, wherein the additional sequence for sequence data generation or another form of detection is an adapter for next generation sequencing.

12. The method according to paragraph 10, wherein the additional sequence for sequence data generation or another form of detection is a capture probe, for capture on a solid surface.

13. The method according to any one of paragraphs 5-12, wherein the primer sequence is effective to add a moiety useful for sequence generation.

14. The method according to any one of paragraphs 1-13, wherein the non-complementary interrogation site bar code is 10, 11, 12, 13, 14, 15 or 16 nucleotides in length.

15. The method according to any one of paragraphs 5-14, wherein the sample index is 10, 11, 12, 13, 14, 15 or 16 nucleotides in length.

16. The method according to paragraph 14, wherein the interrogation site bar code is 12 or 15 nucleotides in length.

17. The method according to paragraph 15, wherein the sample index is 12 or 15 nucleotides in length.

18. The method according to any one of paragraphs 1-17, wherein the interrogation site bar code or the sample index sequence is selected from the group consisting of SEQ ID NO: 1-SEQ ID NO:384.

19. The method according to any one of paragraphs 1-18, wherein there is a step before incubating that comprises heating at a temperature of from 70 to 100° C.

20. The method according to any one of paragraphs 1-19, further comprising enriching said product polynucleotides prior to the pooling step.

21. The method according to paragraph 20, wherein said enriching comprises, (a) providing a set of PCR priming sequences comprising a first primer that is complementary to a priming sequence on the first complementary probe, and a second primer that is complementary to a PCR priming sequence on the second complementary probe, and (b) amplifying the product polynucleotide.

22. The method according to any one of paragraphs 1-21, wherein the method is solution-based.

23. The method according to any one of paragraphs 1-22, wherein the first complementary probe comprises an inosine 2, 3, 4, 5, 6, 7, 8, 9, 10, or more bases from the 3' end of the probe.

24. The method according to any one of paragraphs 1-23, wherein the second complementary probe comprises an inosine 2, 3, 4, 5, 6, 7, 8, 9, 10, or more bases from the 5' end of the probe.

25. The method according to any one of paragraphs 1-24, wherein first and second complementary probes are complementary to first and second target sequences, and the 3' end of the first complementary probe is complementary to one form of a single nucleotide polymorphism (SNP) or other genetic variation.

26. The method according to any one of paragraphs 1-25, wherein means for joining is treating the first and the second complementary probes that are hybridized to first and second target sequences (hybridization complex) to form a product polynucleotide using a ligase.

27. The method according to any one of paragraphs 1-26, for use in genotyping, comprising providing one or more variants of the first complementary probe, wherein the variants differ in the identity of the nucleotide or nucleotides at the 3' end of the first complementary probe, wherein said determining comprises quantifying the relative frequencies of the one or more variants of the first complementary probe compared to the other variants of said first complementary probe and correlating said frequencies with a genotype.

28. The method according to any one of paragraphs 1-27, for use in determining the copy number variation of a target polynucleotide, wherein said determining comprises comparing the amount of signal produced for a product polynucleotide or the complement thereof to a known reference or to the amount of signal produced by another product polynucleotide or the complement thereof.

29. A composition for determining the presence, absence or amount of one or more target polynucleotides in a sample, comprising: a plurality of first and second complementary probes, (i) each first complementary probe having two sequence portions that are complementary to different sections of a first target sequence, and two sequence portions that are non-complementary to the first target sequence wherein the non-complementary portions include an interrogation site bar code sequence and a universal sequence, and (ii) each second complementary probe having a sequence portion that is complementary to a second target sequence and an immediately adjacent sequence portion that is non-complementary to the second target sequence and includes a universal sequence.

30. The composition according to paragraph 29, wherein said first complementary probe comprises a sequence 5' to the non-complementary interrogation site bar code of the first complementary probe that is complementary to the first target sequence and a sequence 3' to the non-complementary interrogation site bar code of the first complementary probe that is complementary to the first target sequence.

31. The composition according to paragraph 29, wherein said first complementary probe comprises a sequence that is complementary to the target sequence both 3' and 5' of the interrogation site bar code.

32. The composition according to any one of paragraphs 29-31, wherein the universal sequence of said first and second complementary probes each comprises a priming sequence that can hybridize to a primer for sequence synthesis.

33. The composition according to paragraph 32, wherein the priming sequence includes a PCR priming sequence.

34. The composition according to any one of paragraphs 29-33, wherein the universal sequence includes a priming sequence that allows the addition of one or more of (a) a sample index, (b) additional sequences, (d) an additional sequence for use in sequence data generation or other forms of detection, and (e) other moieties.

35. The composition according to any one of paragraphs 29-34, wherein the adjacent universal sequence of said first complementary probe is 5' to the complementary sequence that is 5' to the non-complementary interrogation site bar code of the first complementary probe.

36. The composition according to paragraph 34, wherein the universal sequence is a PCR primer sequence.

37. The composition according to paragraph 34, wherein the additional sequence for sequence data generation or another form of detection is an adapter for next generation sequencing.

38. The composition according to paragraph 34, wherein the additional sequence for sequence data generation or another form of detection is a capture sequence.

39. The composition according to any one of paragraphs 29-38, wherein the universal sequence includes a priming sequence that provides for the addition of a sample index.

40. The composition according to any one of paragraphs 29-39, wherein the interrogation site bar code or is 10, 11, 12, 13, 14, 15 or 16 nucleotides in length.

41. The composition according to paragraph 39 or paragraph 40, wherein the sample index is 10, 11, 12, 13, 14, 15 or 16 nucleotides in length.

42. The composition according to paragraph 40, wherein the interrogation site bar code is 12 or 15 nucleotides in length.

43. The composition according to paragraph 41, wherein the sample index is 12 or 15 nucleotides in length.

44. The composition according to any one of paragraphs 39-43, wherein the interrogation site bar code or the sample index sequence is selected from the group consisting of SEQ ID NO: 1-SEQ ID NO:384.

45. The composition according to any one of paragraphs 29-44, wherein the first complementary probe comprises an inosine 2, 3, 4, 5, 6, 7, 8, 9, 10, or more bases from the 3' end of the probe.

46. The composition according to any one of paragraphs 29-45, wherein the second complementary probe comprises an inosine 2, 3, 4, 5, 6, 7, 8, 9, 10, or more bases from the 5' end of the probe.

47. A kit for determining the presence, absence, amount or characteristics of one or more target polynucleotides in a sample comprising:
(a) a plurality of first and second complementary probes,
(i) each first complementary probe having a sequence portion that is complementary to a first target sequence, and a sequence portion that is non-complementary to the first target sequence wherein the non-complementary portion includes an interrogation site bar code sequence and an adjacent universal sequence, and (ii) each second complementary probe having a sequence portion that is complementary to a second target sequence and an immediately adjacent sequence portion that is non-complementary to said second target sequence; and
(b) buffers and enzymes for ligation and enrichment.

48. The kit according to paragraph 47, further comprising, at least one PCR primer, a polymerase, and a set of dNTPs to amplify extended target polynucleotides for purposes of enrichment.

49. The kit according to paragraph 47 or paragraph 48, further comprising a ligase.

50. The kit according to any one of paragraphs 47-49, further comprising software needed to interpret the data.

51. The kit according to any one of paragraphs 47-50, for determining a genotype.

52. The kit according to any one of paragraphs 47-51, for determining copy number.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Nucleic Acid Analysis by Joining Barcoded Polynucleotide Probes

Performing nucleic acid analysis by joining barcoded polynucleotide probes is accomplished by providing two complementary probes that hybridize to two portions (the first target sequence and the second target sequence) of a target polynucleotide (FIG. 1A). The first and second complementary probes may be immediately adjacent or separated by 1 to 500 or more nucleotides.

The first complementary probe contains a short interrogation site bar code (as shown in FIG. 1A; thin line) that further differentiates one first complementary probe from another version of the first complementary probe (FIG. 1E) or other first complementary probes. This interrogation site bar code permits the locus information and allele information (or only the locus information or only the allele information) to be determined from short uniform size reporter sequence. In the case of assay results produced using next generation sequencing, the addition of a sequence portion complementary to the target 5' to the interrogation site barcode also places the interrogation site bar code in a position to have high quality sequence data. The interrogation site bar code may contain information about the locus only, the allele only, the locus and allele combined or the locus and allele as separate sequences. The use of the interrogation site bar code allows the sequence that reports on a genetic locus to correlate with size, placement and nucleotide composition.

In the first complementary probe, the sequence that is complementary to the first target sequence (FIG. 1A; thick line) is interrupted into two portions by the interrogation site bar code. The interrogation site bar code is non-complementary to the first target sequence.

The first complementary probe may also contain a universal sequence (FIGS. 1A-D; dashed line). This universal sequence may be called "universal primer 1". This describes its common function as a PCR priming site. However, it is understood that the universal sequence may not have this function and may have other functions including but not limited to one or more of other forms of amplification and capture. The universal sequence may also serve to facilitate the addition of one or more of other sequences or of other moieties.

The second complementary probe has a sequence that is complementary to the second target sequence (FIG. 1A; thick line) and a universal sequence (FIG. 1A; dashed line). This universal sequence may be called "universal primer 2", which describes its common function as a PCR priming site. The universal sequence in the first and second complementary probes may or may not be the same sequence (or may or may not be complements of one another).

The first and/or second complementary probes may or may not further contain sequences for size adjustment.

The universal sequence is non-complementary to the target sequences.

Following hybridization of the first and second complementary probes with first and second target sequences that may or may not be present in the sample, the first complementary probe may or may not be extended to become immediately adjacent to the second complementary probe as there may be no gap between the first and second complementary probes, or there may be a gap of one or more bases between the first and second complementary probes that may be filled by a gap fill step.

Figure 1B:
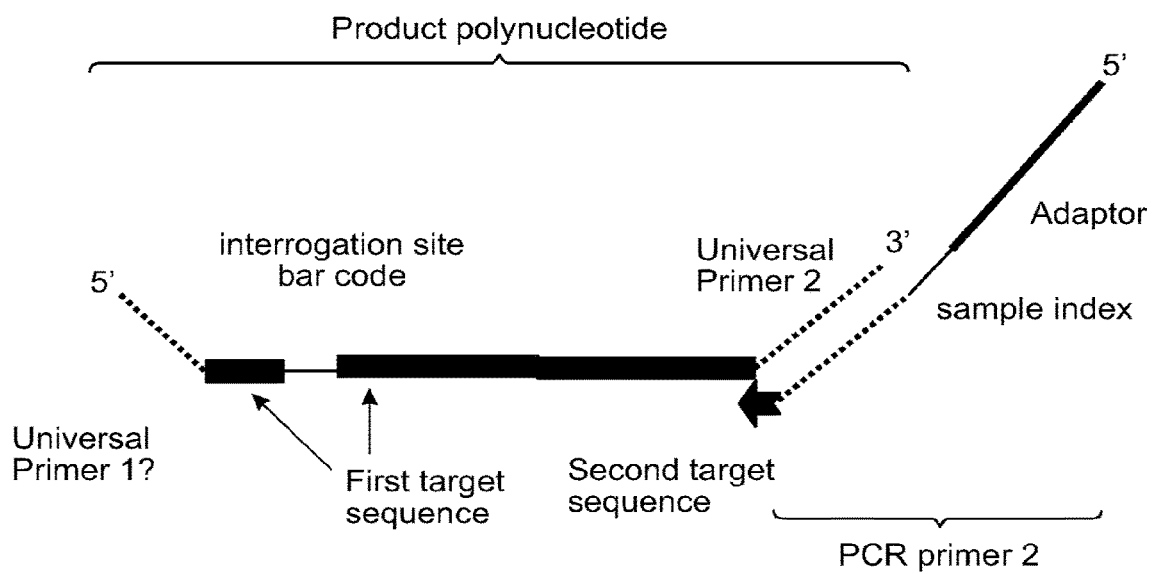

The immediately adjacent first and second complementary probes are joined (as shown in FIG. 1A, chevron) to generate a product polynucleotide (extending from the 5' universal primer 1 to 3' universal primer 2 in FIG. 1B).

This product polynucleotide is then the template for an amplification reaction or other form of enrichment (FIG. 1B). In this example, the enrichment is through a PCR reaction. Although other configurations are possible, as depicted here, PCR primer 2 has a portion that is the complementary sequence to universal primer 2 (from the second complementary probe), a portion that is a sample index sequence and a portion that is an adaptor sequence (medium line). DNA synthesis proceeds from the PCR primer 2 (closed arrow head in FIG. 1B) using the product polynucleotide as the template.

Figure 1C:
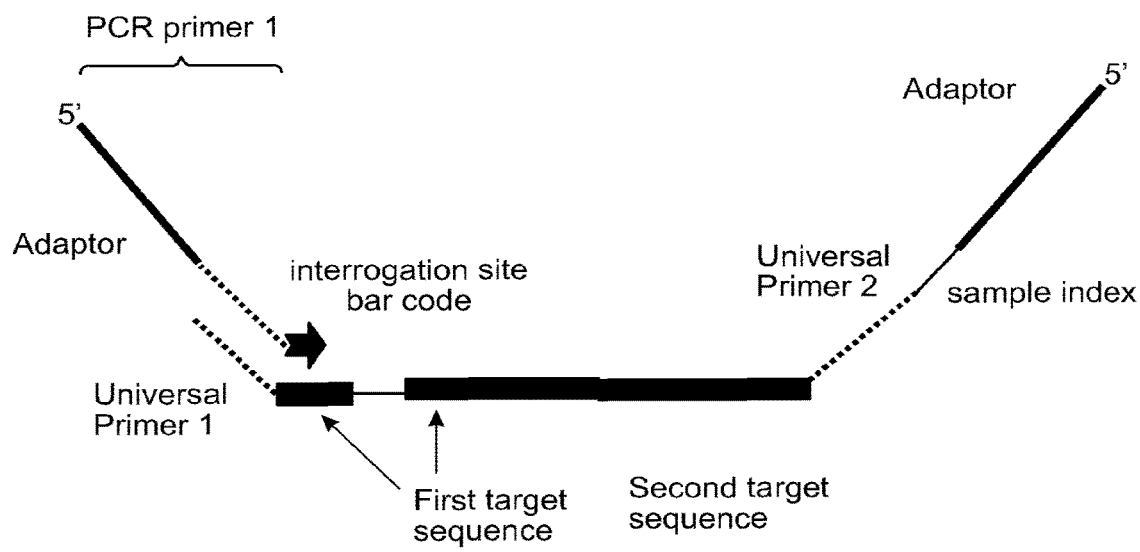

This amplification product is then the template for further amplification from (in this example) PCR primer 1 (FIG. 1C). Although other configurations are possible, as depicted here PCR primer 1 has a portion that is the complementary sequence to universal primer 1 (dashed line from the first complementary probe) and a portion that is an adaptor sequence (medium line). DNA synthesis proceeds from the PCR primer 1 (closed arrow head) using the product of the first round of amplification as the template. In certain embodiments, PCR primer 1 can also have a portion that is a sample index sequence similar to PCR primer 2 depicted in FIG. 1B.

In alternative embodiments the sample index (or portion thereof) is added with PCR primer 1. In other embodiments, the sample index is added in both PCR primer 1 and PCR primer 2. Through PCR primer 2 and/or PCR primer 1, a sample identification sequence (sample index) or other sample identification moiety is attached to each product polynucleotide. When a sample index is added to PCR primer 1, it is near the interrogation site bar code to facilitate sequencing of both the interrogation site bar code and the sample index while minimizing the total number of bases that need to be sequenced (e.g., without the need to sequence the first and second target sequences that would otherwise be between the interrogation side bar code and the sample index if the sample index was at least partially added with PCR primer 2).

Figure 1D:
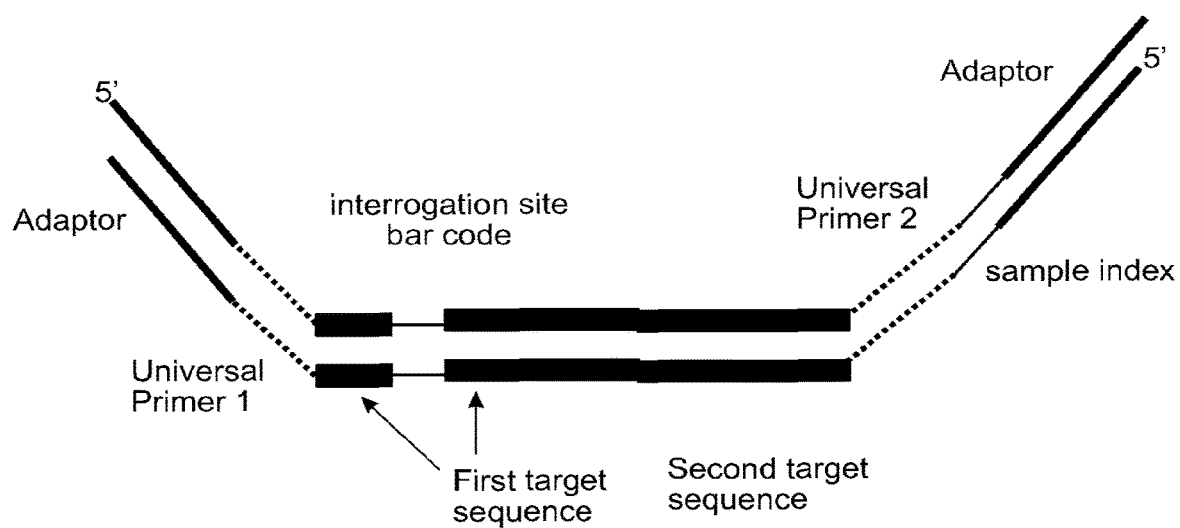
Figure 1E:
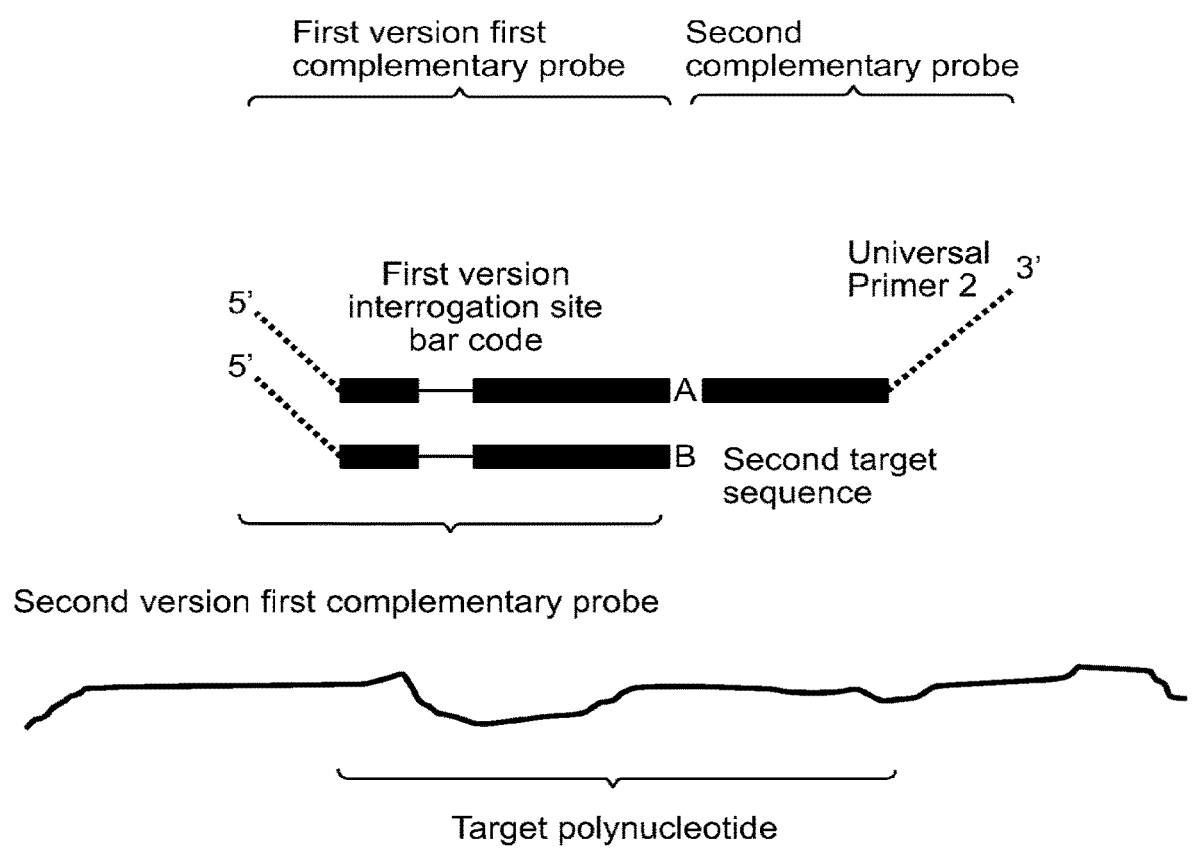

The two rounds of DNA synthesis (FIGS. 1B and 1C) result in a double stranded amplicon as depicted in FIG. 1D. In this example, more copies of this amplicon are generated through additional rounds of amplification using PCR primer 2 and 1 to prime the DNA synthesis.

Further, in this example, sequence data is generated on portions of each amplicon (or the entire amplicon). There may or may not be portions of each amplicon where no sequence data is generated. Each sequence produced is compared to a database to assign to the appropriate sample and allele and/or locus. Mis-assignments can occur due to various factors including, but not limited to, sequence error, polymerase error and non-specific joining. The tabulated number of reads is analyzed to determine presence, absence, amount or copy number of the target sequence, SNP, or genetic locus.

In a further example (FIG. 1E), there are two or more versions of the first complementary probe. Each version has a different sequence at the 3' end (depicted A and B). This different sequence may be one or more bases. In extreme cases (for example, detection of large deletions or complex indels), the two versions of the first complementary probes are complementary to completely different versions of first target sequences. The two or more versions of the first complementary probes are between these two extremes and retain the other elements of first complementary probes. Although there are other uses, including but not limited to examination of contamination or portion of an admixture or quasi-species or hetero-resistance, the multiple versions of first complementary probes is commonly used to generate classic genotype information. In this case, for each sample and locus, the number of reads assigned to the A allele and the number of reads assigned to the B allele are compared. For each locus and taking into account the ratio of the number of reads assigned to the A allele relative to the number of reads assigned to the B allele (and mis-assignments), a sample that has reads that are predominately assigned to the A allele is AA, a sample that has reads that are predominately assigned to the B allele is BB, and a sample that has a significant number or reads assigned to both alleles is AB. These A and B nomenclatures are only for discrimination and do not reference any convention on a nucleotide sequence associated with the A or B allele.

Example 2. Interrogation Site Bar Code with Complementary Sequence on Both Sides In carrying out a nucleic acid analysis by joining barcoded polynucleotide probes assay, there are various positions in the first complementary probe where the interrogation site bar code can be placed. It can be placed within the universal sequence, it can be placed between the universal sequence and the target specific sequence (as is common in prior art methods such as disclosed in U.S. Pat. No. 8,460,866), and it can be placed within the target specific sequence, as exemplified herein. When the interrogation site bar code is placed within the target specific sequence and is non-complementary to the target polynucleotide, there are complementary sequence portions on both sides of the interrogation site bar code. When the allele and locus information (or in some cases only the locus information) is encoded in the interrogation site bar code, there is the benefit of controlling the degree of sequence difference that is used to detect the target polynucleotides in multiplex reactions. In such cases, the detection does not rely on sufficient differences between the target polynucleotide sequences. The results from the assay with a probe component (PC) that contained 130 probe triplets (two forms of the first complementary probe and one form of the second complementary probe) with 6mer interrogation site bar codes placed between the target specific sequence and the universal sequence were compared to the results from the assay with a PC that contained 130 probe triplets for the same target polynucleotides and variants with 12mer interrogation site bar codes placed within and non-complementary to the target specific sequence (such that in the first complementary probes there are complementary sequence portions on both sides of the interrogation site bar code). The probes in PC are at 50 pM each. In the 12mer probe design, the complementary portion was increased on the 5' end by several bases (12 bases away from the rest of the complementary region). In the 6mer, 12mer design, the complementary region 3' of the 6mer, or 12mer interrogation site bar code, was identical in size and composition. Further, in the 12mer, the 12 base non-complementary interrogation site bar code contains the information for the allele and the locus combined. In the 6mer, the 6 base non-complementary interrogation site bar code contains the information for the allele. The information to assign the read to a locus is the sequence of the target sequence (and would be similarly contained in the database).

Bovine genomic DNA (50 ng/ul) from individual samples was placed in wells of multiwall plate and heated to 98° C. for 15 minutes. Following this a portion of each sample was transferred to a new plate and mixed with a PC (12mer). These reactions were then melted at 98° C. for 1 minute and then incubated at 60° C. for 20° hours for hybridization. After hybridization 3.2 ul of the reaction was added to a waiting plate containing 12.8 ul of NEB 1×Taq DNA ligase buffer together with Taq DNA ligase enzyme. The new plate was sealed, reactions mixed, centrifuged and then held at 54° C. for 15 minutes followed by 98° C. for 10 seconds and brought to 4° C. and held. One ul of this completed ligation reaction was used in PCR reactions containing Promega GoTaq Hotstart Taq PCR in a 12.5 ul total volume, 1× buffer, dNTP, 0.3 uM and PCR primers 1 and 2. A total of 32 cycles of 65° C./95° C. for 20 seconds/15 seconds was completed after which all the reactions were combined and processed through a single Zymo-100 silica column and eluted in a 150 ul TE8.0 volume. The pooled library was then quantified by Bioanalyzer 2100 trace, diluted to appropriate fraction of an Illumina Next500 flow cell, and sequence data was generated.

Figure 2A:
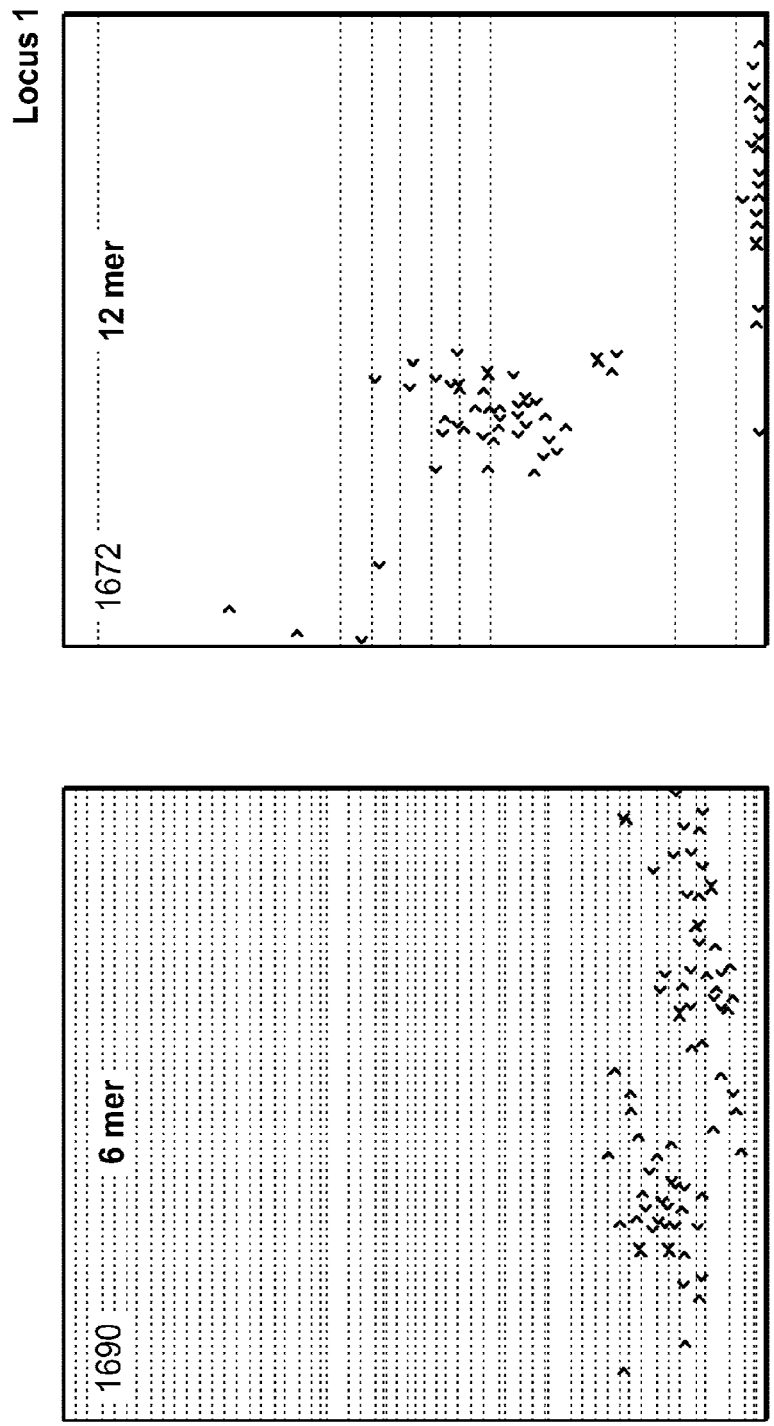
Figure 2B:
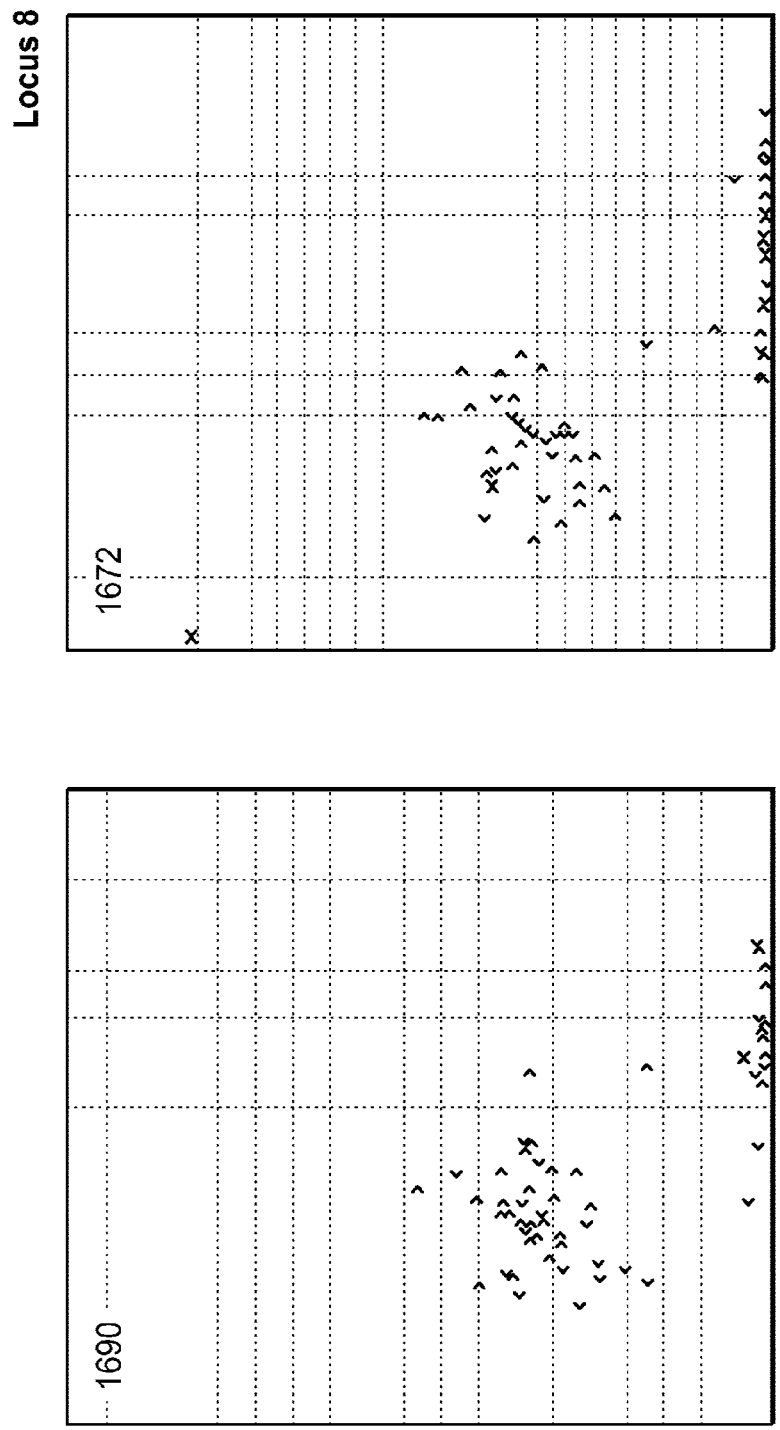

The sample index sequence and the interrogation site bar code (and as needed other sequences) contained in each read was compared to a database, and the number of reads created from each sample×locus×allele was tabulated (and includes mis-assigned reads). For each locus the number of reads from the A allele (X-axis) and the number of reads of the B allele (Y-axis) for each sample was plotted. This A allele vs B allele plot is called a cluster plot, as shown in FIGS. 2A-C.

The above standard protocol was also performed with the PC of the 6mer probes and an aliquot of the DNA that had been heated to 98° C. for 15 minutes.

Overall, the results indicated a similar ability to produce genotypes from a PC that has first complementary probes with the interrogation site bar code between the universal sequence and the target sequence (between), or from a PC that has first complementary probes with the non-complementary interrogation barcode within the target sequence (such that there are complementary sequence portions on both sides of the interrogation barcode). While locus by locus differences were observed, the location and type of an interrogation site bar code (where the interrogation site bar code is placed and the information that is not-complementary to the target sequence) information on the locus and allele did not alter the characteristics of the genotyping cluster plots. Some differences between results obtained with PC that contained the 6mer, and 12mer designs, are likely differences in the effective probe concentrations (full length species) that are a non-uniformity caused by the manufacturer, other differences are due to the greater ability of the 12mer design to ensure that similar target sequences are not mistaken for each other.

Example 3. Resolving G:T Mismatches in Genotyping Assay

It is known by those of skill in the art that ligation based assays have a lower specificity when a T:G mishybridization ("mismatch") occurs at the 3' end of the SNP interrogating sequence and the target sequence. This occurs when a G/A SNP is being detected. In the case of a genotyping assay, this can be an issue when there is a C at the 3' end of the first version of a first complementary probe (e.g., first complementary probe #1) and a T at the 3' end of the second version of the first complementary probe (e.g., first complementary probe #1'). The correct first version of the first complementary probe ligation is on a target polynucleotide that has a G at the SNP site in the target polynucleotide and incorrect first version of the first complementary probe ligation is on a target polynucleotide that has an A at the SNP site in the target polynucleotide The correct second version first complementary probe ligation is on a target polynucleotide that has an A at the SNP site in the target polynucleotide and an incorrect second version first complementary probe ligation is on a target polynucleotide that has a G at the SNP site in the target polynucleotide. To one skilled in the art, a similar T:G mishybridization is possible when a C/T SNP is being detected. The partial hydrogen bonding between the described G:T "mismatched" nucleotide is sufficiently stable to permit the ligase to (inefficiently) join the mismatched first complementary probe to the second complementary probe. This results in a non-specific target polynucleotide occurring 0-25% of the time. To minimize this signal, a universal base, deoxyinosine, was employed proximal to the interrogating 3' position of the affected first complementary probe. Deoxyinosine inclusions at the 2nd, 3rd, 4th, 5th, 6th, 7th, 8th, or $9^{th}$ position from the 3' end of the affected version of the first complementary probe, destabilizes the G:T mismatch and thus decreases the likelihood (and frequency) of non-specific product polynucleotide production. When deoxyinosine is at the second 3' position of the affected version of the first complementary probe, the G:T mismatch causes sufficient instability such that it minimizes incorrect ligations and non-specific product polynucleotides are produced less frequently. A deoxyinosine in the unaffected version of the first complementary probe does not destabilize hybridization sufficiently to impact genotype resolution, and the ligation reaction proceeds in a (largely) specific manner and specific product polynucleotides are produced. As the position of the deoxyinosine moves to the 5' side of the first complementary probe, its ability to reduce the stability of the G:T mismatch decreases. When the inosine is at the $10^{th}$ position from the 3' end, the production of next generation sequencing reads from the non-specific product polynucleotide is essentially equal to that of a non-deoxyinosine containing affected or incorrect version of the first complementary probe. An ideal position of the deoxyinosine to reduce mismatched ligation is the $2^{nd}$, $3^{rd}$ or $4^{th}$ 3' base.

In this example deoxyinosine is included at 3' positions 2 through 10 (inosine substitution for the base that was present) of the affected version of the first complementary probe (there is a T at the 3' end). This results in ten versions of the affected form of the first complementary probe. Probe components with one inosine placement of the affected version of the first complementary probe, the non-affected version of the first complementary probe and the second complementary probe (all for the target polynucleotide) were made to 50 pM along with probe buffer. A single bovine gDNA sample (50 ng/uL) was heat fragmented for 20 min at 98° C., and then 5 ul was filled into wells. Each probe mix then filled four wells. The NGG reactions were then heated to 98° C. for one minute and then brought to 60 C for 20 hours. After the hybridization 3.2 ul of the reaction was added to an awaiting plate containing 12.8 ul of NEB 1×Taq DNA ligase buffer and Taq DNA ligase enzyme. The new plate was sealed, mixed, centrifuged and then held at 54° C. for 15 minutes followed by 98° C. for 10 seconds and brought to 4° C. and held. One ul of this completed ligation reaction was used in PCR reactions containing Promega GoTaq Hotstart Taq PCR in a 12.5 ul total volume, 1× buffer, dNTP, 0.3 uM first and second universal primers. A total of 32 cycles of 65° C./95° C. for 20 sec/15 sec was completed after which all the reactions were combined and processed through a single Zymo-100 silica column and eluted in a 150 ul TE8.0 volume. The pooled library was then quantified by Bioanalyzer 2100 trace, diluted to appropriate fraction of an Illumina Next500 flow cell, and sequence data generated. The sample index sequence and the allele and locus barcode sequence contained in each read was compared to a database, and the number of reads created from each sample× locus×allele (even though this includes non-specific reads) was tabulated. The results are shown in FIG. 3.

Figure 3:
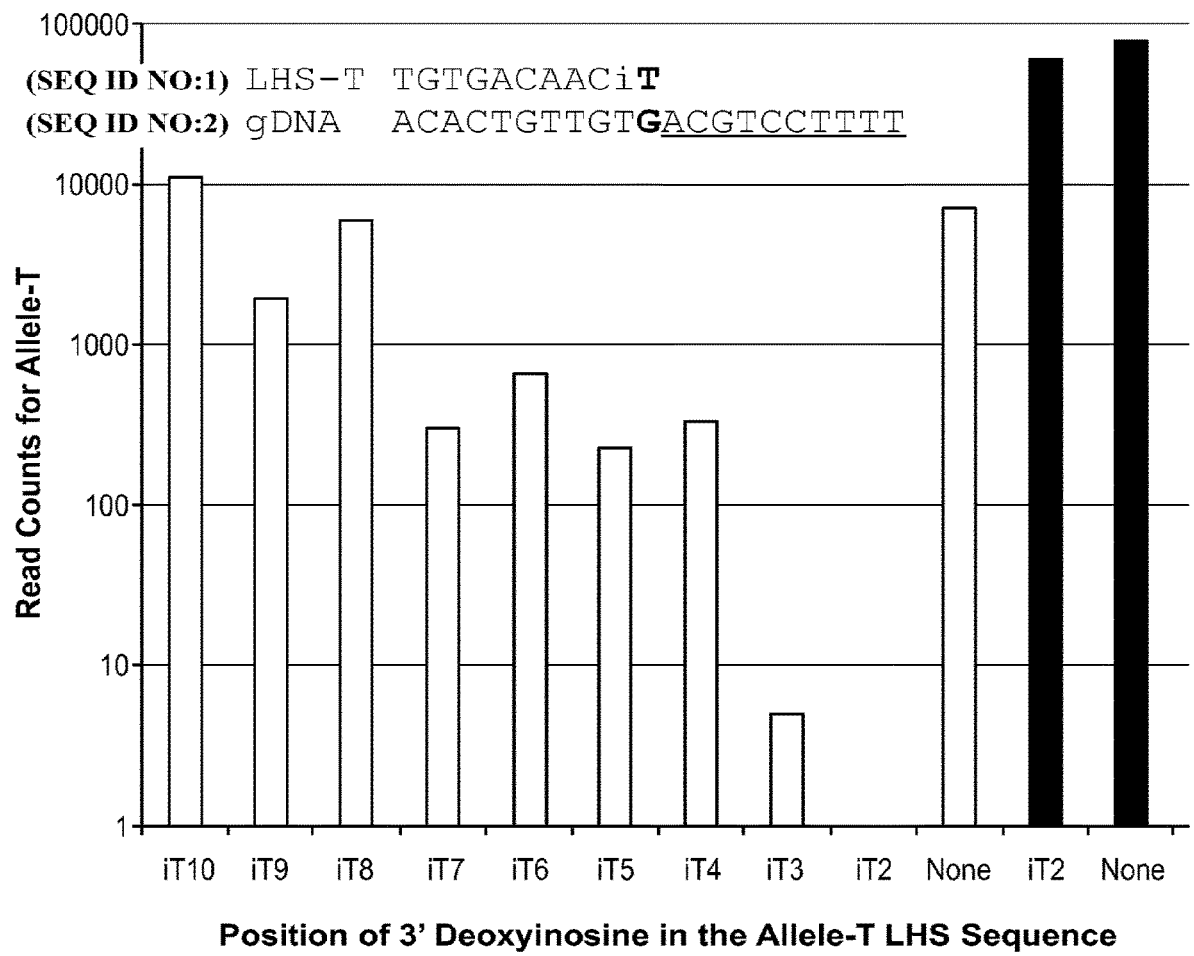
FIG. 3 illustrates the results of a study where deoxyinosine was used to alleviate the effects of G:T mismatches for probe triplets in a genotyping assay embodiment. A probe that suffered from severe G:T mismatch effects was modified by placing deoxyinosine at the 2nd to 10th 3' positions of the affected version of the first complementary probe (none, iT2 to iT10). The sequence model (where LHS-T (the first complementary probe) for the affected version of the first complementary probe is shown in the 5' to 3' direction, and the target gDNA or genomic DNA is shown in the 3' to 5' direction) shows the 10 most 3' positions of the first complementary probe containing the 3' T nucleotide mismatched to the G nucleotide in the genomic DNA sequence. A second 3' position (i) is shown corresponding to the "iT2". The underlined portion of the gDNA sequence is where the second complementary probe would hybridize. Solid grey bars are samples that are homozygous GG, striped bars represent samples that are homozygous AA. The Y-axis is the log scale of the number of reads associated with the T version of the first complementary probe. The grey bars (homozygous GG samples) represent non-specific ligation due to the stability of the G:T mismatch. The stripped bars (homozygous AA samples) represent specific ligation. The results show that deoxyinosine placement at the 2nd or 3rd 3' position of the modified version of the first complementary probe significantly reduces the number of reads from non-specific ligation. Similarly, the deoxyinosine can be used in first complementary probes that have a 3'G and the potential for the G:T mismatch.
Figure 6A:
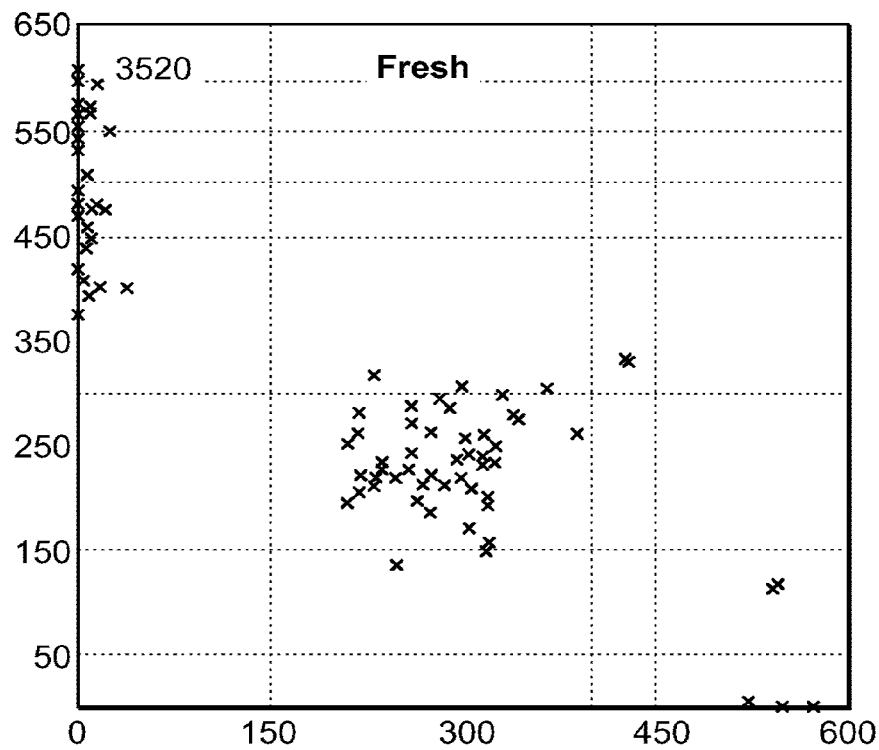
FIGS. 6A-6D illustrates the effect of various storage methods on reaction outcome of a genotyping assay embodiment using cluster plots of a single locus and four probe component storage treatments. The plots are of a probe component that is freshly prepared (FIG. 6A), frozen (FIG. 6B), dried (FIG. 6C), and dried with trehalose sugar (FIG. 6D). The number of reads for Allele-A (x-axis) and Allele-B (y-axis) are shown where each point is a unique sample (with the same 96 samples in each treatment). AA animals are along the x-axis, BB animals are along the y-axis, and AB animals are centered between the axes. While the plots for fresh, frozen and dried with trehalose are similar, the plot of dried without trehalose shows less resolution of the three genotypes.
Figure 6B:
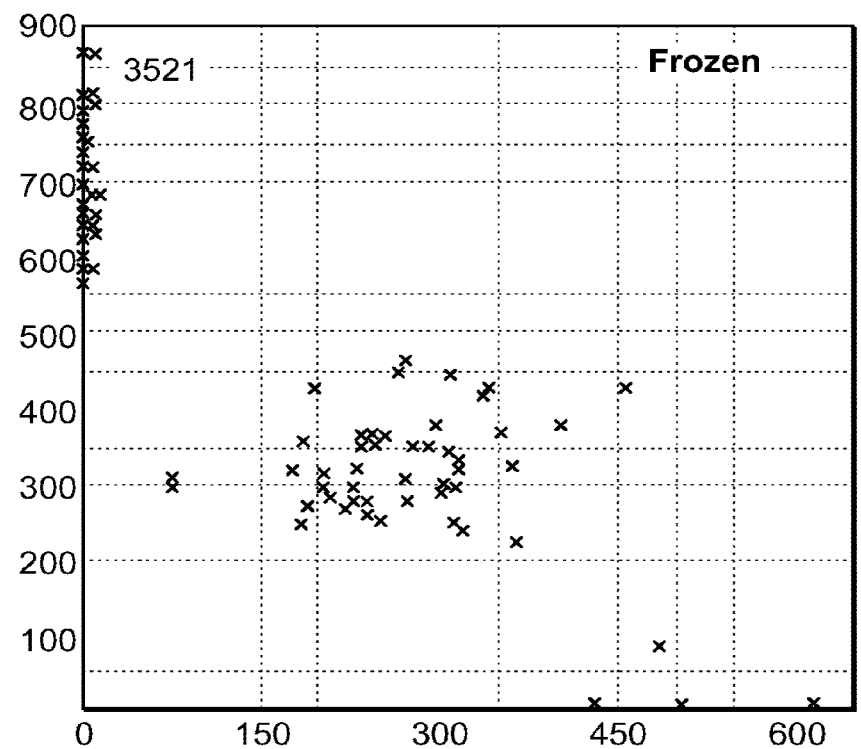
Figure 6C:
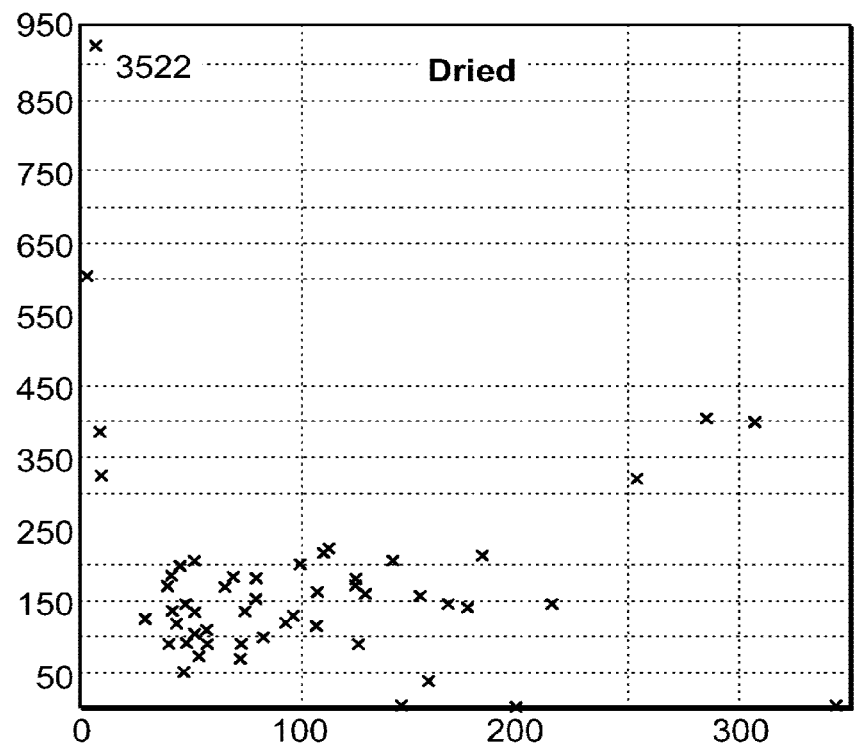
Figure 6D:
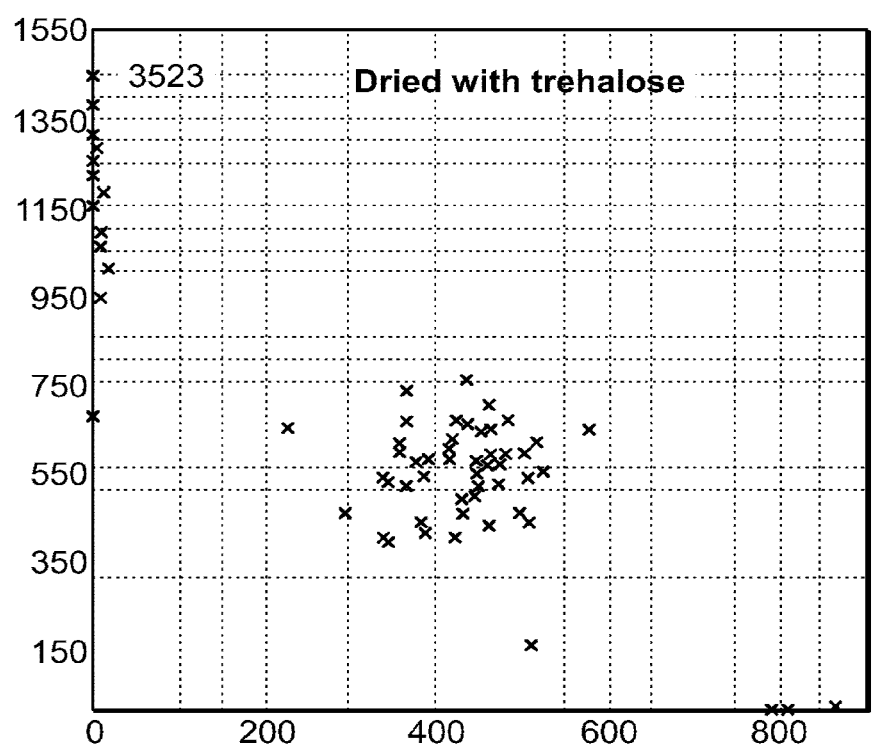

In FIG. 3 the sequence model (LHS-T or the affected form of the first complementary probe is 5' to 3', and target gDNA or genomic DNA is 3' to 5') shows the 10 most 3' positions of the first complementary probe containing the 3' T nucleotide (none, iT2 to iT10) and is shown mismatched to the G nucleotide in the genomic DNA sequence. A second 3' position (i) is shown corresponding to the "iT2". The underlined portion of the gDNA sequence is where the second complementary probe would hybridize. Solid grey bars are samples that are homozygous GG, striped bars represent samples that are homozygous AA. The Y-axis is the log scale of the number of reads associated with the T form of the first complementary probe. In the grey bars (homozygous GG samples) these are from non-specific ligation due to the stability of the G:T mismatch. In the striped bars (homozygous AA samples) the reads are from the specific ligation. The deoxyinosine placement at the $2^{nd}$ or $3^{rd}$ 3' position of the affected form of the first complementary probe significantly reduces the number of reads from non-specific ligation. Similarly the deoxyinosine can be used in first complementary probes that have a 3'G and the potential for the G:T mismatch.

Example 4. Methods for Detection of Target Polynucleotides in Large Excess of Background DNA Detection methods and associated data analysis are used to detect the presence of a target polynucleotide in samples containing DNA from multiple species and a large excess of non-target polynucleotide DNA. The detection methods (and associated data analysis) generates genotype information (SNP or other variation) and information on the amount of a target that is present in the sample. The effectiveness of one detection method was demonstrated in a model experiment where E. coli genomic DNA (background or "noise" DNA which was not being detected,) was mixed with varying amounts of target genomic DNA by titrating the target (or signal) genomic DNA (a single bovine sample) into the background E. coli genomic DNA. Noise was set at either 0, 125, or 250 ng/reaction and the signal was half fold diluted from 250, 125, 62.5 down to 0.12207 ng/reaction (a total of 12 concentrations) in TE buffer with a pH=8.3. The tubes were heated to 98° C. for 15 minutes to fragment the DNA. Each signal tube was used as the source for 5 ul samples which were transferred into each of 8 EG reaction wells in columns of a 96 well PCR plate. A probe component (PC) was created with sets of 135 probe triplets (two forms of the first complementary probe and one form of the second complementary probe) for genotyping bovine genomic DNA. The PC was mixed with 0, 125, or 250 ng/reaction of the noise E. coli genomic DNA. These PC+ E. coli mixtures were spread over the 96 well plate (250 ng/reaction in three rows 125 ng/reaction in three rows, and the 0ng/reaction in two rows). The reactions were then melted at 98° C. for 1 minute and then incubated at 60° C. for 20° hours for hybridization. After hybridization 3.2 ul of the reaction was added to a waiting plate containing 12.8 ul of NEB 1×Taq DNA ligase buffer together with Taq DNA ligase enzyme. The new plate was sealed, reactions mixed, centrifuged and then held at 54° C. for 15 minutes followed by 98° C. for 10 seconds and brought to 4° C. and held. One ul of this completed ligation reaction was used in PCR reactions containing Promega GoTaq Hotstart Taq PCR in a 12.5 ul total volume, 1× buffer, dNTP, 0.3 uM and first and second universal PCR primers. A total of 32 cycles of 65° C./95° C. for 20 seconds/15 seconds was completed after which all the reactions were combined and processed through a single Zymo-100 silica column and eluted in a 150 ul TE8.0 volume. The pooled library was then quantified by Bioanalyzer 2100 trace, diluted to appropriate fraction of an Illumina Next500 flow cell, and sequence data was generated.

The sample index sequence and the allele and locus barcode sequence (the interrogation site bar code) contained in each read was compared to a database, and the number of reads created from each sample×locus×allele was tabulated (and includes the mis-assigned reads) and genotypes determined. Data in relation to the amount of DNA and bovine genome equivalents is presented in FIGS. 4A and B and shows that the detection method can be used to detect polynucleotide targets in diploid eukaryotic genomes, even when the target signal genome accounts for under 0.1% of the total DNA. This can be extrapolated to the detection of microbial genomes in the background of eukaryotic genomes, detection of genomic fragments in complex food, environmental or other samples, detection of low amounts of RNA in cells, detection of adventitious presence of contaminating seeds and other applications.

Example 5. Reversible Denaturation Before Probe Hybridization Improves Cluster Plot Resolution Genotyping methods and associated data analysis require double or single stranded nucleic acid (NA) as the target polynucleotide. The first complementary probe and the second complementary probe require access to single stranded NA for hybridization to the target polynucleotide. The results of experiments have shown that to render double stranded and even single stranded NA accessible, the sample must be heated to a high temperature. Exemplary temperatures included a range of 70° C. to 100° C. and with heating times from 1 second to 15 minutes. This reversible denaturation step improves the detection of target polynucleotides (especially target polynucleotides that are present in the sample as double stranded).

An experiment was carried out using methods similar to those described in Example 2, using a probe component (PC) of 135 probe triplets (for genotyping) of bovine SNPs and 96 bovine genomic DNA samples. In one experiment, the DNA was heated to 98° C. for 15 minutes, the PC was added, mixed with the sample and then the sample and PC was heated (reversible denaturation) to 98° C. for 1 min, prior to the 60° C. and 20 hr hybridization step. In the second experiment, no heat was applied prior to the 20 hr hybridization step. In this experiment, the sample was not heated to 98° C. for 15 minutes and the PC and sample was not heated to 98° C. for 1 minute prior to 60° C. and 20 hr. hybridization. Post hybridization, the steps, were performed as described in Example 2, for ligation, PCR, and sample pooling.

The pooled library was then quantified by Bioanalyzer 2100 trace, diluted to appropriate fraction of an Illumina Next500 flow cell, and sequence data generated. The sample index sequence and the allele and locus barcode sequence contained in each read was compared to a database, and the number of reads created from each sample×locus×allele was tabulated (and includes mis-assigned reads). For each locus the number of reads from the A allele (X-axis) and the number of reads of the B allele (Y-axis) for each sample was plotted. The results are shown in FIGS. 5A and 5B.

Example 6. Genotyping Assay Using Dried Probe Components

The genotyping assay described herein consist of nucleic acids mixed with high salt concentrations and a blend of probes. The first and second complementary probes are in solution with each single probe being at 50 pM concentration in the "Probe Component" or "PC" (probes, TE, and hybridization buffer). This example demonstrates an improved method of setting up a genotyping assay reaction. It is desirable to place the probe component into a reaction well and dry it down and seal the plate, providing for long term (i.e., years), of room temperature storage. A set of 135 probe triplets (two forms of the first complementary probe and one form of the second complementary probe) for genotyping bovine genomic DNA, were dried in reaction wells. A single PC was created at the working concentration of 50 pM. 3 ul of the PC was placed in the wells of six columns of a 384 well plate. Another PC was prepared which contained the same 135 probe triplets, TE and buffer and 0.4 mM trehalose sugar. The trehalose sugar is a useful preservative of dried poly nucleic acids, and it secures the dried PC to the bottom of the reaction well. PC with trehalose was similarly used to add 3 ul to the wells in 6 columns of a 384 well plates. One of each plate PC type (with and without trehalose), was dried to completion by placing the plates in a laminar flow hood overnight, where sterile dust free air passed over the plates. One plate without trehalose plate was sealed and frozen at −20° C. for storage. The dried plates were sealed and stored at room temperature.

After one month, fresh PC was made and 3 ul was added to the wells in six columns of a 384 plate. A panel of 96 bovine genomic DNA samples at 50 ng/ul and 35 ul was heated for 98° C. for 15 minutes. The gDNA was then added to the four plates, 5 ul for the two wet plates (one fresh and one stored for a month at −20° C.) and 8 ul for the two dry plates (stored at room temperature for a month). All wells had 8 ul of volume. The plates were sealed, briefly centrifuged held at RT for 2 hours to ensure complete rehydration of dried probes. The reactions were then melted with a 98° C. for 1 minute and then held at 60° C. for 20 hours of hybridization. After the hybridization 3.2 ul of the reaction was added to each plate containing 12.8 ul of NEB 1×Taq DNA ligase buffer together with Taq DNA ligase enzyme. The new plate was sealed, mixed, centrifuged and then held at 54° C. for 15 minutes followed by 98° C. for 10 seconds and brought to 4° C. and held. One ul of this completed ligation reaction was used in PCR reactions containing Promega GoTaq Hotstart Taq PCR in a 12.5 ul total volume, 1× buffer, dNTP, 0.3 uM and first and second universal PCR primers. A total of 32 cycles of 65° C./95° C. for 20 seconds/15 seconds was completed after which all the reactions were combined and processed through a single Zymo-100 silica column and eluted in a 150 ul TE8.0 volume. The pooled library was then quantified by Bioanalyzer 2100 trace, diluted to appropriate fraction of an Illumina Next500 flow cell, and sequence data generated. The sample index sequence and the allele and locus barcode sequence contained in each read was compared to a database, and the number of reads created from each sample×locus×allele was tabulated (and includes mis-assigned reads). For each locus the number of reads from the A allele (X-axis) and the number of reads of the B allele (Y-axis) for each sample was plotted. The results are shown in FIGS. 6A-D.

In general the ability to generate genotypes from PC that is made fresh, or stored frozen or dried with trehalose and stored at room temperature are similar.

Example 7. Methods for Determining Copy Number Variation

The copy number analysis methods may be used to determine copy number variation (CNV) where zero copies of an allele are discriminated from one or two copies of the same allele. To demonstrate this, the next generation sequencing reads produced from a copy number analysis assay (96 bovine samples with normalized amount of input DNA across all the samples) were compared to the database appropriate for the interrogation site bar codes in that probe component and the sample index sequences. The number of reads created from each sample and a single allele of a single locus was tabulated (and includes mis-assigned reads) and analyzed. As shown in FIGS. 7A-C, animals that are BB homozygous have zero or near zero reads that have the interrogation site bar code for the A allele (at this locus). Animals that are AB heterozygous have around 200 reads that have the interrogation site bar code for the A allele (at this locus). Finally AA homozygous animals have around 400 reads that have the interrogation site bar code for the A allele. In this type of CNV assay the input nucleic acid needs to be consistent for the samples being tested or additional markers need to be used to adjust the number of reads produced within each sample (and/or for each genetic locus that is interrogated).

Example 8. Use of Genotyping to Evaluate a Tetraploid Genome

In tetraploid organisms, four copies of an allele can exist, one on each chromosome. To mimic a tetraploid organism, DNA from two different diploid animals (same species) was mixed together, producing a sample with four copies of any given allele. A probe component containing probe triplets (two forms of the first complementary probe and one form of the second complementary probe) for multiple target polynucleotides was added and the method was carried out as described in Example 2, except that the cluster plots allowed for five genotypes.

The sample index sequence and the interrogation site bar code sequence contained in each read was compared to a database, and the number of reads created from each sample×locus×allele was tabulated (and includes mis-assigned reads). For this locus the number of reads from the A allele (X-axis) and the number of reads from the B allele (Y-axis) for each sample were plotted. This experiment demonstrates the ability to distinguish five genotype groups and produce genotypes when the sample is or contains a tetraploid genome. The results are shown in FIG. 8.

Example 9. Genotyping Interrogation of Poly-Allelic Locus

Genotyping interrogation is able to genotype poly-allelic SNPs by the simple addition of a third, fourth or more form of the first complementary probe for the third, fourth or more alleles. For the detection of the possible genotypes at an exemplary tri-allelic SNP location, the probe component (PC) contained three nearly identical first complementary probes and a single second complementary probe. Each of the three first complementary probes has a different 3' terminal nucleotide complementary to one of the three different base substitutions (SNPs) that could be present in the diploid genomic DNA. Each of the three first complementary probes also has a unique interrogation site bar code that provided the ability to identify the allele and locus that was detected with that exact form of the first complementary probe for that exact target polynucleotide and variant. The method was carried out as described in Example 2, except that for this locus the database contained three interrogation barcodes (one for each of the variants).

Figure 9:
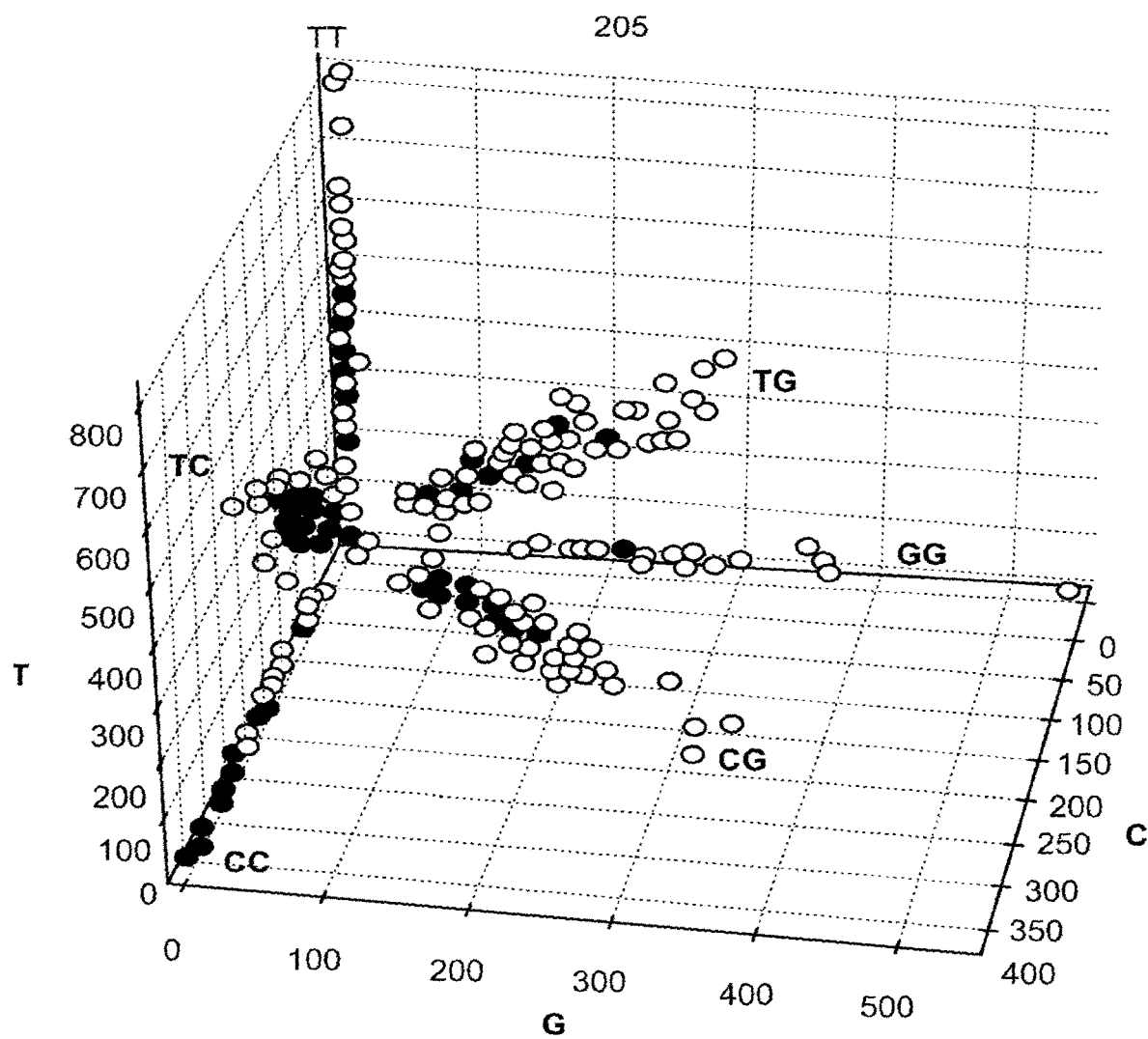
FIG. 9 illustrates the use of a genotyping embodiment for interrogation of polyallelic loci. The figure shows a cluster plot of a single poly-allelic locus. The three alleles are substitutions. Number of reads for Allele-A (x-axis) and Allele-B (y-axis) and Allele-C (z-axis) are shown, where each point is a unique sample. In this case Allele-A is the G base, Allele-B is the T base and Allele-C is the C base. AA animals are along the x-axis, BB animals are along the y-axis, CC animals are along the z-axis. Heterozygous animals (TC, TG, CG) fall between any two axis.

The sample index sequence and the interrogations site bar code sequence contained in each read was compared to a database, and the number of reads created from each sample×locus×allele was tabulated (and includes mis-assigned reads). For this locus the number of reads from the A allele (X-axis) and the number of reads of the B allele (Y-axis) and the number of reads of the C allele (z-axis) for each sample was plotted. This A allele vs B allele vs C allele plot is called a cluster plot. In this case Allele-A is the G base, Allele-B is the T base and Allele-C is the C base. AA animals are along the x-axis, BB animals are along the y-axis, CC animals are along the z-axis. Heterozygous animals (TC, TG, CG) fall between any two axis. This experiment demonstrates the ability to produce genotypes for polyallelic loci. The results are shown in FIG. 9.

Example 10. Genotyping Methods for Detection of Genetic Variations (Genetic Locus) Other than a Single Base Substitution Genotyping methods (and associated data analysis) are used to detect the presence of a target polynucleotide in a sample. In some cases the target polynucleotide may be the result of a deletion/insertion event. In this experiment, one form of the first complementary probe was designed to be complementary to the target sequence with the deletion, the other form of the first complementary probe was designed to be complementary to the target sequence that does not have the deletion. The second complementary probe is immediately adjacent to the 3' sequence on both forms of the first complementary probe. The workflow proceeded as described in Example 2.

Figure 10A:
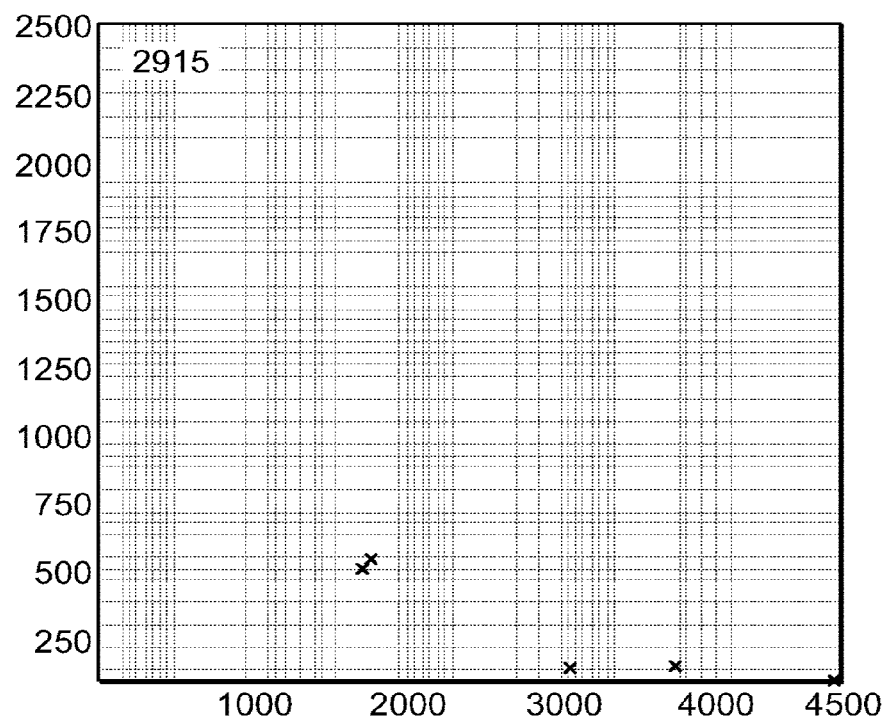
FIGS. 10A and 10B illustrate the results of a study where a nucleic acid sample was examined for the presence or absence of a particular sequence using an embodiment for the interrogation of deletions. Cluster plots of a locus with a three base deletion (FIG. 10A) and a 45 kb deletion (FIG. 10B). Number of reads for Allele-A (x-axis) and Allele-B (y-axis) are shown, where each point is a unique sample (the same 96 samples in each treatment). AA animals are along the x-axis, BB animals are along the y-axis, and AB animals are centered between the axes. The resolution of the cluster plots for loci that have deletions is similar to the resolution of the cluster plots for loci that are single base substitutions.
Figure 10B:
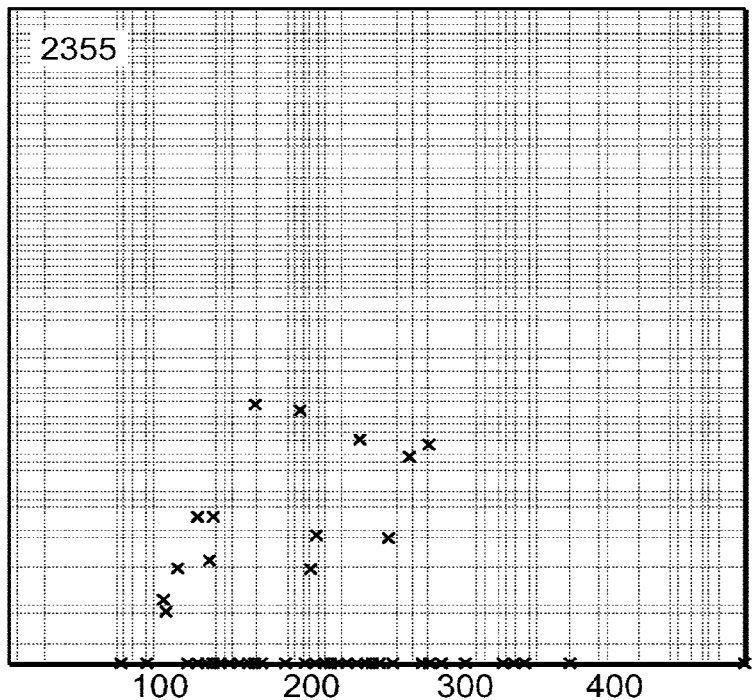

For each locus the number of reads from the A allele (X-axis) and the number of reads of the B allele (Y-axis) for each sample was plotted. In this case, the A and B alleles are the insertion and deletion (or vice a versa). This experiment demonstrates the ability to determine genotypes at genetic loci and variants that are not single base substitutions. The results are shown in FIGS. 10A and 10B.

Example 11. Methods for Selection and Optimization of the Sample Index Barcodes

The objective was to generate a total of 96,000 complementary probes having a 15mer sample index barcode between the universal primer sequence and the adaptor sequence (FIGS. 1C and 1D). These 15mer sample index barcodes also have 12 nucleotide (nt) reduced read-length compatibility for applications in which a lower number of different samples are being processed, thus allowing potential savings in, e.g., sequencing cost and time as only the first 12 nucleotides would need to be sequenced to identify a particular sample index. The theoretical maximum number of different 15mer sequences is 1,073,741,824 (4 nucleotides of a 15mer sequence is 4^15 different sequences=1,073,741,824). From this number, homopolymers were subtracted to give rise to a number of 139,839,696 15mers.

These 15mer sequences were further reduced through a selection process. The selection criteria included maximizing the orthogonality within the barcode and the barcode plus the flanking sequences (the universal primer sequence and the adaptor sequence); maximizing the specificity among barcodes so that they have no homopolymers and the GC content is about 40-60%; and ensuring commercial compatibility with e.g. Illumina TruSeq, Nextera indices to avoid subsequences for high-error rate sequences for the instruments. After the selection process, the barcodes were randomized and shuffled into barcode candidate vectors.

These barcodes were stored at both full and reduced read length sets. They were preloaded to commercial indices (extended with adapter). Numbers for barcodes were assigned from a maximum to minimum edit distance 'd.'

Each barcode within a candidate vector was checked for its GC content, tri-mers subject to phasing errors and searched for collision within both the full and reduced read set at given 'd.' If a barcode was not within either set, it was added to the pool of both sets.

Index Plate Ordering—the index plates were grouped by performance metrics to include, e.g., higher orthogonality/specificity in subsets of all plates. For each (384 well) plate of indexes to be generated, an optimum subset of barcodes was selected based on criteria from unassigned set of barcodes, e.g., 15/12 nt read edit distances. The subsets were assigned to individual plate and calculated for performance metrics per plate. The performance metrics was based on sequencing read counts. An example of performance metric is shown below.

| distance | count (15 nt read) | distance | count (12 nt read) |
| --- | --- | --- | --- |
| 0 | 0 | 0 | 0 |
| 1 | 0 | 1 | 0 |
| 2 | 0 | 2 | 0 |
| 3 | 0 | 3 | 0 |
| 4 | 0 | 4 | 526 |
| 5 | 46 | 5 | 3216 |
| 6 | 1643 | 6 | 10716 |
| 7 | 5938 | 7 | 21234 |
| 8 | 14236 | 8 | 23229 |
| 9 | 21807 | 9 | 12067 |
| 10 | 19537 | 10 | 2409 |
| 11 | 8504 | 11 | 135 |
| 12 | 1680 | 12 | 2 |
| 13 | 139 | 13 | 0 |

It was found that certain barcode sequences were inducing low sequencing read counts.

A motif in the barcode was discovered that caused interaction between the barcode and the adapter sequences. This motif was found to contain a sequence of about 7 bases (CTAGCCTCC) and can cause self-complementarity between the 3' end and the internal sequences of the complementary probes. Variations to this 7 bp motif theme were also discovered. Examples are shown in FIGS. 11A&B and FIGS. 12A&B.

A computer program was built to substitute for these problematic sequences, i.e., by incrementally optimizing the sequences as much as possible, and up to the full range of 96K barcodes. Since this particular motif seemed to affect performance more than the problematic tri-mers and edit distance, both of which can be factored in, all these were accounted for in the design/binning flows. However, with all the substitution, and under same criteria for edit distance globally, as well as locally optimized for each plate, 84,096 sample indexes were generated. The first 16, 128 of these indices can also be used as 12mers for experiments and applications where a more limited number of samples will be processed (e.g., to process ten 384 well microtiter plates, with one sample per well).

Example 12. Genotyping Methods for Detection of a Target Polynucleotide in Polyploidy Samples In this example, genotyping methods (and associated data analysis) for detecting the presence or absence of a target polynucleotide in polyploid wheat samples are described. Ploidy reduction strategies are used to reduce the generation of sequence data in non-informative genomes. In some cases, the target polynucleotide may be an SNP or the result of a deletion/insertion event (Indel).

In the first approach, public and proprietary wheat genome sequence data containing the target SNP/indel and the proximal SNP/indel information are obtained. Based on the knowledge of the relative position of the proximal SNP/indel to target marker SNP/indel, probes are designed that are selective for the genome of interest using the proximal SNP destabilization strategy to reduce ploidy through biological complexity. Target markers that are genotyped on Axiom and demonstrate diploid clusters are selected. It is also ensured that there are no proximal SNPs in the 9 bases on either side of the target marker (See FIGS. 14A-C).

One form of the first complementary probe was designed to be complementary to the target sequence with the SNP (LHS), the other form of the first complementary probe was designed to be complementary to the target sequence that does not have the SNP or indel (LHS'). The second complementary probe (RHS) is immediately adjacent to the 3' sequence on both forms of the first complementary probe. Selection was accomplished for the genome of interest (i.e., the target genome with the proximal SNP will generate low sequence counts). Accommodating the proximal SNP in the probe design causes a locus that produces no reads to become fully functioning (See, FIGS. 15A&B). The workflow proceeded as described in Example 2.

In the second approach, public and proprietary wheat genome sequence data containing the target SNP/indel and the proximal SNP/indel information are obtained. Based on the knowledge of the relative position of the proximal SNP/indel to target marker SNP/indel, blocking oligos that are complementary to the target genome sequence having the proximal SNP/indel are added to prevent hybridization of RHS to the target genome.

One form of the first complementary probe was designed to be complementary to the target sequence with the SNP/indel (LHS), the other form of the first complementary probe was designed to be complementary to the target sequence that does not have the SNP/indel (LHS'). The second complementary probe (RNS) is immediately adjacent to the 3' sequence on both forms of the first complementary probe. Blocking/competing oligos that are complementary to sequences containing the proximal SNPs in the target genome are added. Blocking oligos prevent hybridization of RHS to target genome. Selection was accomplished for the genome of interest (i.e., the target genome with the proximal SNP will generate low to none sequence reads). Accommodating the proximal SNP in the probe design with the addition of blocking oligos causes a locus that produces no reads (See, FIGS. 16A&B). This approach is suitable for when proximal SNP is between base 1 and 10 of target marker. Secondary polymorphism may not be destabilized. The workflow proceeded as described in Example 2.

In the third approach, public and proprietary wheat genome sequence data containing the target SNP/indel and the proximal SNP/indel information are obtained. Based on the knowledge of the relative position of the proximal SNP/indel to target marker SNP/indel, PCR primers are designed that selectively amplify unique genome or subgenome of interest. In this approach, an upfront PCR amplification step is added. One or both of the PCR primers that are complementary to the target genome sequence may hybridize to the proximal SNP in the target genome sequence. This upfront step using PCR amplification may be in parallel workflow format (i.e., the samples are divided into two).

One form of the first complementary probe was designed to be complementary to the target sequence with the SNP/indel (LHS), the other form of the first complementary probe was designed to be complementary to the target sequence that does not have the SNP/indel (LHS'). The second complementary probe (RHS) is immediately adjacent to the 3' sequence on both forms of the first complementary probe. An upfront PCR amplification step is added using PCR primers designed to specifically amplify unique genome or subgenome of interest. The proximal SNP/indel likely destabilizes the hybridization of the PCR primers. Selection is accomplished for the desired genome of interest (i.e., the none desired genome containing the proximal SNPs are eliminated from subsequent workflow). Various locus and genome combinations are accommodated using multiple PCR primer set and probe set combinations (See, FIGS. 17A&B). The workflow proceeded as described in Example 2.

For each locus the number of reads from the A allele (X-axis) and the number of reads of the B allele (Y-axis) for each sample was plotted. (Axiom cluster plot analysis). This experiment demonstrates the ability to select for the genome of interest using knowledge of proximal SNP/indel to identify target SNP/indel and design probes for selection. Results are shown in FIGS. 18A&B.

In a further approach, a 600× average coverage may be used for a small number of select markers. This approach requires parallel workflow (i.e., samples are divided into two). In some cases, samples are split between the markers at issue with nearby proximal SNPs or single base indels, and for the affected markers, instead of sequencing for 200× coverage as used in other approaches, it simply increases that for the split with the affected markers to having 600× coverage (i.e., to use additional sequencing time and expense to compensate instead of trying to compensate on the upfront Eureka portion). This approach has been used in other contexts, such as deep sequencing for expression with RNA-Seq to assist with detection of rare transcripts, so in a different context this would be the Eureka equivalent.

Example 13. Methods for Detection of a Target RNA without Conversion to cDNA

In this example, methods (and associated data analysis) for detecting RNA targets without conversion to cDNAs are described. In an exemplary approach, multiplexed ligation mediated PCR is performed on RNA targets, with the use of a new commercially available ligase (Splintr, from NEB) that can ligate adjacent DNA probes that are hybridized to RNA strands. This RNA based multiplex ligation-mediated PCR can perform a multitude of assays, where the RNA does not need to be converted to cDNA. The method described herein has the benefit of eliminating the RNA to cDNA conversion bias. The method described herein has potential uses in interrogating RNA, with the benefit of detecting strand specific allele usages, copy number determination of RNA and mRNA transcripts, alternative splicing and splice variants analysis, and detection of fusion genes. The method described in this example is a direct extension of the herein described DNA based multiplexed ligation-mediated PCR detection methods, but with RNA rather than DNA as targets.

A set of 778 loci amongst various human mRNA transcripts where the exon to exon boundaries were known were chosen. Probes were designed to interrogate these mRNA transcripts. The fusion genes are usually joined between the 5' end of one gene and the 3' end of another gene. The breakpoint of each gene occurs at varying locations in the DNA, but most often occurs in introns so that spliced RNA usually finds the breakpoint at an exon boundary. The probes were designed to cover the ends of exons bracketing introns with known fusion breakpoints. For positive controls, probes were designed to place at the end of exons bracketing introns for Beta Actin and GAPDH genes, which have no known fusions. For negative controls, probes were designed to place at the ends of introns for Beta Actin and GAPDH genes, which would only amplify in the presence of DNA.

The ligation mediated PCR requires a pair of two types of DNA probes, a first complementary probe, and a second complementary probe that is phosphorylated at the 5' end. A DNA or RNA specific ligase will be able to join the 3'OH group of the first complementary probe to the 5' phosphorylated group of the second complementary probe if the two DNA probes are hybridized to a target DNA or RNA template, respectively. The first complementary probes were designed to hybridize at the exon boundaries and the second complementary probes were designed to hybridize at an exon that is immediately adjacent to the exon to which the first complementary probes hybridize. For example, if the first complementary probes were designed to hybridize to Exon II, the respective second complementary probes would be designed to hybridize to Exon III. In this way, the first and second complementary probe pair would only be able to detect the RNA transcripts containing properly spliced Exon II to Exon III events. Other second complementary probes can be designed, e.g., when second complementary probes are designed for hybridizing to Exon IV, the assay will detect Exon II/Exon IV splice variants. The DNA probes were between 20 and 50 bases in length in order to achieve the calculated annealing temperature of between 68° C. to 74° C. Each first complementary probe has a common/universal PCR primer site at the 5' end while each second complementary has a different common/universal PCR primer site at the 3' end. The use of the common/universal PCR primer sites allows for sample specific indexing PCR to amplify the ligated products. All the probes are blended into a single blend at 50 pM in a high salt buffer (750 mM KCl, 30 mM Tris-HCl pH=8.5, 0.5 mM EDTA pH=8.0).

Commercially obtained human cell line RNA (HeLa), high salt probe buffer, and RNA protection reagents were mixed into a small 8 ul reaction, contained in the wells of a 384 well plate, and sealed with a heated foil seal. The hybridization reaction was heated in a PCR machine to 95° C. for 1 minute then dropped to 60° C. for 20 hours to promote hybridization. Just prior to ligation, the hybridization reaction is cooled to 54° C. and then placed on wet ice.

The ligation mixture including the Splintr enzyme (units/Rx) with its 1× reaction buffer was dispensed into 32 μl per reaction and cooled to wet ice temperature. The hybridization reaction, 8 μl, was then added into the ligation reaction mixture and mixed up. The total mixture was first heated to 54° C. for 15 minutes, and then heated to 92° C. for 15 seconds to dehybridize any nonligated probes, and cooled to 4° C. or frozen.

The PCR mixture included a standard PCR reaction buffer, a common PCR primer in the first complementary probe bearing an Illumina sequencing flow cell binding sequence and a common PCR primer in the second complementary probe that is uniquely indexed (sample index) near the end of the other half of the Illumina flow cell binding sequence. The PCR primers in this mixture will amplify any ligated product of the first and second complementary probes. Sample indexed PCR reaction products were pooled, cleaned up on a silica column to remove excess salt, enzyme and small probes and primers. This pooled library was quantified and qualified for size requirements. The hallmark of a successful reaction is the product size shift from a 150 bp long (noise artifact) to a 210 bp long (the signal) resulting from the PCR amplification of successfully ligated products of the first and second complementary probes.

Sequencing of the PCR amplification products will reveal information of the first and second complementary probe junctions, e.g., of Exon II/Exon III or perhaps Exon II/Exon IV splice variants. Duplicate reads can be counted (binned) and those counts can be used to infer the relative copy number of the RNA transcripts.

Figure 19:
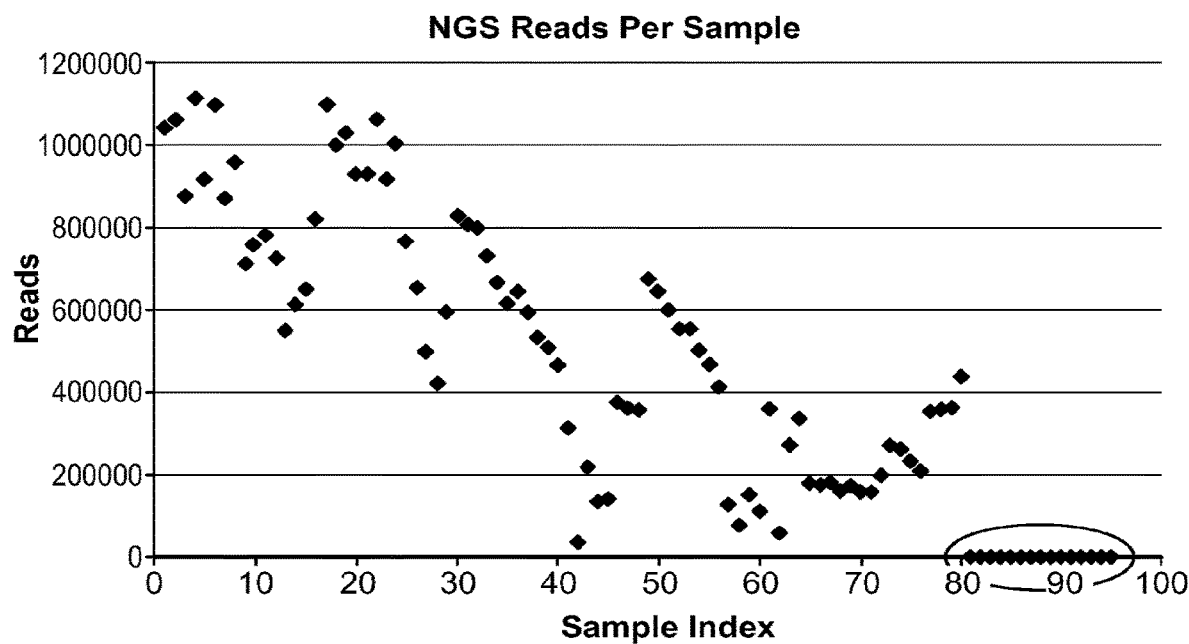
FIG. 19 illustrates the results of a study demonstrating that SplintR ligase can ligate adjacent DNA probes that are hybridized to mRNA transcripts from Human HeLa cell line. Total reads (across all loci) for each sample are shown. When the SplintR ligase was omitted from the reaction nearly zero reads were detected (total of 16 independent reactions). This set of data omits any first complementary probe that does not have its partner second complementary probe ligated to it, essentially removing the noise of spurious first complementary probe aberrant ligation products.
Figure 20:
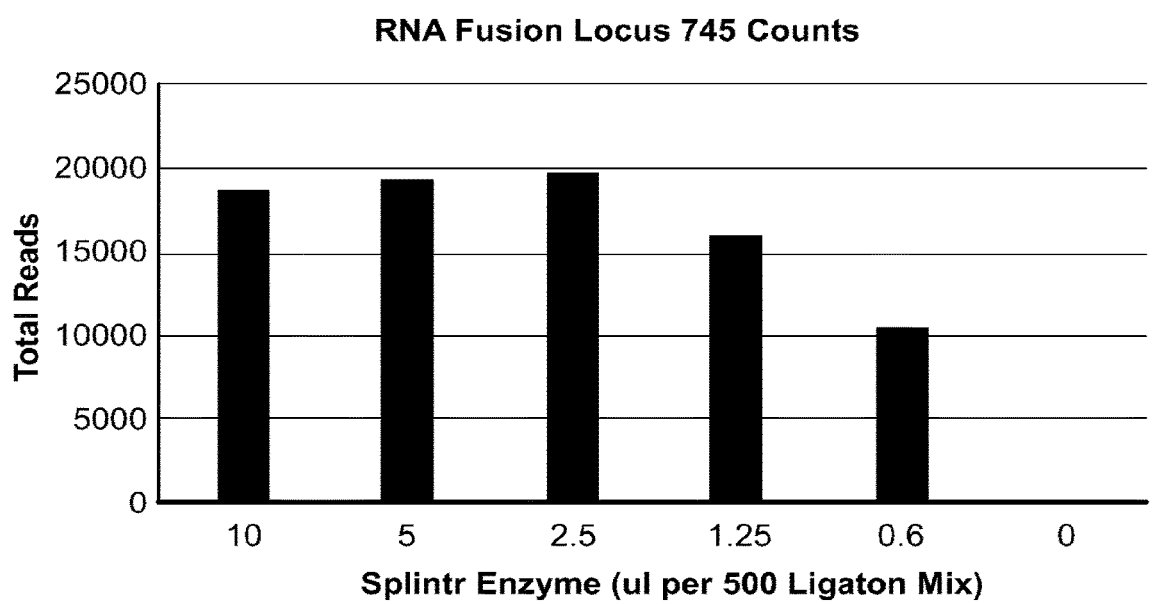
FIG. 20 illustrates the results of the total read counts of the mRNA transcripts of the glyceraldehyde 3-phosphate dehydrogenase (GADPH) gene (arbitrarily assigned as locus 745 of the 778 loci panel) against a titration of the SplintR ligase (µL of stock SplintR enzyme [25 Units/µL] per 500 ml of ligation Mix). As the unit concentration of the SplintR ligase falls, so do the binned reads counts across the multiple replicates. With zero unit of the RNA ligase, there are no binned read for this locus. The SplintR ligase reaction is dependent upon the concentration of the SplintR ligase.
Figure 21:
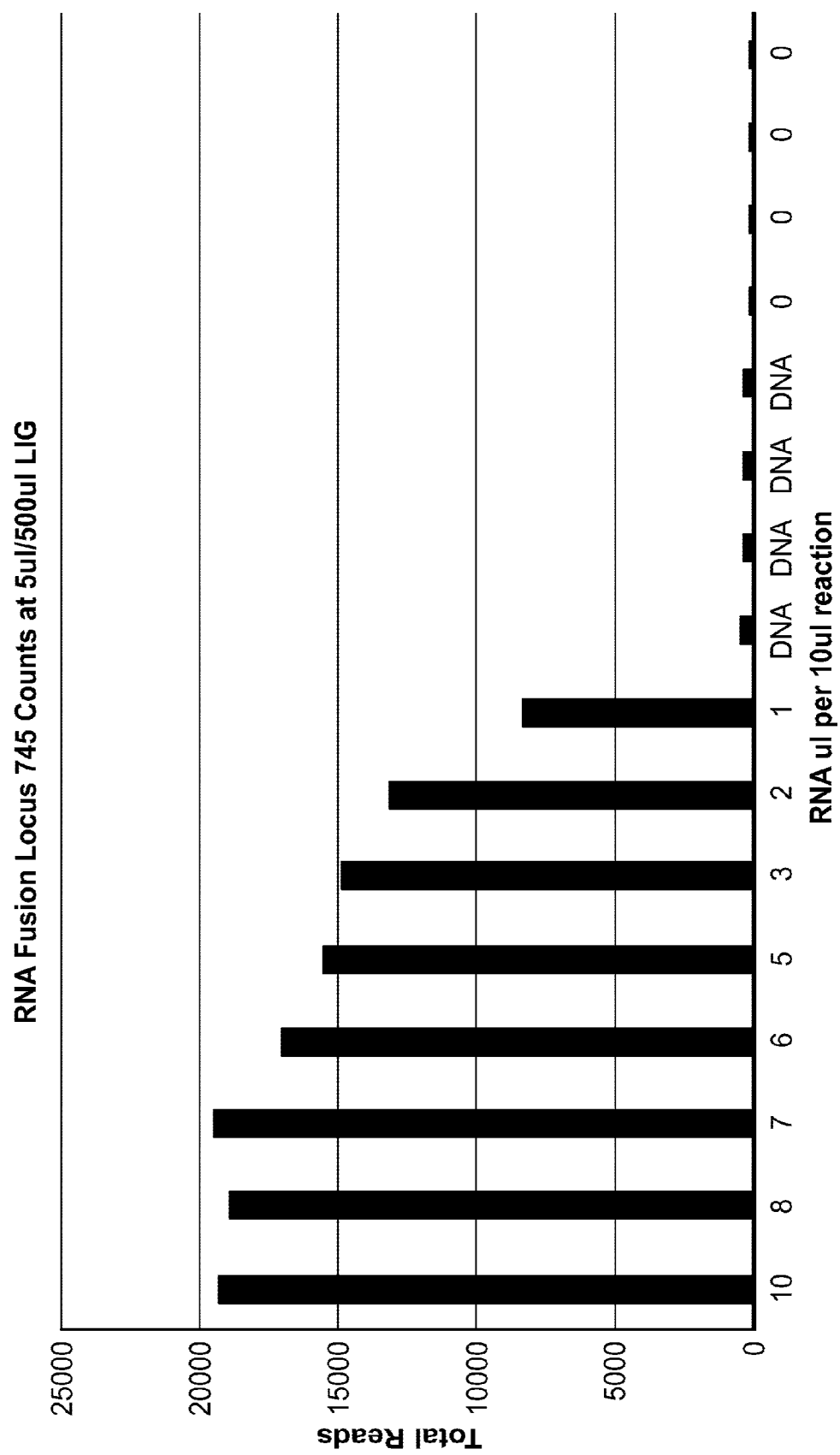
FIG. 21 illustrates the results of the total read counts of the mRNA transcripts of the glyceraldehyde 3-phosphate dehydrogenase (GADPH) gene (arbitrarily assigned as locus 745 of the 778 loci panel) against a titration of input RNA as well as human genomic DNA. As the concentration of RNA in the reaction falls, so do the number of binned locus 745 read counts. With zero input RNA but a presence of DNA, a small amount of binned signal is detected. With neither input RNA nor DNA, the binned signal approaches zero. The SplintR ligase reaction is RNA dependent but does have a trace amount of activity with DNA.

To demonstrate that the ligase specific products were being generated by the hybridization and ligation reactions, a set of 96 reactions were performed and the total reads across all loci for each sample were shown (FIG. 19). Positive read counts indicated that the ligase specific products were being generated for the samples analyzed. When the ligase was omitted from the reaction, nearly zero reads were detected (total of 16 independent reactions) (FIG. 19, lower right dots in the oval). This set of data omits any first complementary probe that does not have its partner second complementary probe ligated to it, essentially removing the noise of spurious first complementary probe aberrant ligation products. In addition, titration studies were also conducted where input ligase concentration (units/reaction) and input RNA were titrated down to zero (FIGS. 20 and 21). The total read counts of the mRNA transcripts of the glyceraldehyde 3-phosphate dehydrogenase (GADPH) gene (arbitrarily assigned as locus 745 of the 778 loci panel) against a titration of the ligase study indicated that the ligase reaction is dependent upon the input ligase concentration (FIG. 20). The total read counts of the mRNA transcripts of the glyceraldehyde 3-phosphate dehydrogenase (GADPH) gene (arbitrarily assigned as locus 745 of the 778 loci panel) against a titration of the input RNA study indicated that the ligation reaction is dependent upon the amount of input RNA (FIG. 21). In FIG. 21, a human DNA sample was also included to demonstrate that the splice effect has dependence on RNA and not DNA. For these studies, only the GADPH gene transcripts (locus 745, Exon VII) were examined by binned read counts. Fusion gene products were not expected in this HeLa based data set.

Although a variety of examples and other information are provided above to explain aspects within the scope of the claims, no limitation of the claims should be implied based on particular features or arrangements in such examples, as one of ordinary skill would be able to use these examples to derive a wide variety of implementations. Furthermore, although some subject matter may have been described in language specific to examples of structural features, conditions or uses, it is to be understood that the subject matter defined in the claims is not necessarily so limited.

The invention claimed is:

1. A composition for analyzing a target polynucleotide in a sample, the composition comprising:
    a first probe configured to hybridize to a first target sequence of the target polynucleotide, the first probe including
        (i) an interrogation site bar code that is non-complementary to the first target sequence,
        (ii) a first complementary sequence portion 5' of the interrogation site barcode, the first complementary sequence portion being complementary to the first target sequence,
        (iii) a second complementary sequence portion 3' of the interrogation site barcode, the second complementary sequence portion being complementary to the first target sequence, and
        (iv) a universal sequence that is non-complementary to the first target sequence, the universal sequence being 5' of the first complementary sequence portion; and
    a second probe configured to hybridize to a second target sequence of the target polynucleotide, the second probe including
        (i) a complementary sequence portion that is complementary to the second target sequence, and
        (ii) a non-complementary sequence that is non-complementary to the second target sequence.

2. The composition of claim 1, wherein the non-complementary sequence of the second probe and the complementary sequence of the second probe are immediately adjacent one another.

3. The composition of claim 2, wherein the non-complementary sequence of the second probe is 3' of the complementary sequence of the second probe.

4. The composition of claim 1, wherein the non-complementary sequence of the second probe comprises a universal sequence.

5. The composition of claim 4, wherein the universal sequence of the second probe and the universal sequence of the first probe are the same.

6. The composition of claim 1, wherein the 3' end of the first probe is complementary to one form of a single nucleotide polymorphism (SNP) or other genetic variation.

7. The composition of claim 1, wherein the first and second probes are configured to be adjacent one another when hybridized to the target polynucleotide.

8. The composition of claim 1, wherein the first and second probes are configured to be spaced by 1 to 500 nucleotides when hybridized to the target polynucleotide.

9. The composition of claim 1, wherein the interrogation site bar code is 10-16 nucleotides in length.

10. A composition for analyzing a target polynucleotide in a sample, the composition comprising:
   a first probe configured to hybridize to a first target sequence of the target polynucleotide, the first probe including
   (v) an interrogation site bar code that is non-complementary to the first target sequence,
   (vi) a first complementary sequence portion 5' of the interrogation site barcode, the first complementary sequence portion being complementary to the first target sequence,
   (vii) a second complementary sequence portion 3' of the interrogation site barcode, the second complementary sequence portion being complementary to the first target sequence, and
   (viii) a universal sequence that is non-complementary to the first target sequence; and
   a second probe configured to hybridize to a second target sequence of the target polynucleotide, the second probe including
   (iii) a complementary sequence portion that is complementary to the second target sequence, and
   (iv) a non-complementary sequence that is non-complementary to the second target sequence,
   wherein the first probe is configured to hybridize to the target polynucleotide 5' of the second probe.

11. The composition of claim 10, wherein the non-complementary sequence of the second probe and the complementary sequence of the second probe are immediately adjacent one another.

12. The composition of claim 11, wherein the non-complementary sequence of the second probe is 3' of the complementary sequence of the second probe.

13. The composition of claim 10, wherein the non-complementary sequence of the second probe comprises a universal sequence.

14. The composition of claim 13, wherein the universal sequence of the second probe and the universal sequence of the first probe are the same.

15. The composition of claim 10, wherein the 3' end of the first probe is complementary to one form of a single nucleotide polymorphism (SNP) or other genetic variation.

16. The composition of claim 10, wherein the first and second probes are configured to be adjacent one another when hybridized to the target polynucleotide.

17. The composition of claim 10, wherein the first and second probes are configured to be spaced by 1 to 500 nucleotides when hybridized to the target polynucleotide.

18. The composition of claim 10, wherein the interrogation site bar code is 10-16 nucleotides in length.

19. A kit for analyzing a target polynucleotide in a sample, the kit comprising:
   the composition of claim 1; and
   a set of primers, at least one of which is a universal primer complementary to the universal sequence of the first probe.

20. The kit of claim 19, further comprising an additional sequence that includes one or more of: a sample index; an adaptor for next generation sequencing; or a capture probe or sequence, wherein the set of primers is configured to add the additional sequence.

* * * * *